(12) United States Patent
Dakka et al.

(10) Patent No.: US 10,501,482 B2
(45) Date of Patent: Dec. 10, 2019

(54) COMPOUNDS FOR TREATING SPINAL MUSCULAR ATROPHY

(71) Applicants: Hoffmann-La Roche Inc., Nutley, NJ (US); PTC Therapeutics Inc., South Plainfield, NJ (US)

(72) Inventors: Amal Dakka, Whitehouse Station, NJ (US); Luke Green, Basel (CH); Gary Karp, Princeton Junction, NJ (US); Jana Narasimhan, Scotch Plains, NJ (US); Nikolai Naryshkin, East Brunswick, NJ (US); Emmanuel Pinard, Linsdorf (FR); Hongyan Qi, Plainsboro, NJ (US); Hasane Ratni, Habsheim (FR); Nicole Risher, Hillsborough, NJ (US); Marla Weetall, Morristown, NJ (US); Matthew Woll, Dunellen, NJ (US)

(73) Assignees: Hoffmann—La Roche Inc., Nutley, NJ (US); PTC Therapeutics Inc., South Plainfield, NJ (US)

(*) Notice: Subject to any disclaimer, the term of this patent is extended or adjusted under 35 U.S.C. 154(b) by 0 days.

(21) Appl. No.: 15/948,444

(22) Filed: Apr. 9, 2018

(65) Prior Publication Data
US 2018/0222925 A1    Aug. 9, 2018

Related U.S. Application Data

(63) Continuation of application No. 14/899,397, filed as application No. PCT/US2014/043577 on Jun. 23, 2014, now abandoned.

(30) Foreign Application Priority Data

Jun. 25, 2013 (EP) ..................... 13173487

(51) Int. Cl.
| | |
|---|---|
| C07D 519/00 | (2006.01) |
| C07D 487/10 | (2006.01) |
| C07D 263/56 | (2006.01) |
| C07D 471/04 | (2006.01) |
| C07D 413/12 | (2006.01) |
| C07D 487/04 | (2006.01) |

(52) U.S. Cl.
CPC ......... *C07D 519/00* (2013.01); *C07D 263/56* (2013.01); *C07D 413/12* (2013.01); *C07D 471/04* (2013.01); *C07D 487/04* (2013.01); *C07D 487/10* (2013.01)

(58) Field of Classification Search
None
See application file for complete search history.

(56) References Cited

U.S. PATENT DOCUMENTS 8,765,743 B2 *   7/2014   Baldwin .............. C07D 401/14
                                              514/228.5

FOREIGN PATENT DOCUMENTS

| WO | 2006101455 A1 | 9/2006 |
| WO | 2009042907 A1 | 4/2009 |
| WO | 2012/142459 A1 | 10/2012 |

OTHER PUBLICATIONS

The English translation of the Chinese Office Action, dated Jun. 8, 2017, in the related Chinese Application No. 201480035676.2.
The extended European Search Report, dated Nov. 3, 2016, in the corresponding European Patent Application No. 14816651.5.

* cited by examiner

*Primary Examiner* — Kamal A Saeed

(57) ABSTRACT

The present invention provides compounds of formula (I) wherein A, B, X, Y, R1 and R2 are as described herein, as well as pharmaceutically acceptable salts thereof. Further the present invention is concerned with the manufacture of the compounds of formula (I), pharmaceutical compositions comprising them and their use as medicaments.

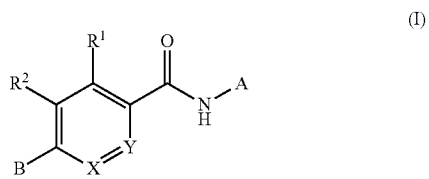

(I)

31 Claims, No Drawings
Specification includes a Sequence Listing.

COMPOUNDS FOR TREATING SPINAL MUSCULAR ATROPHY

CROSS-REFERENCE TO RELATED APPLICATIONS

This application is Continuation Patent Application of U.S. Ser. No. 14/899,397 filed Dec. 15, 2017, which claims priority from a National Stage Application of PCT/US2014/043577 filed Jun. 23, 2014, which claims priority from European Patent Application No. 13173487.3, filed on Jun. 25, 2013. The priority of both said PCT and European Patent Application are claimed. Each of prior mentioned applications is hereby incorporated by reference herein in its entirety.

INTRODUCTION

The present invention provides compounds which are SMN2 gene splicing modulators, their manufacture, pharmaceutical compositions comprising them and their use as medicaments for the treatment of spinal muscular atrophy (SMA).

In particular, the present invention relates to compounds of formula (I)

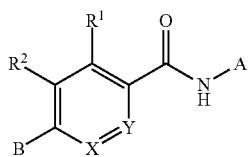

wherein A, B, X, Y, $R^1$ and $R^2$ are as described herein, and pharmaceutically acceptable salts thereof.

BACKGROUND

Spinal muscular atrophy (SMA), in its broadest sense, describes a collection of inherited and acquired central nervous system (CNS) diseases characterized by progressive motor neuron loss in the spinal cord and brainstem causing muscle weakness and muscle atrophy. The most common form of SMA is caused by mutations in the Survival Motor Neuron (SMN) gene and manifests over a wide range of severity affecting infants through adults (Crawford and Pardo, *Neurobiol. Dis.*, 1996, 3:97).

Infantile SMA is the most severe form of this neurodegenerative disorder. Symptoms include muscle weakness, poor muscle tone, weak cry, limpness or a tendency to flop, difficulty sucking or swallowing, accumulation of secretions in the lungs or throat, feeding difficulties, and increased susceptibility to respiratory tract infections. The legs tend to be weaker than the arms and developmental milestones, such as lifting the head or sitting up, cannot be reached. In general, the earlier the symptoms appear, the shorter the lifespan. As the motor neuron cells deteriorate, symptoms appear shortly afterward. The severe forms of the disease are fatal and all forms have no known cure. The course of SMA is directly related to the rate of motor neuron cell deterioration and the resulting severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. The clinical spectrum of SMA disorders has been divided into the following five groups.

(a) Type 0 SMA (In Utero SMA) is the most severe form of the disease and begins before birth. Usually, the first symptom of Type 0 SMA is reduced movement of the fetus that can first be observed between 30 and 36 weeks of pregnancy. After birth, these newborns have little movement and have difficulties with swallowing and breathing.

(b) Type 1 SMA (Infantile SMA or Werdnig-Hoffmann disease) presents symptoms between 0 and 6 months. form of SMA is also very severe. Patients never achieve the ability to sit, and death usually occurs within the first 2 years without ventilatory support.

(c) Type 2 SMA (Intermediate SMA) has an age of onset at 7-18 months. Patients achieve the ability to sit unsupported, but never stand or walk unaided. Prognosis in this group is largely dependent on the degree of respiratory involvement.

(d) Type 3 SMA (Juvenile SMA or Kugelberg-Welander disease) is generally diagnosed after 18 months. Type 3 SMA individuals are able to walk independently at some point during their disease course but often become wheelchair-bound during youth or adulthood.

(e) Type 4 SMA (Adult onset SMA). Weakness usually begins in late adolescence in the tongue, hands, or feet, then progresses to other areas of the body. The course of adult SMA is much slower and has little or no impact on life expectancy.

The SMN gene has been mapped by linkage analysis to a complex region in chromosome 5q. In humans, this region contains an approximately 500 thousand base pairs (kb) inverted duplication resulting in two nearly identical copies of the SMN gene. SMA is caused by an inactivating mutation or deletion of the telomeric copy of the gene (SMN1) in both chromosomes, resulting in the loss of SMN1 gene function. However, all patients retain the centromeric copy of the gene (SMN2), and the copy number of the SMN2 gene in SMA patients generally correlates inversely with the disease severity; i.e., patients with less severe SMA have more copies of SMN2. Nevertheless, SMN2 is unable to compensate completely for the loss of SMN1 function due to alternative splicing of exon 7 caused by a translationally silent C to T mutation in exon 7. As a result, the majority of transcripts produced from SMN2 lack exon 7 (Δ7 SMN2), and encode a truncated SMN protein that has an impaired function and is rapidly degraded.

The SMN protein is thought to play a role in RNA processing and metabolism, having a well characterized function of mediating the assembly of a specific class of RNA-protein complexes termed snRNPs. SMN may have other functions in motor neurons, however its role in preventing the selective degeneration of motor neurons is not well established.

In most cases, SMA is diagnosed based on clinical symptoms and by the presence of at least one copy of the SMN1 gene test. However, in approximately 5% of cases SMA is caused by mutation in genes other than the inactivation of SMN 1, some known and others not yet defined. In some cases, when the SMN 1 gene test is not feasible or does not show any abnormality, other tests such as an electromyography (EMG) or muscle biopsy may be indicated.

Medical care for SMA patients at present is limited to supportive therapy including respiratory, nutritional and rehabilitation care; there is no drug known to address the underlying cause of the disease. Current treatment for SMA consists of prevention and management of the secondary effects of chronic motor unit loss. The major management issue in Type 1 SMA is the prevention and early treatment of pulmonary problems, which are the cause of death in the majority of the cases. While some infants afflicted with SMA grow to be adults, those with Type 1 SMA have a life expectancy of less than two years.

Several mouse models of SMA have been developed. In particular, the SMN delta exon 7 (Δ7 SMN) model (Le et al., *Hum. Mol. Genet.*, 2005, 14:845) carries both the SMN2 gene and several copies of the Δ7 SMN2 cDNA and recapitulates many of the phenotypic features of Type 1 SMA. The Δ7 SMN model can be used for both SMN2 expression studies as well as the evaluation of motor function and survival. The C/C-allele mouse model (Jackson Laboratory strain #008714, The Jackson Laboratory, Bar Harbor, Me.) provides a less severe SMA disease model, with mice having reduced levels of both SMN2 full length (FL SMN2) mRNA and SMN protein. The C/C-allele mouse phenotype has the SMN2 gene and a hybrid mSMN1-SMN2 gene that undergoes alternative splicing, but does not have overt muscle weakness. The C/C-allele mouse model is used for SMN2 expression studies.

As a result of improved understanding of the genetic basis and pathophysiology of SMA, several strategies for treatment have been explored, but none have yet demonstrated success in the clinic.

Gene replacement of SMN1, using viral delivery vectors, and cell replacement, using differentiated $SMN1^{+/+}$ stem cells, have demonstrated efficacy in animal models of SMA. More research is needed to determine the safety and immune response and to address the requirement for the initiation of treatment at the neonatal stage before these approaches can be applied to humans.

Correction of alternative splicing of SMN2 in cultured cells has also been achieved using synthetic nucleic acids as therapeutic agents: (i) antisense oligonucleotides that target sequence elements in SMN2 pre-mRNA and shift the outcome of the splicing reaction toward the generation of full length SMN2 mRNA (Passini et al., *Sci. Transl. Med.*, 2011, 3:72ra18; and, Hua et al., *Nature*, 2011, 478:123) and (ii) trans-splicing RNA molecules that provide a fully functional RNA sequence that replace the mutant fragment during splicing and generate a full length SMN1 mRNA (Coady and Lorson, *J Neurosci.*, 2010, 30:126).

Other approaches under exploration include searching for drugs that increase SMN levels, enhance residual SMN function, or compensate for its loss. Aminoglycosides have been shown to enhance expression of a stabilized SMN protein produced from Δ7 SMN2 mRNA by promoting the translational read-through of the aberrant stop codon, but have poor central nervous system penetration and are toxic after repeat dosing. Chemotherapeutic agents, such as aclarubicin, have been shown to increase SMN protein in cell culture; however, the toxicity profile of these drugs prohibits long-term use in SMA patients. Some drugs under clinical investigation for the treatment of SMA include transcription activators such as histone deacetylase ("HDAC") inhibitors (e.g., butyrates, valproic acid, and hydroxyurea), and mRNA stabilizers (mRNA decapping inhibitor RG3039 from Repligen), the goal being to increase the amount of total RNA transcribed from the SMN2 gene. However, the use of the HDAC inhibitors or mRNA stabilizers does not address the underlying cause of SMA and may result in a global increase in transcription and gene expression with potential safety problems in humans.

In an alternative approach, neuroprotective agents such as Olesoxime have been chosen for investigation. Such strategies are not aimed at SMN for the treatment of SMA, but instead are being explored to protect the SMN-deficient motor neurons from neurodegeneration.

A system designed for identifying compounds that increase the inclusion of exon 7 of SMN into RNA transcribed from the SMN2 gene and certain benzooxazole and benzoisoxazole compounds identified thereby have been described in International Patent Application WO2009/151546A1. A system designed for identifying compounds that cause ribosomal frameshifting to produce a stabilized SMN protein from Δ7 SMN2 mRNA and certain isoindolinone compounds identified thereby have been described in International Patent Application WO2010/019236A1.

Despite the progress made in understanding the genetic basis and pathophysiology of SMA, there remains a need to identify compounds that alter the course of spinal muscular atrophy, one of the most devastating childhood neurological diseases.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

The term "moiety" refers to an atom or group of chemically bonded atoms that is attached to another atom or molecule by one or more chemical bonds thereby forming part of a molecule. For example, the variables $R^1$ and $R^2$ of formula (I) refer to moieties that are attached to the core structure of formula I by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds of formula (I) as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

Particular pharmaceutically acceptable salts of the present invention are salts formed with hydrochloric acid yielding a hydrochloride, dihydrochloride, or trihydrochloride salt.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The "basicity" of a compound is expressed herein by the negative decadic logarithm of the acidity constant of the conjugate acid (pKa=−log Ka). The larger the pKa of the conjugate acid, the stronger the base (pKa+pKb=14). In this application, an atom or functional group is denoted "basic" if it is suitable to accept a proton and if the calculated pKa of its conjugate acid is at least 7, more particularly if the calculated pKa of its conjugate acid is at least 7.8, most particularly if the calculated pKa of its conjugate acid is at least 8. pKa values were calculated in-silico as described in F. Milletti et al., *J. Chem. Inf. Model* (2007) 47:2172-2181.

The term "halo", "halogen", and "halide" are used interchangeably herein and denote fluoro, chloro, bromo, or iodo. Particular examples of halo are fluoro and chloro, most particularly fluoro.

The term "alkyl" denotes a monovalent linear or branched saturated hydrocarbon group of 1 to 7 carbon atoms. In particular embodiments, alkyl has 1 to 4 carbon atoms, and in more particular embodiments 1 to 2 carbon atoms. Examples of alkyl include methyl, ethyl, propyl, isopropyl, n-butyl, iso-butyl, sec-butyl, or tert-butyl. Particular examples of alkyl are methyl and ethyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy are methoxy and ethoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular example of haloalkyl is trifluoromethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms. Particular example of haloalkoxy is 2,2,2-trifluoroethoxy.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic hydrocarbon group of 3 to 7 ring carbon atoms. Examples for cycloalkyl are cyclopropyl, cyclobutanyl, cyclopentyl, cyclohexyl or cycloheptyl. Particular example for cycloalkyl is cyclopropyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl are saturated or partially unsaturated mono- or bicyclic 4 to 9-membered heterocycloalkyl comprising one or two ring nitrogen atoms, the remaining ring atoms being carbon. Particular examples for monocyclic saturated heterocycloalkyl are piperidinyl and piperazinyl. Particular example for monocyclic partially unsaturated heterocycloalkyl is 1,2,3,6-tetrahydropyridin-4-yl. Particular examples for bicyclic saturated heterocycloalkyl are hexahydropyrrolo[1,2-a]pyrazin-2-yl, hexahydropyrrolo[3,4-c]pyrrol-2-yl, and 2,6-diazaspiro[3.3]heptan-2-yl. Most particular examples for heterocycloalkyl is piperazinyl.

The term "located opposite of the site of attachment" denotes the position of an atom in a cyclic ring system. If the point of attachment of a monocyclic ring to the rest of the molecular backbone is termed position 1, then "located opposite of the site of attachment" denotes position 3 for a monocylic 4-membered ring, positions 3 or 4 for a monocyclic 5-membered ring, position 4 for a monocyclic 6-membered ring, and positions 4 or 5 for a monocyclic 7-membered ring. For bicyclic ring systems, "located opposite of the site of attachment" denotes a ring atom of the second fused ring (including bridgehead atoms).

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular examples for heteroaryl are bicyclic 9-membered heteroaryl comprising 2 or 3 heteroatoms selected from N or O. More particular examples for heteroaryl are imidazo[1,2-a]pyrazin-2-yl, imidazo[1,2-a]pyridin-6-yl, and benzo[d]oxazol-6-yl. Most particular heteroaryl is imidazo[1,2-a]pyridin-6-yl.

The term "alkylene" denotes a linear saturated divalent hydrocarbon group of 2 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene. Particular examples of alkylene are methylene and ethylene.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Particular amino-protecting group is tert-butoxycarbonyl (BOC). Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide. Most particular deprotecting reagent is hydrochloric acid.

The term "active pharmaceutical ingredient" (or "API") denotes the compound or molecule in a pharmaceutical composition that has a particular biological activity.

The term "pharmaceutical composition" refers to a preparation which is in such form as to permit the biological activity of an active ingredient contained therein to be effective, and which contains no additional components which are unacceptably toxic to a subject to which the composition would be administered.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. In a particular embodiment of the invention the subject is a human with spinal muscular atrophy (SMA). In another specific embodiment, the subject is a human with SMA caused by an inactivating mutation or deletion in the SMN1 gene on both chromosomes, resulting in a loss of SMN1 gene function.

The term "spinal muscular atrophy" (or SMA) relates to a disease caused by an inactivating mutation or deletion in the SMN1 gene on both chromosomes, resulting in a loss of SMN1 gene function.

Symptoms of SMA include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

The term "treating spinal muscular atrophy (SMA)" or "treatment of spinal muscular atrophy (SMA)" includes one or more of the following effects: (i) reduction or amelioration of the severity of SMA; (ii) delay of the onset of SMA; (iii) inhibition of the progression of SMA; (iv) reduction of hospitalization of a subject; (v) reduction of hospitalization length for a subject; (vi) increase of the survival of a subject; (vii) improvement of the quality of life of a subject; (viii) reduction of the number of symptoms associated with SMA; (ix) reduction of or amelioration of the severity of one or more symptoms associated with SMA; (x) reduction of the duration of a symptom associated with SMA; (xi) prevention of the recurrence of a symptom associated with SMA; (xii) inhibition of the development or onset of a symptom of SMA; and/or (xiii) inhibition of the progression of a symptom associated with SMA.

More particular, "treating SMA" denotes one or more of the following beneficial effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In detail, "treating SMA" results in the functional ability or helps retain the functional ability for a human infant or a human toddler to sit up unaided or for a human infant, a human toddler, a human child or a human adult to stand up unaided, to walk unaided, to run unaided, to breathe unaided, to turn during sleep unaided, or to swallow unaided.

An "effective amount" of an agent, e.g., a pharmaceutical composition, refers to an amount effective, at dosages and for periods of time necessary, to achieve the desired therapeutic or prophylactic result.

The term "preventing" or "prevention" of a disease state denotes causing the clinical symptoms of the disease state not to develop in a subject that can be exposed to or predisposed to the disease state, but does not yet experience or display symptoms of the disease state.

The term "$EC_{1.5x}$ concentration for production of full length SMN2 minigene mRNA" (or "$EC_{1.5x}$ minigene") is defined as that concentration of test compound that is effective in increasing the amount of full length SMN2 minigene mRNA to a level 1.5-fold greater relative to that in vehicle-treated cells.

The term "$EC_{1.5x}$ concentration for SMN protein expression" (or "$EC_{1.5x}$ SMN protein") is defined as that concentration of test compound that is effective in producing 1.5 times the amount of SMN protein in an SMA patient fibroblast cell compared to the amount produced from the vehicle control.

In detail, the present invention relates to compounds of formula (I)

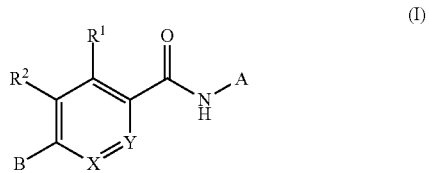

wherein

X is N or $CR^3$;

Y is N or $CR^4$; with the proviso that not both X and Y are N;

A is a bicyclic 9-membered heteroaryl comprising two or three heteroatoms independently selected from N or O, wherein A can be optionally substituted with one, two or three $R^5$;

B is a saturated or partially unsaturated mono- or bicyclic 4 to 9-membered heterocycloalkyl comprising one or two ring nitrogen atoms, the remaining ring atoms being carbon, wherein B can be optionally substituted with one, two or three $R^6$ $R^1$ is hydrogen, halo, $C_{1-7}$-alkyl, $C_{1-7}$-haloalkyl, $C_{1-7}$-alkoxy or $C_{1-7}$-haloalkoxy;

$R^2$ is hydrogen, halo, $C_{1-7}$-alkyl, $C_{1-7}$-haloalkyl, $C_{1-7}$-alkoxy or $C_{1-7}$-haloalkoxy;

$R^3$ is hydrogen, halo, $C_{1-7}$-alkyl, $C_{1-7}$-haloalkyl, $C_{1-7}$-alkoxy or $C_{1-7}$-haloalkoxy;

$R^4$ is hydrogen, halo, $C_{1-7}$-alkyl, $C_{1-7}$-haloalkyl, $C_{1-7}$-alkoxy or $C_{1-7}$-haloalkoxy;

each $R^5$ is independently selected from halo, cyano, $C_{1-7}$-alkyl, $C_{1-7}$-haloalkyl or $C_{3-7}$-cycloalkyl;

each $R^6$ is independently selected from $C_{1-7}$-alkyl, or two $R^6$ together form a $C_{2-7}$-alkylene;

and pharmaceutically acceptable salts thereof.

Particular embodiments of the present invention are compounds of formula (I) and pharmaceutically acceptable salts thereof.

Further, it is to be understood that every embodiment relating to a specific A, B, X, Y, $R^1$, $R^2$, $R^3$, $R^4$, $R^5$ or $R^6$ as disclosed herein may be combined with any other embodiment relating to another A, B, X, Y, $R^1$, $R^2$, $R^3$, $R^4$, $R^5$ or $R^6$ as disclosed herein.

A particular embodiment of the present invention relates to compounds of formula (I), wherein A is selected from the group of imidazo[1,2-a]pyrazin-2-yl, imidazo[1,2-a]pyridinyl, and benzo[d]oxazolyl, which can be optionally substituted with one, two or three $R^5$.

A particular embodiment of the present invention relates to compounds of formula (I), wherein A is selected from the group of imidazo[1,2-a]pyrazin-2-yl, imidazo[1,2-a]pyridin-6-yl, and benzo[d]oxazol-6-yl, which can be optionally substituted with one, two or three $R^5$.

A particular embodiment of the present invention relates to compounds of formula (I), wherein A is selected from the group of imidazo[1,2-a]pyrazin-2-yl substituted with two $C_{1-7}$-alkyl, imidazo[1,2-a]pyridin-6-yl substituted with one or two $C_{1-7}$-alkyl, imidazo[1,2-a]pyridin-6-yl substituted with one $C_{1-7}$-alkyl and one halo, imidazo[1,2-a]pyridin-6-yl substituted with one $C_{1-7}$-alkyl and one $C_{1-7}$-haloalkyl, benzo[d]oxazol-6-yl substituted with one $C_{1-7}$-alkyl, and benzo[d]oxazol-6-yl substituted with one $C_{1-7}$-alkyl and one halo.

A particular embodiment of the present invention relates to compounds of formula (I), wherein A is imidazo[1,2-a]pyridinyl which can be optionally substituted with one or two $R^5$.

A particular embodiment of the present invention relates to compounds of formula (I), wherein A is imidazo[1,2-a]pyridin-6-yl substituted with one $C_{1-7}$-alkyl and one halo.

A particular embodiment of the present invention relates to compounds of formula (I), wherein A is selected from 2-methylbenzo[d]oxazol-6-yl, 4-fluoro-2-methylbenzo[d]oxazol-6-yl, 6,8-dimethylimidazo[1,2-a]pyrazin-2-yl, 2-methylimidazo[1,2-a]pyridin-6-yl, 2,7-dimethylimidazo[1,2-a]pyridin-6-yl, 2,8-dimethylimidazo[1,2-a]pyridin-6-yl, 2-methyl-8-(trifluoromethyl)imidazo[1,2-a]pyridin-6-yl, 8-fluoro-2-methylimidazo[1,2-a]pyridin-6-yl, and 8-chloro-2-methylimidazo[1,2-a]pyridin-6-yl.

A particular embodiment of the present invention relates to compounds of formula (I), wherein A is selected from 8-fluoro-2-methylimidazo[1,2-a]pyridin-6-yl and 8-chloro-2-methylimidazo[1,2-a]pyridin-6-yl.

A particular embodiment of the present invention relates to compounds of formula (I), wherein each $R^5$ is independently selected from halo, $C_{1-7}$-alkyl, or $C_{1-7}$-haloalkyl.

A particular embodiment of the present invention relates to compounds of formula (I), wherein each $R^5$ is independently selected from methyl, fluoro, chloro, and trifluoromethyl.

A particular embodiment of the present invention relates to compounds of formula (I), wherein A is substituted by two $R^5$ wherein one $R^5$ is methyl and the other $R^5$ is fluoro or chloro.

A particular embodiment of the present invention relates to compounds of formula (I), wherein A is selected from the group of

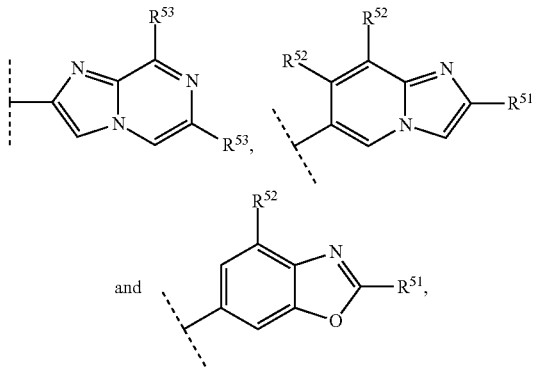

wherein $R^{51}$, $R^{52}$ and R are independently selected from the group of hydrogen, halo, cyano, $C_{1-7}$-alkyl, $C_{1-7}$-haloalkyl and $C_{3-7}$-cycloalkyl.

A particular embodiment of the present invention relates to compounds of formula (I), wherein $R^{51}$, $R^{52}$ and $R^{53}$ are independently selected from the group of hydrogen, methyl, fluoro, chloro, and trifluoromethyl.

A particular embodiment of the present invention relates to compounds of formula (I), wherein $R^{51}$ is selected from hydrogen and $C_{1-7}$-alkyl.

A more particular embodiment of the present invention relates to compounds of formula (I), wherein $R^{51}$ is selected from hydrogen and $C_{1-2}$-alkyl.

A particular embodiment of the present invention relates to compounds of formula (I), wherein each $R^{52}$ is independently selected from hydrogen, halo, cyano, $C_{1-7}$-alkyl, $C_{1-7}$-haloalkyl and $C_{3-7}$ cycloalkyl.

A particular embodiment of the present invention relates to compounds of formula (I), wherein each $R^{52}$ is independently selected from hydrogen, halo, cyano, $C_{1-2}$-alkyl, $C_{1-2}$-haloalkyl and cyclopropyl.

A particular embodiment of the present invention relates to compounds of formula (I), wherein each $R^{52}$ is independently selected from hydrogen and fluoro.

A particular embodiment of the present invention relates to compounds of formula (I), wherein each $R^{53}$ is independently selected from hydrogen, chloro, $C_{1-7}$-alkyl, $C_{1-7}$-haloalkyl and $C_{3-7}$ cycloalkyl.

A particular embodiment of the present invention relates to compounds of formula (I), wherein each $R^{53}$ is independently selected from hydrogen, chloro, $C_{1-2}$-alkyl, $C_{1-2}$-haloalkyl and cyclopropyl.

A particular embodiment of the present invention relates to compounds of formula (I), wherein B as defined herein is further characterized in that one ring nitrogen atoms is basic.

A particular embodiment of the present invention relates to compounds of formula (I), wherein B as defined herein is further characterized in that its one, two or three optional substituent(s) $R^6$ are attached at and/or directly adjacent to the basic ring nitrogen atoms.

A particular embodiment of the present invention relates to compounds of formula (I), wherein B is selected from 1,2,3,6-tetrahydropyridinyl, 2,6-diazaspiro[3.3]heptanyl, hexahydropyrrolo[3,4-c]pyrrolyl, hexahydropyrrolo[1,2-a]pyrazinyl, piperazinyl, and piperidinyl, wherein each can be optionally substituted with one, two or three $R^6$.

A particular embodiment of the present invention relates to compounds of formula (I), wherein B is selected from 1,2,3,6-tetrahydropyridin-4-yl, 2,6-diazaspiro[3.3]heptan-2-yl, hexahydropyrrolo[3,4-c]pyrrol-2-yl, hexahydropyrrolo[1,2-a]pyrazin-2-yl, piperazin-1-yl, and piperidin-4-yl, wherein each can be optionally substituted with one, two or three $R^6$.

A particular embodiment of the present invention relates to compounds of formula (I), wherein B is selected from 1,2,3,6-tetrahydropyridin-4-yl, and piperazin-1-yl, wherein each can be optionally substituted with one, two or three $R^6$.

A particular embodiment of the present invention relates to compounds of formula (I), wherein B is piperazin-1-yl optionally substituted with one, two or three $R^6$.

A particular embodiment of the present invention relates to compounds of formula (I), wherein B is selected from piperazin-1-yl, 3-methyl-piperazin-1-yl, and 3,3-dimethyl-piperazin-1-yl.

A particular embodiment of the present invention relates to compounds of formula (I), wherein each $R^6$ is $C_{1-7}$ alkyl.

A particular embodiment of the present invention relates to compounds of formula (I), wherein each $R^6$ is independently selected from methyl, and ethyl.

A particular embodiment of the present invention relates to compounds of formula (I), wherein each $R^6$ is independently selected from methyl.

A particular embodiment of the present invention relates to compounds of formula (I), wherein B is selected from the group of

[Structures showing various cyclic amine groups with R$^{61}$, R$^{62}$, R$^{63}$, R$^{64}$ substituents]

wherein R$^{61}$, R$^{62}$, R$^{63}$ and R$^{63}$ and R$^{64}$ are independently selected from hydrogen or C$_{1-7}$ alkyl, or wherein two of R$^{61}$, R$^{62}$ and R$^{63}$ together are forming a C$_{2-7}$-alkylene.

A particular embodiment of the present invention relates to compounds of formula (I), wherein R$^{61}$, R$^{62}$, R$^{63}$ and R$^{64}$ are independently selected from hydrogen, methyl, and ethyl.

A particular embodiment of the present invention relates to compounds of formula (I), wherein X is CR$^3$ and Y is CR$^4$, or X is N and Y is CR$^4$, or X is CR$^3$ and Y is N.

A particular embodiment of the present invention relates to compounds of formula (I), wherein X is CR$^3$ and Y is CR$^4$.

A particular embodiment of the present invention relates to compounds of formula (I), wherein X is N and Y is CR$^4$.

A particular embodiment of the present invention relates to compounds of formula (I), wherein X is CR$^3$ and Y is N.

A particular embodiment of the present invention relates to compounds of formula (I), wherein R$^1$ is hydrogen, halo, C$_{1-7}$-alkoxy or C$_{1-7}$-haloalkoxy.

A particular embodiment of the present invention relates to compounds of formula (I), wherein R$^1$ is hydrogen, fluoro, methoxy, ethoxy or trifluoroethoxy.

A particular embodiment of the present invention relates to compounds of formula (I), wherein R$^1$ is hydrogen.

A particular embodiment of the present invention relates to compounds of formula (I), wherein R$^2$ is hydrogen, halo, or C$_{1-7}$-alkyl.

A particular embodiment of the present invention relates to compounds of formula (I), wherein R$^2$ is hydrogen, fluoro or methyl.

A particular embodiment of the present invention relates to compounds of formula (I), wherein R$^2$ is hydrogen.

A particular embodiment of the present invention relates to compounds of formula (I), wherein R$^3$ is hydrogen or halo.

A particular embodiment of the present invention relates to compounds of formula (I), wherein R$^3$ is hydrogen or fluoro.

A particular embodiment of the present invention relates to compounds of formula (I), wherein R$^3$ is hydrogen.

A particular embodiment of the present invention relates to compounds of formula (I), wherein R$^4$ is hydrogen, halo or C$_{1-7}$-alkoxy.

A particular embodiment of the present invention relates to compounds of formula (I), wherein R$^4$ is hydrogen or halo.

A particular embodiment of the present invention relates to compounds of formula (I), wherein R$^4$ is hydrogen, fluoro, methoxy, ethoxy or trifluoroethoxy.

A particular embodiment of the present invention relates to compounds of formula (I), wherein R$^4$ is hydrogen or fluoro.

Particular compounds of formula (I) of the present invention are those selected from the group consisting of:

N-(6,8-dimethylimidazo[1,2-a]pyrazin-2-yl)-4-(piperazin-1-yl)benzamide;
rac-N-(6,8-dimethylimidazo[1,2-a]pyrazin-2-yl)-4-(3-methylpiperazin-1-yl)benzamide;
N-(6,8-Dimethyl-imidazo[1,2-a]pyrazin-2-yl)-4-((S)-3-methyl-piperazin-1-yl)-benzamide;
N-(6,8-dimethylimidazo[1,2-a]pyrazin-2-yl)-2-fluoro-4-(4-methylpiperazin-1-yl)benzamide;
rac-N-(6,8-dimethylimidazo[1,2-a]pyrazin-2-yl)-2-fluoro-4-(3-methylpiperazin-1-yl)benzamide;
N-(6,8-dimethylimidazo[1,2-a]pyrazin-2-yl)-6-(4-methylpiperazin-1-yl)nicotinamide;
rac-N-(6,8-dimethylimidazo[1,2-a]pyrazin-2-yl)-6-(3-methylpiperazin-1-yl)nicotinamide;
N-(6,8-dimethylimidazo[1,2-a]pyrazin-2-yl)-6-(4-ethylpiperazin-1-yl)nicotinamide;
N-(6,8-dimethylimidazo[1,2-a]pyrazin-2-yl)-5-(4-methylpiperazin-1-yl)picolinamide;
rac-N-(6,8-dimethylimidazo[1,2-a]pyrazin-2-yl)-5-(3-methylpiperazin-1-yl)picolinamide;
N-(6,8-dimethylimidazo[1,2-a]pyrazin-2-yl)-5-(piperazin-1-yl)picolinamide;
rac-N-(2-methylimidazo[1,2-a]pyridin-6-yl)-6-(3-methylpiperazin-1-yl)nicotinamide;
6-(3,3-dimethylpiperazin-1-yl)-N-(2-methylimidazo[1,2-a]pyridin-6-yl)nicotinamide;
N-(2-methylimidazo[1,2-a]pyridin-6-yl)-6-(piperazin-1-yl)nicotinamide;
6-hexahydropyrrolo[3,4-c]pyrrol-2(1H)-yl)-N-(2-methylimidazo[1,2-a]pyridin-6-yl)nicotinamide;
N-(2-methylimidazo[1,2-a]pyridin-6-yl)-6-(2,6-diazaspiro[3.3]heptan-2-yl)nicotinamide;
rac-N-(2-methylimidazo[1,2-a]pyridin-6-yl)-5-(3-methylpiperazin-1-yl)picolinamide;
rac-2-fluoro-N-(2-methylimidazo[1,2-a]pyridin-6-yl)-4-(3-methylpiperazin-1-yl)benzamide;
N-(2-methyl-8-(trifluoromethyl)imidazo[1,2-a]pyridin-6-yl)-6-(piperazin-1-yl)nicotinamide:
rac-N-(2-methyl-8-(trifluoromethyl)imidazo[1,2-a]pyridin-6-yl)-6-(3-methylpiperazin-1-yl)nicotinamide;

(S)-6-(hexahydropyrrolo[1,2-a]pyrazin-2(1H)-yl)-N-(2-methyl-8-(trifluoromethyl)imidazo[1,2-a]pyridin-6-yl)nicotinamide;
6-(3,5-dimethylpiperazin-1-yl)-N-(2-methyl-8-(trifluoromethyl)imidazo[1,2-a]pyridin-6-yl)nicotinamide;
6-(3,5-dimethylpiperazin-1-yl)-N-(4-fluoro-2-methylbenzo[d]oxazol-6-yl)nicotinamide;
N-(4-fluoro-2-methylbenzo[d]oxazol-6-yl)-6-(4-methylpiperazin-1-yl)nicotinamide;
(S)—N-(4-fluoro-2-methylbenzo[d]oxazol-6-yl)-6-(hexahydropyrrolo[1,2-a]pyrazin-2(1H)-yl)nicotinamide;
N-(4-Fluoro-2-methyl-benzooxazol-6-yl)-6-piperazin-1-yl-nicotinamide;
rac-N-(4-Fluoro-2-methyl-benzooxazol-6-yl)-6-(3-methyl-piperazin-1-yl)-nicotinamide;
N-(4-fluoro-2-methylbenzo[d]oxazol-6-yl)-4-(piperazin-1-yl)benzamide;
rac-N-(4-fluoro-2-methylbenzo[d]oxazol-6-yl)-4-(3-methylpiperazin-1-yl)benzamide;
4-(3,5-dimethylpiperazin-1-yl)-N-(4-fluoro-2-methylbenzo[d]oxazol-6-yl)benzamide;
(S)-2-fluoro-4-(hexahydropyrrolo[1,2-a]pyrazin-2(1H)-yl)-N-(2-methylimidazo[1,2-a]pyridin-6-yl)benzamide;
N-(8-fluoro-2-methylimidazo[1,2-a]pyridin-6-yl)-6-(4-methylpiperazin-1-yl)nicotinamide;
(S)-2-Fluoro-N-(4-fluoro-2-methyl-benzooxazol-6-yl)-4-(S)-hexahydro-pyrrolo[1,2-a]pyrazin-2-yl-benzamide;
(R)-2-fluoro-N-(4-fluoro-2-methylbenzo[d]oxazol-6-yl)-4-(hexahydropyrrolo[1,2-a]pyrazin-2(1H)-yl)benzamide;
(S)-2-fluoro-4-(hexahydropyrrolo[1,2-a]pyrazin-2(1H)-yl)-N-(2-methyl-8-(trifluoromethyl)imidazo[1,2-a]pyridin-6-yl)benzamide;
N-(8-fluoro-2-methylimidazo[1,2-a]pyridin-6-yl)-4-(piperazin-1-yl)benzamide;
rac-N-(2,8-dimethylimidazo[1,2-a]pyridin-6-yl)-2-fluoro-4-(3-methylpiperazin-1-yl)benzamide;
rac-2-fluoro-N-(2-methylbenzo[d]oxazol-6-yl)-4-(3-methylpiperazin-1-yl)benzamide;
rac-2-fluoro-N-(8-fluoro-2-methylimidazo[1,2-a]pyridin-6-yl)-4-(3-methylpiperazin-1-yl)benzamide;
2-fluoro-N-(8-fluoro-2-methylimidazo[1,2-a]pyridin-6-yl)-4-(piperazin-1-yl)benzamide;
N-(8-fluoro-2-methylimidazo[1,2-a]pyridin-6-yl)-6-(piperazin-1-yl)nicotinamide;
rac-N-(8-fluoro-2-methylimidazo[1,2-a]pyridin-6-yl)-6-(3-methylpiperazin-1-yl)nicotinamide;
rac-N-(8-fluoro-2-methylimidazo[1,2-a]pyridin-6-yl)-5-(3-methylpiperazin-1-yl)picolinamide;
2-fluoro-N-(2-methylimidazo[1,2-a]pyridin-6-yl)-4-(piperazin-1-yl)benzamide;
rac-2,3-difluoro-N-(8-fluoro-2-methylimidazo[1,2-a]pyridin-6-yl)-4-(3-methylpiperazin-1-yl)benzamide;
rac-2,5-difluoro-N-(8-fluoro-2-methylimidazo[1,2-a]pyridin-6-yl)-4-(3-methylpiperazin-1-yl)benzamide;
rac-5-fluoro-N-(8-fluoro-2-methylimidazo[1,2-a]pyridin-6-yl)-6-(3-methylpiperazin-1-yl)nicotinamide;
rac-3-fluoro-N-(8-fluoro-2-methylimidazo[1,2-a]pyridin-6-yl)-5-(3-methylpiperazin-1-yl)picolinamide;
rac-2,6-difluoro-N-(8-fluoro-2-methylimidazo[1,2-a]pyridin-6-yl)-4-(3-methylpiperazin-1-yl)benzamide;
(S)-2-fluoro-N-(8-fluoro-2-methylimidazo[1,2-a]pyridin-6-yl)-4-(3-methylpiperazin-1-yl)benzamide;
(R)-2-fluoro-N-(8-fluoro-2-methylimidazo[1,2-a]pyridin-6-yl)-4-(3-methylpiperazin-1-yl)benzamide;
rac-N-(2,7-dimethylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-5-fluoro-6-(3-methylpiperazin-1-yl)nicotinamide;
rac-N-(8-chloro-2-methylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-6-(3-methylpiperazin-1-yl)nicotinamide;
rac-N-(8-chloro-2-methylimidazo[1,2-a]pyridin-6-yl)-3-fluoro-5-(3-methylpiperazin-1-yl)picolinamide;
rac-N-(8-chloro-2-methylimidazo[1,2-a]pyridin-6-yl)-2,6-difluoro-4-(3-methylpiperazin-1-yl)benzamide;
2-fluoro-N-(4-fluoro-2-methylbenzo[d]oxazol-6-yl)-4-(piperazin-1-yl)benzamide;
2-fluoro-N-(2-methyl-8-(trifluoromethyl)imidazo[1,2-a]pyridin-6-yl)-4-(piperazin-1-yl)benzamide;
2-fluoro-N-(2-methylimidazo[1,2-a]pyridin-6-yl)-4-(1,2,3,6-tetrahydropyridin-4-yl)benzamide;
2-fluoro-N-(8-fluoro-2-methylimidazo[1,2-a]pyridin-6-yl)-4-(1,2,3,6-tetrahydropyridin-4-yl)benzamide;
N-(8-fluoro-2-methylimidazo[1,2-a]pyridin-6-yl)-6-(1,2,3,6-tetrahydropyridin-4-yl)nicotinamide;
N-(2-methylimidazo[1,2-a]pyridin-6-yl)-5-(1,2,3,6-tetrahydropyridin-4-yl)picolinamide;
N-(8-fluoro-2-methylimidazo[1,2-a]pyridin-6-yl)-2-methoxy-6-(piperazin-1-yl)nicotinamide;
2-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-3-methyl-4-(piperazin-1-yl)benzamide;
N-(8-fluoro-2-methylimidazo[1,2-a]pyridin-6-yl)-5-methyl-6-(piperazin-1-yl)nicotinamide;
4-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-4-methoxy-6-(piperazin-1-yl)nicotinamide;
4-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-4-(2,2,2-trifluoroethoxy)nicotinamide;
2-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-2-(2,2,2-trifluoroethoxy)nicotinamide;
rac-N-(8-fluoro-2-methylimidazo[1,2-a]pyridin-6-yl)-2-methoxy-6-(3-methylpiperazin-1-yl)nicotinamide;
6-(3,3-dimethylpiperazin-1-yl)-N-(8-fluoro-2-methylimidazo[1,2-a]pyridin-6-yl)-2-methoxynicotinamide;
rac-N-(8-fluoro-2-methylimidazo[1,2-a]pyridin-6-yl)-4-methoxy-6-(3-methylpiperazin-1-yl)nicotinamide;
N-(2-methylimidazo[1,2-a]pyridin-6-yl)-6-(1,2,3,6-tetrahydropyridin-4-yl)nicotinamide;
N-(2-methylimidazo[1,2-a]pyridin-6-yl)-6-(1-methylpiperidin-4-yl)nicotinamide;
N-(8-fluoro-2-methylimidazo[1,2-a]pyridin-6-yl)-6-(piperidin-4-yl)nicotinamide;
N-(8-fluoro-2-methylimidazo[1,2-a]pyridin-6-yl)-6-(1-methylpiperidin-4-yl)nicotinamide;
2-fluoro-N-(8-fluoro-2-methylimidazo[1,2-a]pyridin-6-yl)-4-(piperidin-4-yl)benzamide;
rac-6-(3,4-dimethylpiperazin-1-yl)-N-(2-methylimidazo[1,2-a]pyridin-6-yl)nicotinamide;
and pharmaceutically acceptable salts thereof.

Particular compounds of formula (I) of the present invention are those selected from the group consisting of:
N-(6,8-dimethylimidazo[1,2-a]pyrazin-2-yl)-4-(piperazin-1-yl)benzamide;
rac-N-(6,8-dimethylimidazo[1,2-a]pyrazin-2-yl)-4-(3-methylpiperazin-1-yl)benzamide;

N-(6,8-Dimethyl-imidazo[1,2-a]pyrazin-2-yl)-4-((S)-3-methyl-piperazin-1-yl)-benzamide;
N-(6,8-dimethylimidazo[1,2-a]pyrazin-2-yl)-2-fluoro-4-(4-methylpiperazin-1-yl)benzamide;
rac-N-(6,8-dimethylimidazo[1,2-a]pyrazin-2-yl)-2-fluoro-4-(3-methylpiperazin-1-yl)benzamide;
N-(6,8-dimethylimidazo[1,2-a]pyrazin-2-yl)-6-(4-methyl-piperazin-1-yl)nicotinamide;
rac-N-(6,8-dimethylimidazo[1,2-a]pyrazin-2-yl)-6-(3-methylpiperazin-1-yl)nicotinamide;
N-(6,8-dimethylimidazo[1,2-a]pyrazin-2-yl)-6-(4-ethylpiperazin-1-yl)nicotinamide;
N-(6,8-dimethylimidazo[1,2-a]pyrazin-2-yl)-5-(4-methylpiperazin-1-yl)picolinamide;
rac-N-(6,8-dimethylimidazo[1,2-a]pyrazin-2-yl)-5-(3-methylpiperazin-1-yl)picolinamide;
N-(6,8-dimethylimidazo[1,2-a]pyrazin-2-yl)-5-(piperazin-1-yl)picolinamide;
rac-N-(2-methylimidazo[1,2-a]pyridin-6-yl)-6-(3-methylpiperazin-1-yl)nicotinamide;
6-(3,3-dimethylpiperazin-1-yl)-N-(2-methylimidazo[1,2-a]pyridin-6-yl)nicotinamide;
N-(2-methylimidazo[1,2-a]pyridin-6-yl)-6-(piperazin-1-yl)nicotinamide;
6-hexahydropyrrolo[3,4-c]pyrrol-2(1H)-yl)-N-(2-methyl-imidazo[1,2-a]pyridin-6-yl)nicotinamide hydrochloride;
N-(2-methylimidazo[1,2-a]pyridin-6-yl)-6-(2,6-diazaspiro[3.3]heptan-2-yl)nicotinamide hydrochloride:
rac-N-(2-methylimidazo[1,2-a]pyridin-6-yl)-5-(3-methylpiperazin-1-yl)picolinamide;
rac-2-fluoro-N-(2-methylimidazo[1,2-a]pyridin-6-yl)-4-(3-methylpiperazin-1-yl)benzamide;
N-(2-methyl-8-(trifluoromethyl)imidazo[1,2-a]pyridin-6-yl)-6-(piperazin-1-yl)nicotinamide:
rac-N-(2-methyl-8-(trifluoromethyl)imidazo[1,2-a]pyridin-6-yl)-6-(3-methylpiperazin-1-yl)nicotinamide;
(S)-6-(hexahydropyrrolo[1,2-a]pyrazin-2(1H)-yl)-N-(2-methyl-8-(trifluoromethyl)imidazo[1,2-a]pyridin-6-yl)nicotinamide;
6-(3,5-dimethylpiperazin-1-yl)-N-(2-methyl-8-(trifluoromethyl)imidazo[1,2-a]pyridin-6-yl)nicotinamide;
6-(3,5-dimethylpiperazin-1-yl)-N-(4-fluoro-2-methylbenzo[d]oxazol-6-yl)nicotinamide;
N-(4-fluoro-2-methylbenzo[d]oxazol-6-yl)-6-(4-methylpiperazin-1-yl)nicotinamide;
(S)—N-(4-fluoro-2-methylbenzo[d]oxazol-6-yl)-6-(hexahydropyrrolo[1,2-a]pyrazin-2(1H)-yl)nicotinamide;
N-(4-Fluoro-2-methyl-benzooxazol-6-yl)-6-piperazin-1-yl-nicotinamide;
rac-N-(4-Fluoro-2-methyl-benzooxazol-6-yl)-6-(3-methyl-piperazin-1-yl)-nicotinamide;
N-(4-fluoro-2-methylbenzo[d]oxazol-6-yl)-4-(piperazin-1-yl)benzamide;
rac-N-(4-fluoro-2-methylbenzo[d]oxazol-6-yl)-4-(3-methylpiperazin-1-yl)benzamide;
4-(3,5-dimethylpiperazin-1-yl)-N-(4-fluoro-2-methylbenzo[d]oxazol-6-yl)benzamide;
(S)-2-fluoro-4-(hexahydropyrrolo[1,2-a]pyrazin-2(1H)-yl)-N-(2-methylimidazo[1,2-a]pyridin-6-yl)benzamide;
N-(8-fluoro-2-methylimidazo[1,2-a]pyridin-6-yl)-6-(4-methylpiperazin-1-yl)nicotinamide;
(S)-2-Fluoro-N-(4-fluoro-2-methyl-benzooxazol-6-yl)-4-(S)-hexahydro-pyrrolo[1,2-a]pyrazin-2-yl-benzamide;
(R)-2-fluoro-N-(4-fluoro-2-methylbenzo[d]oxazol-6-yl)-4-(hexahydropyrrolo[1,2-a]pyrazin-2(1H)-yl)benzamide;
(S)-2-fluoro-4-(hexahydropyrrolo[1,2-a]pyrazin-2(1H)-yl)-N-(2-methyl-8-(trifluoromethyl)imidazo[1,2-a]pyridin-6-yl)benzamide;
N-(8-fluoro-2-methylimidazo[1,2-a]pyridin-6-yl)-4-(piperazin-1-yl)benzamide hydrochloride;
rac-N-(2,8-dimethylimidazo[1,2-a]pyridin-6-yl)-2-fluoro-4-(3-methylpiperazin-1-yl)benzamide dihydrochloride;
rac-2-fluoro-N-(2-methylbenzo[d]oxazol-6-yl)-4-(3-methylpiperazin-1-yl)benzamide dihydrochloride;
rac-2-fluoro-N-(8-fluoro-2-methylimidazo[1,2-a]pyridin-6-yl)-4-(3-methylpiperazin-1-yl)benzamide dihydrochloride;
2-fluoro-N-(8-fluoro-2-methylimidazo[1,2-a]pyridin-6-yl)-4-(piperazin-1-yl)benzamide dihydrochloride;
N-(8-fluoro-2-methylimidazo[1,2-a]pyridin-6-yl)-6-(piperazin-1-yl)nicotinamide dihydrochloride;
rac-N-(8-fluoro-2-methylimidazo[1,2-a]pyridin-6-yl)-6-(3-methylpiperazin-1-yl)nicotinamide dihydrochloride;
rac-N-(8-fluoro-2-methylimidazo[1,2-a]pyridin-6-yl)-5-(3-methylpiperazin-1-yl)picolinamide dihydrochloride;
2-fluoro-N-(2-methylimidazo[1,2-a]pyridin-6-yl)-4-(piperazin-1-yl)benzamide hydrochloride;
rac-2,3-difluoro-N-(8-fluoro-2-methylimidazo[1,2-a]pyridin-6-yl)-4-(3-methylpiperazin-1-yl)benzamide hydrochloride;
rac-2,5-difluoro-N-(8-fluoro-2-methylimidazo[1,2-a]pyridin-6-yl)-4-(3-methylpiperazin-1-yl)benzamide hydrochloride;
rac-5-fluoro-N-(8-fluoro-2-methylimidazo[1,2-a]pyridin-6-yl)-6-(3-methylpiperazin-1-yl)nicotinamide hydrochloride;
rac-3-fluoro-N-(8-fluoro-2-methylimidazo[1,2-a]pyridin-6-yl)-5-(3-methylpiperazin-1-yl)picolinamide hydrochloride;
rac-2,6-difluoro-N-(8-fluoro-2-methylimidazo[1,2-a]pyridin-6-yl)-4-(3-methylpiperazin-1-yl)benzamide hydrochloride;
(S)-2-fluoro-N-(8-fluoro-2-methylimidazo[1,2-a]pyridin-6-yl)-4-(3-methylpiperazin-1-yl)benzamide hydrochloride;
(R)-2-fluoro-N-(8-fluoro-2-methylimidazo[1,2-a]pyridin-6-yl)-4-(3-methylpiperazin-1-yl)benzamide hydrochloride;
rac-N-(2,7-dimethylimidazo[1,2-a]pyridin-6-yl)-2-fluoro-4-(3-methylpiperazin-1-yl)benzamide dihydrochloride;
rac-N-(8-chloro-2-methylimidazo[1,2-a]pyridin-6-yl)-5-fluoro-6-(3-methylpiperazin-1-yl)nicotinamide hydrochloride;
rac-N-(8-chloro-2-methylimidazo[1,2-a]pyridin-6-yl)-2-fluoro-4-(3-methylpiperazin-1-yl)benzamide dihydrochloride;
rac-N-(8-chloro-2-methylimidazo[1,2-a]pyridin-6-yl)-6-(3-methylpiperazin-1-yl)nicotinamide dihydrochloride;
rac-N-(8-chloro-2-methylimidazo[1,2-a]pyridin-6-yl)-3-fluoro-5-(3-methylpiperazin-1-yl)picolinamide dihydrochloride;
rac-N-(8-chloro-2-methylimidazo[1,2-a]pyridin-6-yl)-2,6-difluoro-4-(3-methylpiperazin-1-yl)benzamide trihydrochloride;
2-fluoro-N-(4-fluoro-2-methylbenzo[d]oxazol-6-yl)-4-(piperazin-1-yl)benzamide;
2-fluoro-N-(2-methyl-8-(trifluoromethyl)imidazo[1,2-a]pyridin-6-yl)-4-(piperazin-1-yl)benzamide;
2-fluoro-N-(2-methylimidazo[1,2-a]pyridin-6-yl)-4-(1,2,3,6-tetrahydropyridin-4-yl)benzamide hydrochloride;
2-fluoro-N-(8-fluoro-2-methylimidazo[1,2-a]pyridin-6-yl)-4-(1,2,3,6-tetrahydropyridin-4-yl)benzamide hydrochloride;

N-(8-fluoro-2-methylimidazo[1,2-a]pyridin-6-yl)-6-(1,2,3,6-tetrahydropyridin-4-yl)nicotinamide dihydrochloride;
N-(2-methylimidazo[1,2-a]pyridin-6-yl)-5-(1,2,3,6-tetrahydropyridin-4-yl)picolinamide dihydrochloride;
N-(8-fluoro-2-methylimidazo[1,2-a]pyridin-6-yl)-2-methoxy-6-(piperazin-1-yl)nicotinamide;
2-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-3-methyl-4-(piperazin-1-yl)benzamide;
N-(8-fluoro-2-methylimidazo[1,2-a]pyridin-6-yl)-5-methyl-6-(piperazin-1-yl)nicotinamide;
4-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-4-methoxy-6-(piperazin-1-yl)nicotinamide;
4-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-4-(2,2,2-trifluoroethoxy)nicotinamide;
2-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-2-(2,2,2-trifluoroethoxy)nicotinamide;
rac-N-(8-fluoro-2-methylimidazo[1,2-a]pyridin-6-yl)-2-methoxy-6-(3-methylpiperazin-1-yl)nicotinamide;
6-(3,3-dimethylpiperazin-1-yl)-N-(8-fluoro-2-methylimidazo[1,2-a]pyridin-6-yl)-2-methoxynicotinamide;
rac-N-(8-fluoro-2-methylimidazo[1,2-a]pyridin-6-yl)-4-methoxy-6-(3-methylpiperazin-1-yl)nicotinamide;
N-(2-methylimidazo[1,2-a]pyridin-6-yl)-6-(1,2,3,6-tetrahydropyridin-4-yl)nicotinamide hydrochloride;
N-(2-methylimidazo[1,2-a]pyridin-6-yl)-6-(1-methylpiperidin-4-yl)nicotinamide;
N-(8-fluoro-2-methylimidazo[1,2-a]pyridin-6-yl)-6-(piperidin-4-yl)nicotinamide dihydrochloride;
N-(8-fluoro-2-methylimidazo[1,2-a]pyridin-6-yl)-6-(1-methylpiperidin-4-yl)nicotinamide;
2-fluoro-N-(8-fluoro-2-methylimidazo[1,2-a]pyridin-6-yl)-4-(piperidin-4-yl)benzamide hydrochloride;
rac-6-(3,4-dimethylpiperazin-1-yl)-N-(2-methylimidazo[1,2-a]pyridin-6-yl)nicotinamide;
and pharmaceutically acceptable salts thereof.

Particular compounds of formula (I) of the present invention are those selected from the group consisting of:
rac-2-fluoro-N-(8-fluoro-2-methylimidazo[1,2-a]pyridin-6-yl)-4-(3-methylpiperazin-1-yl)benzamide;
2-fluoro-N-(8-fluoro-2-methylimidazo[1,2-a]pyridin-6-yl)-4-(piperazin-1-yl)benzamide;
N-(8-fluoro-2-methylimidazo[1,2-a]pyridin-6-yl)-6-(piperazin-1-yl)nicotinamide;
rac-3-fluoro-N-(8-fluoro-2-methylimidazo[1,2-a]pyridin-6-yl)-5-(3-methylpiperazin-1-yl)picolinamide;
rac-2,6-difluoro-N-(8-fluoro-2-methylimidazo[1,2-a]pyridin-6-yl)-4-(3-methylpiperazin-1-yl)benzamide;
(S)-2-fluoro-N-(8-fluoro-2-methylimidazo[1,2-a]pyridin-6-yl)-4-(3-methylpiperazin-1-yl)benzamide;
(R)-2-fluoro-N-(8-fluoro-2-methylimidazo[1,2-a]pyridin-6-yl)-4-(3-methylpiperazin-1-yl)benzamide;
rac-N-(8-chloro-2-methylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-3-fluoro-5-(3-methylpiperazin-1-yl)picolinamide;
2-fluoro-N-(8-fluoro-2-methylimidazo[1,2-a]pyridin-6-yl)-4-(1,2,3,6-tetrahydropyridin-4-yl)benzamide;
N-(8-fluoro-2-methylimidazo[1,2-a]pyridin-6-yl)-6-(1,2,3,6-tetrahydropyridin-4-yl)nicotinamide;
4-fluoro-N-(8-fluoro-2-methylimidazo[1,2-a]pyridin-6-yl)-6-(piperazin-1-yl)nicotinamide;
4-ethoxy-N-(8-fluoro-2-methylimidazo[1,2-a]pyridin-6-yl)-6-(piperazin-1-yl)nicotinamide;
2-ethoxy-N-(8-fluoro-2-methylimidazo[1,2-a]pyridin-6-yl)-6-(piperazin-1l-yl)nicotinamide;
rac-N-(8-fluoro-2-methylimidazo[1,2-a]pyridin-6-yl)-2-methoxy-6-(3-methylpiperazin-1-yl)nicotinamide;
rac-N-(8-fluoro-2-methylimidazo[1,2-a]pyridin-6-yl)-4-methoxy-6-(3-methylpiperazin-1-yl)nicotinamide;
and pharmaceutically acceptable salts thereof.

A particular embodiment of the present invention relates to compounds of formula (I')

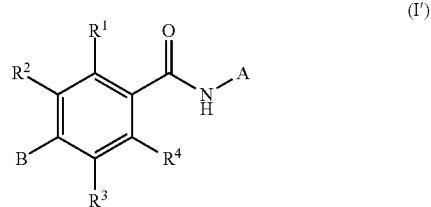

wherein A, B, R¹, R², R³ and R⁴ are as described herein.
Particular compounds of formula (I') of the present invention are those selected from the group consisting of:
N-(6,8-dimethylimidazo[1,2-a]pyrazin-2-yl)-4-(piperazin-1-yl)benzamide;
rac-N-(6,8-dimethylimidazo[1,2-a]pyrazin-2-yl)-4-(3-methylpiperazin-1-yl)benzamide;
N-(6,8-Dimethyl-imidazo[1,2-a]pyrazin-2-yl)-4-((S)-3-methyl-piperazin-1-yl)-benzamide;
N-(6,8-dimethylimidazo[1,2-a]pyrazin-2-yl)-2-fluoro-4-(4-methylpiperazin-1-yl)benzamide;
rac-N-(6,8-dimethylimidazo[1,2-a]pyrazin-2-yl)-2-fluoro-4-(3-methylpiperazin-1-yl)benzamide;
rac-2-fluoro-N-(2-methylimidazo[1,2-a]pyridin-6-yl)-4-(3-methylpiperazin-1-yl)benzamide;
N-(4-fluoro-2-methylbenzo[d]oxazol-6-yl)-4-(piperazin-1-yl)benzamide;
rac-N-(4-fluoro-2-methylbenzo[d]oxazol-6-yl)-4-(3-methylpiperazin-1-yl)benzamide;
4-(3,5-dimethylpiperazin-1-yl)-N-(4-fluoro-2-methylbenzo[d]oxazol-6-yl)benzamide;
(S)-2-fluoro-4-(hexahydropyrrolo[1,2-a]pyrazin-2(1H)-yl)-N-(2-methylimidazo[1,2-a]pyridin-6-yl)benzamide;
(S)-2-Fluoro-N-(4-fluoro-2-methyl-benzooxazol-6-yl)-4-(S)-hexahydro-pyrrolo[1,2-a]pyrazin-2-yl-benzamide;
(R)-2-fluoro-N-(4-fluoro-2-methylbenzo[d]oxazol-6-yl)-4-(hexahydropyrrolo[1,2-a]pyrazin-2(1H)-yl)benzamide;
(S)-2-fluoro-4-(hexahydropyrrolo[1,2-a]pyrazin-2(1H)-yl)-N-(2-methyl-8-(trifluoromethyl)imidazo[1,2-a]pyridin-6-yl)benzamide;
N-(8-fluoro-2-methylimidazo[1,2-a]pyridin-6-yl)-4-(piperazin-1-yl)benzamide;
rac-N-(2,8-dimethylimidazo[1,2-a]pyridin-6-yl)-2-fluoro-4-(3-methylpiperazin-1-yl)benzamide;
rac-2-fluoro-N-(2-methylbenzo[d]oxazol-6-yl)-4-(3-methylpiperazin-1-yl)benzamide;
rac-2-fluoro-N-(8-fluoro-2-methylimidazo[1,2-a]pyridin-6-yl)-4-(3-methylpiperazin-1-yl)benzamide;
2-fluoro-N-(8-fluoro-2-methylimidazo[1,2-a]pyridin-6-yl)-4-(piperazin-1-yl)benzamide;
2-fluoro-N-(2-methylimidazo[1,2-a]pyridin-6-yl)-4-(piperazin-1-yl)benzamide;

rac-2,3-difluoro-N-(8-fluoro-2-methylimidazo[1,2-a]pyridin-6-yl)-4-(3-methylpiperazin-1-yl)benzamide;
rac-2,5-difluoro-N-(8-fluoro-2-methylimidazo[1,2-a]pyridin-6-yl)-4-(3-methylpiperazin-1-yl)benzamide;
rac-2,6-difluoro-N-(8-fluoro-2-methylimidazo[1,2-a]pyridin-6-yl)-4-(3-methylpiperazin-1-yl)benzamide;
(S)-2-fluoro-N-(8-fluoro-2-methylimidazo[1,2-a]pyridin-6-yl)-4-(3-methylpiperazin-1-yl)benzamide;
(R)-2-fluoro-N-(8-fluoro-2-methylimidazo[1,2-a]pyridin-6-yl)-4-(3-methylpiperazin-1-yl)benzamide;
rac-N-(2,7-dimethylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-2,6-difluoro-4-(3-methylpiperazin-1-yl)benzamide;
2-fluoro-N-(4-fluoro-2-methylbenzo[d]oxazol-6-yl)-4-(piperazin-1-yl)benzamide;
2-fluoro-N-(2-methyl-8-(trifluoromethyl)imidazo[1,2-a]pyridin-6-yl)-4-(piperazin-1-yl)benzamide;
2-fluoro-N-(2-methylimidazo[1,2-a]pyridin-6-yl)-4-(1,2,3,6-tetrahydropyridin-4-yl)benzamide;
2-fluoro-N-(8-fluoro-2-methylimidazo[1,2-a]pyridin-6-yl)-4-(1,2,3,6-tetrahydropyridin-4-yl)benzamide;
N-(8-fluoro-2-methylimidazo[1,2-a]pyridin-6-yl)-3-methyl-4-(piperazin-1-yl)benzamide;
2-fluoro-N-(8-fluoro-2-methylimidazo[1,2-a]pyridin-6-yl)-4-(piperidin-4-yl)benzamide;
and pharmaceutically acceptable salts thereof.

A particular embodiment of the present invention relates to compounds of formula (I″)

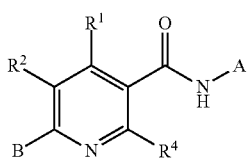

(I″)

wherein A, B, $R^1$, $R^2$ and $R^4$ are as described herein.

Particular compounds of formula (I″) of the present invention are those selected from the group consisting of:
N-(6,8-dimethylimidazo[1,2-a]pyrazin-2-yl)-6-(4-methylpiperazin-1-yl)nicotinamide;
rac-N-(6,8-dimethylimidazo[1,2-a]pyrazin-2-yl)-6-(3-methylpiperazin-1-yl)nicotinamide;
N-(6,8-dimethylimidazo[1,2-a]pyrazin-2-yl)-6-(4-ethylpiperazin-1-yl)nicotinamide;
rac-N-(2-methylimidazo[1,2-a]pyridin-6-yl)-6-(3-methylpiperazin-1-yl)nicotinamide;
6-(3,3-dimethylpiperazin-1-yl)-N-(2-methylimidazo[1,2-a]pyridin-6-yl)nicotinamide;
N-(2-methylimidazo[1,2-a]pyridin-6-yl)-6-(piperazin-1-yl)nicotinamide;
6-hexahydropyrrolo[3,4-c]pyrrol-2(1H)-yl)-N-(2-methylimidazo[1,2-a]pyridin-6-yl)nicotinamide;
N-(2-methylimidazo[1,2-a]pyridin-6-yl)-6-(2,6-diazaspiro[3.3]heptan-2-yl)nicotinamide;
N-(2-methyl-8-(trifluoromethyl)imidazo[1,2-a]pyridin-6-yl)-6-(piperazin-1-yl)nicotinamide;
rac-N-(2-methyl-8-(trifluoromethyl)imidazo[1,2-a]pyridin-6-yl)-6-(3-methylpiperazin-1-yl)nicotinamide;
(S)-6-(hexahydropyrrolo[1,2-a]pyrazin-2(1H)-yl)-N-(2-methyl-8-(trifluoromethyl)imidazo[1,2-a]pyridin-6-yl)nicotinamide;
6-(3,5-dimethylpiperazin-1-yl)-N-(2-methyl-8-(trifluoromethyl)imidazo[1,2-a]pyridin-6-yl)nicotinamide;
6-(3,5-dimethylpiperazin-1-yl)-N-(4-fluoro-2-methylbenzo[d]oxazol-6-yl)nicotinamide;
N-(4-fluoro-2-methylbenzo[d]oxazol-6-yl)-6-(4-methylpiperazin-1-yl)nicotinamide;
(S)—N-(4-fluoro-2-methylbenzo[d]oxazol-6-yl)-6-(hexahydropyrrolo[1,2-a]pyrazin-2(1H)-yl)nicotinamide;
N-(4-Fluoro-2-methyl-benzooxazol-6-yl)-6-piperazin-1-yl-nicotinamide;
rac-N-(4-Fluoro-2-methyl-benzooxazol-6-yl)-6-(3-methyl-piperazin-1-yl)-nicotinamide;
N-(8-fluoro-2-methylimidazo[1,2-a]pyridin-6-yl)-6-(4-methylpiperazin-1-yl)nicotinamide;
N-(8-fluoro-2-methylimidazo[1,2-a]pyridin-6-yl)-6-(piperazin-1-yl)nicotinamide;
rac-N-(8-fluoro-2-methylimidazo[1,2-a]pyridin-6-yl)-6-(3-methylpiperazin-1-yl)nicotinamide;
rac-5-fluoro-N-(8-fluoro-2-methylimidazo[1,2-a]pyridin-6-yl)-6-(3-methylpiperazin-1-yl)nicotinamide;
rac-N-(8-chloro-2-methylimidazo[1,2-a]pyridin-6-yl)-5-fluoro-6-(3-methylpiperazin-1-yl)nicotinamide;
rac-N-(8-chloro-2-methylimidazo[1,2-a]pyridin-6-yl)-6-(3-methylpiperazin-1-yl)nicotinamide;
N-(8-fluoro-2-methylimidazo[1,2-a]pyridin-6-yl)-6-(1,2,3,6-tetrahydropyridin-4-yl)nicotinamide;
N-(8-fluoro-2-methylimidazo[1,2-a]pyridin-6-yl)-2-methoxy-6-(piperazin-1-yl)nicotinamide;
2-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-5-methyl-6-(piperazin-1-yl)nicotinamide;
4-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-4-methoxy-6-(piperazin-1-yl)nicotinamide;
4-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-4-(2,2,2-trifluoroethoxy)nicotinamide;
2-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-2-(2,2,2-trifluoroethoxy)nicotinamide;
rac-N-(8-fluoro-2-methylimidazo[1,2-a]pyridin-6-yl)-2-methoxy-6-(3-methylpiperazin-1-yl)nicotinamide;
6-(3,3-dimethylpiperazin-1-yl)-N-(8-fluoro-2-methylimidazo[1,2-a]pyridin-6-yl)-2-methoxynicotinamide;
rac-N-(8-fluoro-2-methylimidazo[1,2-a]pyridin-6-yl)-4-methoxy-6-(3-methylpiperazin-1-yl)nicotinamide;
N-(2-methylimidazo[1,2-a]pyridin-6-yl)-6-(1,2,3,6-tetrahydropyridin-4-yl)nicotinamide;
N-(2-methylimidazo[1,2-a]pyridin-6-yl)-6-(1-methylpiperidin-4-yl)nicotinamide;
N-(8-fluoro-2-methylimidazo[1,2-a]pyridin-6-yl)-6-(piperidin-4-yl)nicotinamide;
N-(8-fluoro-2-methylimidazo[1,2-a]pyridin-6-yl)-6-(1-methylpiperidin-4-yl)nicotinamide;
rac-6-(3,4-dimethylpiperazin-1-yl)-N-(2-methylimidazo[1,2-a]pyridin-6-yl)nicotinamide;
and pharmaceutically acceptable salts thereof.

A particular embodiment of the present invention relates to compounds of formula (I‴)

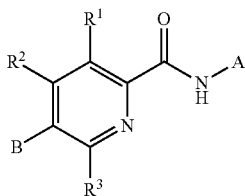

wherein A, B, $R^1$, $R^2$ and $R^3$ are as described herein.

Particular compounds of formula (I''') of the present invention are those selected from the group consisting of:

N-(6,8-dimethylimidazo[1,2-a]pyrazin-2-yl)-5-(4-methyl-piperazin-1-yl)picolinamide;
rac-N-(6,8-dimethylimidazo[1,2-a]pyrazin-2-yl)-5-(3-methylpiperazin-1-yl)picolinamide;
N-(6,8-dimethylimidazo[1,2-a]pyrazin-2-yl)-5-(piperazin-1-yl)picolinamide;
rac-N-(2-methylimidazo[1,2-a]pyridin-6-yl)-5-(3-methylpiperazin-1-yl)picolinamide;
rac-N-(8-fluoro-2-methylimidazo[1,2-a]pyridin-6-yl)-5-(3-methylpiperazin-1-yl)picolinamide;
rac-3-fluoro-N-(8-fluoro-2-methylimidazo[1,2-a]pyridin-6-yl)-5-(3-methylpiperazin-1-yl)picolinamide;
rac-N-(8-chloro-2-methylimidazo[1,2-a]pyridin-6-yl)-3-fluoro-5-(3-methylpiperazin-1-yl)picolinamide;
N-(2-methylimidazo[1,2-a]pyridin-6-yl)-5-(1,2,3,6-tetrahydropyridin-4-yl)picolinamide;
and pharmaceutically acceptable salts thereof.

A particular embodiment of the present invention relates to compounds of formula (I$^a$)

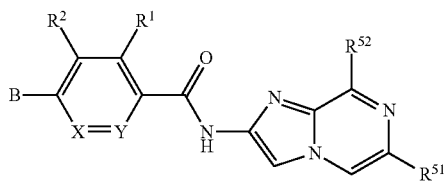

wherein B, X, Y, $R^1$, $R^2$, $R^{51}$ and $R^{52}$ are as described herein.

Particular compounds of formula (I$^a$) of the present invention are those selected from the group consisting of:
N-(6,8-dimethylimidazo[1,2-a]pyrazin-2-yl)-4-(piperazin-1-yl)benzamide;
rac-N-(6,8-dimethylimidazo[1,2-a]pyrazin-2-yl)-4-(3-methylpiperazin-1-yl)benzamide;
N-(6,8-Dimethyl-imidazo[1,2-a]pyrazin-2-yl)-4-((S)-3-methyl-piperazin-1-yl)-benzamide;
N-(6,8-dimethylimidazo[1,2-a]pyrazin-2-yl)-2-fluoro-4-(4-methylpiperazin-1-yl)benzamide;
rac-N-(6,8-dimethylimidazo[1,2-a]pyrazin-2-yl)-2-fluoro-4-(3-methylpiperazin-1-yl)benzamide;
N-(6,8-dimethylimidazo[1,2-a]pyrazin-2-yl)-6-(4-methylpiperazin-1-yl)nicotinamide;
rac-N-(6,8-dimethylimidazo[1,2-a]pyrazin-2-yl)-6-(3-methylpiperazin-1-yl)nicotinamide;
N-(6,8-dimethylimidazo[1,2-a]pyrazin-2-yl)-6-(4-ethylpiperazin-1-yl)nicotinamide;
N-(6,8-dimethylimidazo[1,2-a]pyrazin-2-yl)-5-(4-methylpiperazin-1-yl)picolinamide;
rac-N-(6,8-dimethylimidazo[1,2-a]pyrazin-2-yl)-5-(3-methylpiperazin-1-yl)picolinamide;
N-(6,8-dimethylimidazo[1,2-a]pyrazin-2-yl)-5-(piperazin-1-yl)picolinamide;
and pharmaceutically acceptable salts thereof.

A particular embodiment of the present invention relates to compounds of formula (I$^b$)

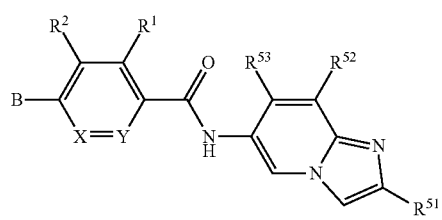

wherein B, X, Y, $R^1$, $R^2$, $R^{51}$, $R^{52}$ and $R^{53}$ are as described herein.

Particular compounds of formula (I$^b$) of the present invention are those selected from the group consisting of:
rac-N-(2-methylimidazo[1,2-a]pyridin-6-yl)-6-(3-methylpiperazin-1-yl)nicotinamide;
6-(3,3-dimethylpiperazin-1-yl)-N-(2-methylimidazo[1,2-a]pyridin-6-yl)nicotinamide;
N-(2-methylimidazo[1,2-a]pyridin-6-yl)-6-(piperazin-1-yl)nicotinamide;
6-hexahydropyrrolo[3,4-c]pyrrol-2(1H)-yl)-N-(2-methylimidazo[1,2-a]pyridin-6-yl)nicotinamide;
N-(2-methylimidazo[1,2-a]pyridin-6-yl)-6-(2,6-diazaspiro[3.3]heptan-2-yl)nicotinamide;
rac-N-(2-methylimidazo[1,2-a]pyridin-6-yl)-5-(3-methylpiperazin-1-yl)picolinamide;
rac-2-fluoro-N-(2-methylimidazo[1,2-a]pyridin-6-yl)-4-(3-methylpiperazin-1-yl)benzamide;
N-(2-methyl-8-(trifluoromethyl)imidazo[1,2-a]pyridin-6-yl)-6-(piperazin-1-yl)nicotinamide;
rac-N-(2-methyl-8-(trifluoromethyl)imidazo[1,2-a]pyridin-6-yl)-6-(3-methylpiperazin-1-yl)nicotinamide;
(S)-6-(hexahydropyrrolo[1,2-a]pyrazin-2(1H)-yl)-N-(2-methyl-8-(trifluoromethyl)imidazo[1,2-a]pyridin-6-yl)nicotinamide;
6-(3,5-dimethylpiperazin-1-yl)-N-(2-methyl-8-(trifluoromethyl)imidazo[1,2-a]pyridin-6-yl)nicotinamide;
(S)-2-fluoro-4-(hexahydropyrrolo[1,2-a]pyrazin-2(1H)-yl)-N-(2-methylimidazo[1,2-a]pyridin-6-yl)benzamide;
N-(8-fluoro-2-methylimidazo[1,2-a]pyridin-6-yl)-6-(4-methylpiperazin-1-yl)nicotinamide;
(S)-2-fluoro-4-(hexahydropyrrolo[1,2-a]pyrazin-2(1H)-yl)-N-(2-methyl-8-(trifluoromethyl)imidazo[1,2-a]pyridin-6-yl)benzamide;
N-(8-fluoro-2-methylimidazo[1,2-a]pyridin-6-yl)-4-(piperazin-1-yl)benzamide;
rac-N-(2,8-dimethylimidazo[1,2-a]pyridin-6-yl)-2-fluoro-4-(3-methylpiperazin-1-yl)benzamide;
rac-2-fluoro-N-(8-fluoro-2-methylimidazo[1,2-a]pyridin-6-yl)-4-(3-methylpiperazin-1-yl)benzamide;
2-fluoro-N-(8-fluoro-2-methylimidazo[1,2-a]pyridin-6-yl)-4-(piperazin-1-yl)benzamide;
N-(8-fluoro-2-methylimidazo[1,2-a]pyridin-6-yl)-6-(piperazin-1-yl)nicotinamide;
rac-N-(8-fluoro-2-methylimidazo[1,2-a]pyridin-6-yl)-6-(3-methylpiperazin-1-yl)nicotinamide;

rac-N-(8-fluoro-2-methylimidazo[1,2-a]pyridin-6-yl)-5-(3-methylpiperazin-1-yl)picolinamide;
2-fluoro-N-(2-methylimidazo[1,2-a]pyridin-6-yl)-4-(piperazin-1-yl)benzamide;
rac-2,3-difluoro-N-(8-fluoro-2-methylimidazo[1,2-a]pyridin-6-yl)-4-(3-methylpiperazin-1-yl)benzamide;
rac-2,5-difluoro-N-(8-fluoro-2-methylimidazo[1,2-a]pyridin-6-yl)-4-(3-methylpiperazin-1-yl)benzamide;
rac-5-fluoro-N-(8-fluoro-2-methylimidazo[1,2-a]pyridin-6-yl)-6-(3-methylpiperazin-1-yl)nicotinamide;
rac-3-fluoro-N-(8-fluoro-2-methylimidazo[1,2-a]pyridin-6-yl)-5-(3-methylpiperazin-1-yl)picolinamide;
rac-2,6-difluoro-N-(8-fluoro-2-methylimidazo[1,2-a]pyridin-6-yl)-4-(3-methylpiperazin-1-yl)benzamide;
(S)-2-fluoro-N-(8-fluoro-2-methylimidazo[1,2-a]pyridin-6-yl)-4-(3-methylpiperazin-1-yl)benzamide;
(R)-2-fluoro-N-(8-fluoro-2-methylimidazo[1,2-a]pyridin-6-yl)-4-(3-methylpiperazin-1-yl)benzamide;
rac-N-(2,7-dimethylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-5-fluoro-6-(3-methylpiperazin-1-yl)nicotinamide;
rac-N-(8-chloro-2-methylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-6-(3-methylpiperazin-1-yl)nicotinamide;
rac-N-(8-chloro-2-methylimidazo[1,2-a]pyridin-6-yl)-3-fluoro-5-(3-methylpiperazin-1-yl)picolinamide;
rac-N-(8-chloro-2-methylimidazo[1,2-a]pyridin-6-yl)-2,6-difluoro-4-(3-methylpiperazin-1-yl)benzamide;
2-fluoro-N-(2-methyl-8-(trifluoromethyl)imidazo[1,2-a]pyridin-6-yl)-4-(piperazin-1-yl)benzamide;
2-fluoro-N-(2-methylimidazo[1,2-a]pyridin-6-yl)-4-(1,2,3,6-tetrahydropyridin-4-yl)benzamide;
2-fluoro-N-(8-fluoro-2-methylimidazo[1,2-a]pyridin-6-yl)-4-(1,2,3,6-tetrahydropyridin-4-yl)benzamide;
N-(8-fluoro-2-methylimidazo[1,2-a]pyridin-6-yl)-6-(1,2,3,6-tetrahydropyridin-4-yl)nicotinamide;
N-(2-methylimidazo[1,2-a]pyridin-6-yl)-5-(1,2,3,6-tetrahydropyridin-4-yl)picolinamide;
N-(8-fluoro-2-methylimidazo[1,2-a]pyridin-6-yl)-2-methoxy-6-(piperazin-1-yl)nicotinamide;
2-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-3-methyl-4-(piperazin-1-yl)benzamide;
N-(8-fluoro-2-methylimidazo[1,2-a]pyridin-6-yl)-5-methyl-6-(piperazin-1-yl)nicotinamide; 4-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-4-methoxy-6-(piperazin-1-yl)nicotinamide; 4-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-4-(2,2,2-trifluoroethoxy)nicotinamide;
2-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-2-(2,2,2-trifluoroethoxy)nicotinamide;
rac-N-(8-fluoro-2-methylimidazo[1,2-a]pyridin-6-yl)-2-methoxy-6-(3-methylpiperazin-1-yl)nicotinamide;
6-(3,3-dimethylpiperazin-1-yl)-N-(8-fluoro-2-methylimidazo[1,2-a]pyridin-6-yl)-2-methoxynicotinamide;
rac-N-(8-fluoro-2-methylimidazo[1,2-a]pyridin-6-yl)-4-methoxy-6-(3-methylpiperazin-1-yl)nicotinamide;
N-(2-methylimidazo[1,2-a]pyridin-6-yl)-6-(1,2,3,6-tetrahydropyridin-4-yl)nicotinamide;
N-(2-methylimidazo[1,2-a]pyridin-6-yl)-6-(1-methylpiperidin-4-yl)nicotinamide;
N-(8-fluoro-2-methylimidazo[1,2-a]pyridin-6-yl)-6-(piperidin-4-yl)nicotinamide;
N-(8-fluoro-2-methylimidazo[1,2-a]pyridin-6-yl)-6-(1-methylpiperidin-4-yl)nicotinamide;
2-fluoro-N-(8-fluoro-2-methylimidazo[1,2-a]pyridin-6-yl)-4-(piperidin-4-yl)benzamide;
rac-6-(3,4-dimethylpiperazin-1-yl)-N-(2-methylimidazo[1,2-a]pyridin-6-yl)nicotinamide;
and pharmaceutically acceptable salts thereof.

A particular embodiment of the present invention relates to compounds of formula (I$^c$)

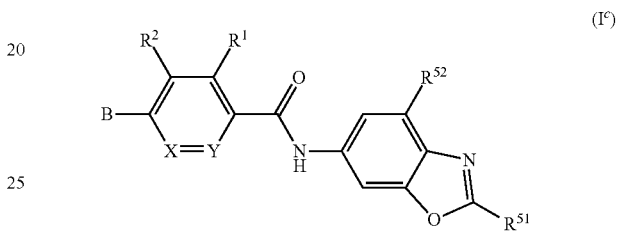

wherein B, X, Y, R, R$^2$, R$^{51}$, and R$^{52}$ are as described herein.

Particular compounds of formula (I$^c$) of the present invention are those selected from the group consisting of:
6-(3,5-dimethylpiperazin-1-yl)-N-(4-fluoro-2-methylbenzo[d]oxazol-6-yl)nicotinamide;
N-(4-fluoro-2-methylbenzo[d]oxazol-6-yl)-6-(4-methylpiperazin-1-yl)nicotinamide;
(S)—N-(4-fluoro-2-methylbenzo[d]oxazol-6-yl)-6-(hexahydropyrrolo[1,2-a]pyrazin-2(1H)-yl)nicotinamide;
N-(4-Fluoro-2-methyl-benzooxazol-6-yl)-6-piperazin-1-yl-nicotinamide;
rac-N-(4-Fluoro-2-methyl-benzooxazol-6-yl)-6-(3-methyl-piperazin-1-yl)-nicotinamide;
N-(4-fluoro-2-methylbenzo[d]oxazol-6-yl)-4-(piperazin-1-yl)benzamide;
rac-N-(4-fluoro-2-methylbenzo[d]oxazol-6-yl)-4-(3-methylpiperazin-1-yl)benzamide;
4-(3,5-dimethylpiperazin-1-yl)-N-(4-fluoro-2-methylbenzo[d]oxazol-6-yl)benzamide;
(S)-2-Fluoro-N-(4-fluoro-2-methyl-benzooxazol-6-yl)-4-(S)-hexahydro-pyrrolo[1,2-a]pyrazin-2-yl-benzamide;
(R)-2-fluoro-N-(4-fluoro-2-methylbenzo[d]oxazol-6-yl)-4-(hexahydropyrrolo[1,2-a]pyrazin-2(1H)-yl)benzamide;
rac-2-fluoro-N-(2-methylbenzo[d]oxazol-6-yl)-4-(3-methylpiperazin-1-yl)benzamide;
2-fluoro-N-(4-fluoro-2-methylbenzo[d]oxazol-6-yl)-4-(piperazin-1-yl)benzamide;
and pharmaceutically acceptable salts thereof.

Manufacturing Processes

Compounds of formula (I) and pharmaceutically acceptable salts thereof as defined above be prepared following standard methods known in the art.

In a particular embodiment, the invention further relates to a process for the manufacture of compounds of formula (I) and pharmaceutically acceptable salts thereof as defined above, comprising:

a) the Buchwald-Hartwig amination reaction of a compound of formula (II)

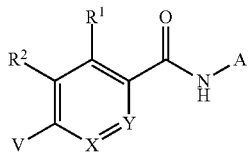

(II)

with a compound of formula B—H, in the presence of a catalyst (e.g. tris(dibenzylidene-acetone)dipalladium (0) (Pd$_2$(dba)$_3$)) and a ligand (e.g. 2,2'-bis(diphenylphosphino)-1,1'-binaphthyl (BINAP)) and a base (e.g. cesium carbonate) and a solvent (e.g. toluene), wherein the hydrogen H of the compound of formula B—H is bound to a ring nitrogen atom of B, V is chloro or bromo, and A, B, X, Y, R$^1$, and R$^2$ are as defined above; or
b) a nucleophilic aromatic substitution reaction between a compound of formula (II) with a compound of formula B—H by heating (e.g. T=120° C.-200° C.) in a solvent (e.g. dimethyl sulfoxide (DMSO), N-methylpyrrolidone (NMP), or dimethylformamide (DMF)), wherein the hydrogen H of the compound of formula B—H is bound to a ring nitrogen atom of B, V is fluoro if X is CR$^3$ or V is chloro if X is N, and A, B, X, Y, R$^1$, R$^2$ and R$^3$ are as defined above; or
c) the Suzuki coupling reaction of a compound of formula (II) with a compound of formula PG-B-pinB in the presence of a base (e.g. K$_2$CO$_3$) and a catalyst (e.g. PdCl$_2$), followed by removal of PG, wherein pinB is pinacolboranyl (4,4,5,5-tetramethyl-1,3,2-dioxaborolan-2-yl) which is bound to a ring carbon atom of B, PG is an amino-protecting group such as tert-butoxycarbonyl (BOC), V is fluoro or chloro, and wherein A, B, X, Y, R$^1$, and R$^2$ are as defined above; or
d) the amidation reaction of a compound of formula (III)

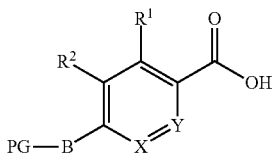

(III)

with a compound of formula A-NH$_2$ in the presence of a tertiary amine (e.g. N,N-diisopropylethylamine (DIPEA) or triethylamine (TEA)) and a coupling reagent (e.g. 2-(1H-7-azabenzotriazol-1-yl)-1,1,3,3-tetramethyluronium hexafluorophosphate methanaminium (HATU) or O-(benzotriazol-1-yl)-N,N,N',N'-tetramethyluronium tetrafluoroborate (TBTU)), optionally followed by the removal of PG, wherein PG is an optional amino-protecting group such as tert-butoxycarbonyl (PG), and wherein A, B, X, Y, R$^1$, and R$^2$ are as defined above.

Particularly, compounds of formula (I) and pharmaceutically acceptable salts thereof can be prepared in accordance to the methods described in the examples herein.

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 µm filter, to remove impurities and contaminants.

Uses

As described above, the compounds of formula (I) and their pharmaceutically acceptable salts possess valuable pharmacological properties and have been found to be enhancing inclusion of exon 7 of SMN1 and/or SMN2 into mRNA transcribed from the SMN1 and/or SMN2 gene, thereby increasing expression of SMN protein in a human subject in need thereof.

The compounds of the present invention can be used, either alone or in combination with other drugs, for the treatment or prevention of diseases caused by an inactivating mutation or deletion in the SMN1 gene and/or associated with loss or defect of SMN1 gene function. These diseases include, but are not limited to spinal muscular atrophy (SMA).

A particular embodiment of the present invention relates to pharmaceutical compositions comprising compounds of formula (I) as defined above or their pharmaceutically acceptable salts as defined above and one or more pharmaceutically acceptable excipients.

A particular embodiment of the present invention relates to pharmaceutical compositions comprising compounds of formula (I) or their pharmaceutically acceptable salts as defined above and one or more pharmaceutically acceptable excipients for the treatment or prevention of diseases caused by an inactivating mutation or deletion in the SMN1 gene and/or associated with loss or defect of SMN1 gene function, particularly for the treatment or prevention of spinal muscular atrophy (SMA).

A particular embodiment of the present invention relates to compounds of formula (I) or their pharmaceutically acceptable salts as defined above for use as therapeutically active substances, especially for use as therapeutically active substances for the treatment or prevention of diseases caused by an inactivating mutation or deletion in the SMN1 gene and/or associated with loss or defect of SMN1 gene function, particularly for the treatment or prevention of spinal muscular atrophy (SMA).

A particular embodiment of the present invention relates to compounds of formula (I) or their pharmaceutically acceptable salts as defined above for the use in the treatment or prevention of diseases caused by an inactivating mutation or deletion in the SMN1 gene and/or associated with loss or defect of SMN1 gene function, particularly for use in the treatment or prevention of spinal muscular atrophy (SMA).

A particular embodiment of the present invention relates to a method for the treatment or prevention of diseases caused by an inactivating mutation or deletion in the SMN1 gene and/or associated with loss or defect of SMN1 gene function, particularly for the treatment or prevention of spinal muscular atrophy (SMA), which method comprises administering compounds of formula (I) or their pharmaceutically acceptable salts as defined above to a subject.

A particular embodiment of the present invention relates to the use of compounds of formula (I) or their pharmaceutically acceptable salts as defined above for the treatment or prevention of diseases caused by an inactivating mutation or deletion in the SMN1 gene and/or associated with loss or defect of SMN1 gene function, particularly for the treatment or prevention of spinal muscular atrophy (SMA).

A particular embodiment of the present invention relates to the use of compounds of formula (I) or their pharmaceutically acceptable salts as defined above for the preparation of medicaments for the treatment or prevention of diseases caused by an inactivating mutation or deletion in the SMN1 gene and/or associated with loss or defect of SMN1 gene function, particularly for the treatment or prevention of spinal muscular atrophy (SMA). Such medicaments comprise compounds of formula (I) or their pharmaceutically acceptable salts as defined above.

EXAMPLES

The invention will be more fully understood by reference to the following examples. They should however not be construed as limiting the scope of the invention.

PREPARATION OF INTERMEDIATES

Example A.1

Preparation of N-(6,8-dimethylimidazo[1,2-a]pyrazin-2-yl)-4-fluorobenzamide

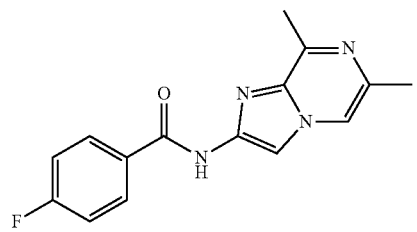

To a mixture of 6,8-dimethylimidazo[1,2-a]pyrazin-2-amine trihydrochloride (Example B.1) (134 mg, 494 µmol) and N-Ethyldiisopropylamine (320 mg, 420 µl, 2.47 mmol) in dioxane (2.0 ml) was added dropwise a solution of 4-fluorobenzoyl chloride (80 mg, 60.3 µl, 494 µmol) in dioxane (0.5 ml) at room temperature. The mixture was stirred for 1 hour. The solvent was removed in vacuo. The solid was taken in water and the suspension was stirred for 15 minutes. The solid was filtered and dried to provide 125 mg (89%) of the title compound as an off-white solid. MS (m/e): 285.4 (M+H+)

In analogy to Example A.1, Examples A.2 to A.7 of the following table were prepared from the acylchloride and amine derivatives:

| Example No. | Structure | Systematic Name | Starting materials |
| --- | --- | --- | --- |
| A.2 | 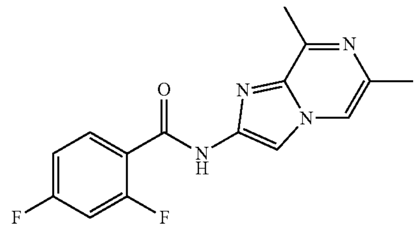 [SMILES: Cc1cn2cc(NC(=O)c3ccc(F)cc3F)nc2c(C)n1] | N-(6,8-dimethyl-imidazo[1,2-a]-pyrazin-2-yl)-2,4-difluorobenzamide | 6,8-dimethylimidazo-[1,2-a]pyrazin-2-amine trihydrochloride (Example B.1) and 2,4-difluorobenzoyl chloride (commercial) |
| A.3 | 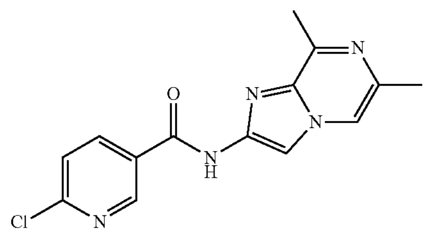 [SMILES: Cc1cn2cc(NC(=O)c3ccc(Cl)nc3)nc2c(C)n1] | 6-chloro-N-(6,8-dimethylimidazo-[1,2-a]pyrazin-2-yl)nicotinamide | 6,8-dimethylimidazo-[1,2-a]pyrazin-2-amine trihydrochloride (Example B.1) and 6-chloronicotinoyl chloride (commercial) |
| A.4 | 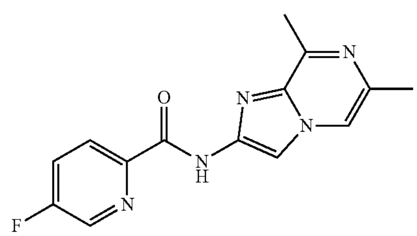 [SMILES: Cc1cn2cc(NC(=O)c3ccc(F)cn3)nc2c(C)n1] | N-(6,8-dimethyl-imidazo[1,2-a]-pyrazin-2-yl)-5-fluoropicolinamide | 6,8-dimethylimidazo-[1,2-a]pyrazin-2-amine trihydrochloride (Example B.1) and 5-Fluoro-pyridine-2-carbonyl chloride (717871-83-5) |
| A.5 | 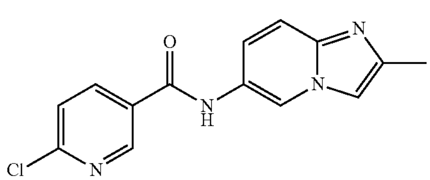 [SMILES: Cc1cn2cc(NC(=O)c3ccc(Cl)nc3)ccc2n1] | 6-chloro-N-(2-methylimidazo-[1,2-a]pyridin-6-yl)nicotinamide | 2-methylimidazo-[1,2-a]pyridin-6-amine hydrobromide (commercial) and 6-chloronicotinoyl chloride (commercial) |
| A.6 | 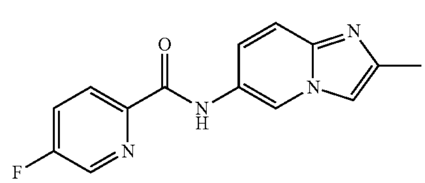 [SMILES: Cc1cn2cc(NC(=O)c3ccc(F)cn3)ccc2n1] | 5-fluoro-N-(2-methylimidazo-[1,2-a]pyridin-6-yl)picolinamide | 2-methylimidazo-[1,2-a]pyridin-6-amine hydrobromide (commercial) and 5-Fluoro-pyridine-2-carbonyl chloride (717871-83-5) |
| A.7 | 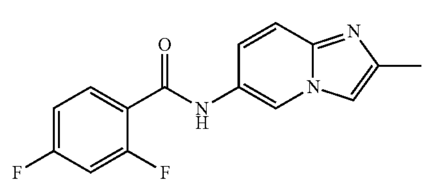 [SMILES: Cc1cn2cc(NC(=O)c3ccc(F)cc3F)ccc2n1] | 2,4-difluoro-N-(2-methylimidazo-[1,2-a]pyridin-6-yl)benzamide | 2-methylimidazo-[1,2-a]pyridin-6-amine hydrobromide (commercial) and 2,4-difluorobenzoyl chloride (commercial) |

Example A.8

Preparation of 6-Chloro-N-(2-methyl-8-trifluoromethyl-imidazo[1,2-a]pyridin-6-yl)-nicotinamide

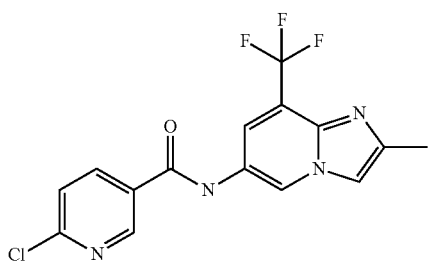 [SMILES: Cc1cn2cc(NC(=O)c3ccc(Cl)nc3)cc(C(F)(F)F)c2n1]

To a solution of 6-chloronicotinic acid (332 mg, 2.11 mmol) in DMF (4 ml) under argon at room temperature, were added HATU (O-(7-azabenzotriazol-1-yl)-N,N,N',N'-tetramethyluronium hexafluorophosphate) (1.2 g, 3.16 mmol) and N,N-diisopropylethylamine (1.4 ml, 8.42 mmol). After 5 minutes stirring, 2-methyl-8-(trifluoromethyl)imidazo[1,2-a]pyridin-6-amine hydrochloride (Example B.2) (530 mg, 2.11 mmol) was added. The mixture was stirred at room temperature for two days. The solvent was removed in vacuo. The residue was taken in aqueous bicarbonate. The aqueous layer was extracted 3 times with ethyl acetate. The combined extracts were dried over sodium sulfate, filtered and concentrated in vacuo. The crude mixture was purified with flash column chromatography on silica eluting with a gradient formed from dichloromethane and methanol (0 to 5%) to provide the title compound.

In analogy to Example A.8, Examples A.9 to A.10 of the following table were prepared from the acid and amine derivatives:

Example B.1

Preparation of 6,8-dimethylimidazo[1,2-a]pyrazin-2-amine trihydrochloride

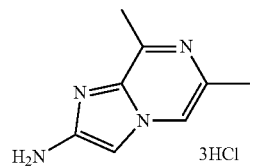

a) step 1: Ethyl 6,8-dimethylimidazo[1,2-a]pyrazine-2-carboxylate hydrobromide To a solution of 3,5-dimethylpyrazin-2-amine (200 mg, 1.62 mmol) in DME (6.00 ml) was added ethyl 3-bromo-2-oxopropanoate (380 mg, 245 μl, 1.95 mmol) at 0° C. The mixture was stirred for 2 hours at room temperature. The suspension was filtered and washed with dimethoxyethane. The filtrate was taken in ethanol (4 ml) and refluxed for 1.5 hours. The reaction mixture was cooled to room temperature, filtered and washed with ethanol to provide 323 mg (66.3%) of the title compound as a light yellow solid. MS (m/e): 220.1 (M+H+)

b) step 2: 6,8-dimethylimidazo[1,2-a]pyrazine-2-carboxylic acid hydrochloride To a solution of ethyl 6,8-dimethylimidazo[1,2-a]pyrazine-2-carboxylate hydrobromide (300 mg, 0.999 mmol) in ethanol (6 ml) and water (3 ml) under nitrogen at room temperature, was added sodium hydroxide 2M (1.05 ml, 2.1 mmol). The reaction mixture was stirred at 90° C. for 2 hours. The mixture was cooled to room temperature and acidified with 1 ml HCl solution (2 M). The resulting suspension was cooled to 0° C., filtered, washed with cold

| Example No. | Structure | Systematic Name | Starting materials |
|---|---|---|---|
| A.9 | 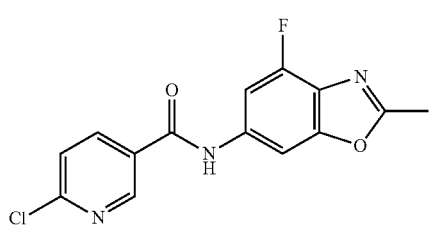 [SMILES: Cc1nc2c(F)cc(NC(=O)c3ccc(Cl)nc3)cc2o1] | 6-chloro-N-(4-fluoro-2-methyl-benzo[d]oxazol-6-yl)nicotinamide | 4-fluoro-2-methyl-benzo[d]oxazol-6-amine hydrochloride (Example B.3) and 6-chloronicotinic acid (commercial) |
| A.10 | 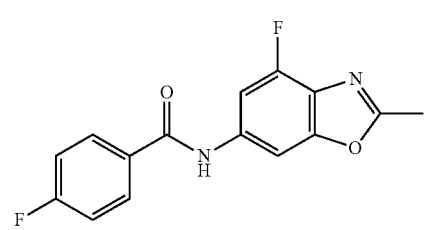 | 4-fluoro-N-(4-fluoro-2-methyl-benzo[d]oxazol-6-yl)benzamide | 4-fluoro-2-methyl-benzo[d]oxazol-6-amine hydrochloride (Example B.3) and 4-fluorobenzoic acid (commercial) | diethyl ether and dried to provide 128 mg (56.3%) of the title compound as a light brown solid. MS (m/e): 192.1 (M+H+)

c) step 3: tert-butyl 6,8-dimethylimidazo[1,2-a]pyrazin-2-ylcarbamate

To a suspension of 6,8-dimethylimidazo[1,2-a]pyrazine-2-carboxylic acid hydrochloride (5 g, 22.0 mmol) in tert-butanol (50.9 ml) under nitrogen at room temperature, was added triethylamine (9.17 ml, 65.9 mmol). After stirring for 10 minutes, diphenylphosphoryl azide (4.85 ml, 22.0 mmol) was added. The reaction mixture was stirred at 85° C. overnight.

The solvent was removed in vacuo. The residue was taken in aqueous bicarbonate. The aqueous layer was extracted 3 times with ethyl acetate. The combined extracts were dried over sodium sulfate, filtered and concentrated in vacuo. The crude orange oil was purified with flash column chromatography on silica eluting with a gradient formed from n-heptane and ethyl acetate (0 to 60%) to provide 3.57 g (y: 62.0%) of the title compound as a white foam. MS(m/e): 263.5 (M+H+)

d) step 4: 6,8-dimethylimidazo[1,2-a]pyrazin-2-amine trihydrochloride

To a yellow solution of tert-butyl 6,8-dimethylimidazo[1,2-a]pyrazin-2-ylcarbamate (3.57 g, 13.6 mmol) in methanol (35.7 ml) under nitrogen at room temperature, was added dropwise hydrogen chloride (34.0 ml, 136 mmol, 4M in dioxane). The reaction mixture was stirred at room temperature overnight. The mixture was evaporated to provide 3.66 g (99%) of the title compound as a yellow solid. MS(m/e): 163.2 (M+H+)

Example B.2

Preparation of 2-Methyl-8-trifluoromethyl-imidazo[1,2-a]pyridin-6-ylamine hydrochloride

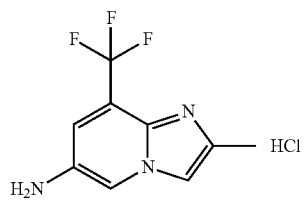

a) step 1: 6-bromo-2-methyl-8-(trifluoromethyl)imidazo[1,2-a]pyridine

In a 30 ml sealed reactor, 5-bromo-3-(trifluoromethyl)pyridin-2-amine (CAS:79456-34-1) (2.5 g, 10.4 mmol) was combined with 1-chloropropan-2-one (1.04 ml, 12.4 mmol) in acetonitrile (25 ml) and heated at 130° C. for 2 days. The reaction mixture was cooled to room temperature, quenched with 100 ml of a saturated aqueous sodium bicarbonate solution. The reaction was extracted with ethylacetate and water. The organic layers were dried over sodium sulfate and concentrated in vacuo. The crude residue was purified with flash column chromatography on silica eluting with a gradient formed from n-heptane and ethyl acetate (0 to 25%) to provide 1.2 g (y: 41.5%) of the title compound as a pink solid.

b) step 2: N-(diphenylmethylene)-2-methyl-8-(trifluoromethyl)imidazo[1,2-a]pyridin-6-amine In a 250 mL pear-shaped flask, 6-bromo-2-methyl-8-(trifluoromethyl)imidazo[1,2-a]pyridine (2.79 g, 10.0 mmol), rac 2,2'-bis(diphenylphosphino)-1,1'-binaphtalene (623 mg, 1.00 mmol), palladium (II) acetate (224 mg, 1.00 mmol), cesium carbonate (8.14 g, 25.0 mmol) and diphenylmethanimine (2.48 g, 2.3 ml, 13.0 mmol) were combined with THF (70 ml) to give a orange suspension. The reaction mixture was heated to 70° C. and stirred for 23 h. The reaction was extracted with ethylacetate and water. The organic layers were dried over sodium sulfate and concentrated in vacuo. The crude residue purified with flash column chromatography on silica eluting with a gradient formed from n-heptane and ethyl acetate (0 to 25%) to provide 2.33 g (y: 61.0%) of the title compound as a yellow oil. MS(m/e): 380.5 (M+H+).

c) step 3: 2-Methyl-8-trifluoromethyl-imidazo[1,2-a]pyridin-6-ylamine hydrochloride To a solution of N-(diphenylmethylene)-2-methyl-8-(trifluoromethyl)imidazo[1,2-a]pyridin-6-amine (2.3 g, 6.06 mmol) in dioxane (20 ml) was added HCl 1N (7.58 ml, 7.58 mmol). The mixture was stirred at room temperature for 30 minutes. The solvent was removes in vacuo. The residue was triturated in acetonitrile. The white solid was filtered, washed with acetonitrile and dried to provide 1.08 g (71%) of the expected compound as a white solid. MS (m/e): 216.5 (M+H+)

Example B.3

Preparation of 4-fluoro-2-methylbenzo[d]oxazol-6-amine hydrochloride

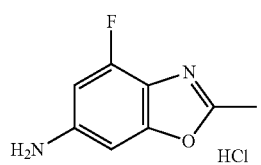

a) step 1: 6-Bromo-4-fluoro-2-methyl-benzooxazole

To a solution of 4'-bromo-2',6'-difluoroacetanilide (4.0 g, 15.6 mmol, CAS: 658072-14-1) in N-methyl-2-pyrrolidinone (25 ml) was added cesium carbonate (10.3 g, 31.6 mmol) and the mixture heated to 150° C. for 1 h. The reaction was then diluted with water and extracted with ethyl acetate. The organic phase was washed with brine, dried over sodium sulfate and concentrated in vacuo. The crude residue was purified with flash column chromatography on silica eluting with a gradient formed from n-heptane and ethyl acetate (20% to 50%) to provide 1.5 g (42%) of the title compound as a light brown solid. MS (m/e): 273.1 (M+H+MeCN).

b) step 2: 4-fluoro-2-methylbenzo[d]oxazol-6-amine hydrochloride

In analogy to the procedure described for the synthesis of example B.2 (steps: 2-3), the title compound was prepared from 6-Bromo-4-fluoro-2-methyl-benzooxazole. MS (m/e): 216.5 (M+H+).

Example B.4

Preparation of 8-Fluoro-2-methyl-imidazo[1,2-a]pyridin-6-ylamine hydrochloride

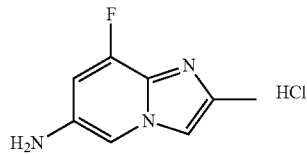

In analogy to the procedure described for the synthesis of example B.2 (steps: 1-3), the title compound was prepared from 5-bromo-3-fluoro-pyridin-2-ylamine (CAS: 748812-37-5). MS (m/e): 166.2 (M+H+).

Example B.5

Preparation of 8-chloro-2-methylimidazo[1,2-a]pyridin-6-amine hydrochloride

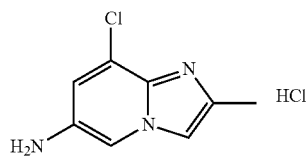

In analogy to the procedure described for the synthesis of example B.2 (steps: 1-3), the title compound was prepared from 5-bromo-3-chloro-pyridin-2-ylamine (CAS: 38185-55-6). MS (m/e): 182.1 (M+H+).

Example C.1

Preparation of (S)-2-fluoro-4-(hexahydropyrrolo[1,2-a]pyrazin-2(1H)-yl)benzoic acid

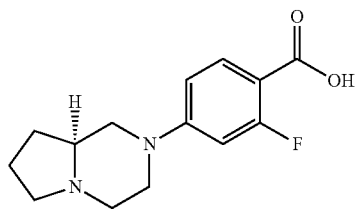 [SMILES: O=C(O)c1ccc(N2CCN3CCC[C@H]3C2)cc1F]

a) step 1: (S)-methyl 2-fluoro-4-(hexahydropyrrolo[1,2-a]pyrazin-2(1H)-yl)benzoate Toluene (1.5 ml) was added to a mixture of methyl 4-bromo-2-fluorobenzoate (200 mg, 832 µmol) and (S)-octahydropyrrolo[1,2-a]pyrazine (130 mg, 999 µmol). The mixture was stirred until complete dissolution. Then cesium carbonate (407 mg, 1.25 mmol) was added. Then Pd$_2$(dba)$_3$ (22.9 mg, 25.0 µmol) and BINAP (46.7 mg, 74.9 µmol) were added. The reaction mixture was stirred vigorously for 24 hours at 110° C. The reaction mixture was cooled to room temperature. Water and ethylacetate were added. The layers were separated. The aqueous layer was extracted twice with ethylacetate. The combined organic layers were washed with water, dried over sodium sulfate, filtered and evaporated. The crude orange oil was purified with flash column chromatography on silica eluting with a gradient formed from n-heptane and ethyl acetate (0 to 80%) to provide 121 mg (y: 52.2%) of the title compound as a yellow oil MS (m/e): 279.5 (M+H+)

b) step 2: (S)-2-fluoro-4-(hexahydropyrrolo[1,2-a]pyrazin-2(1H)-yl)benzoic acid

To a solution of (S)-methyl 2-fluoro-4-(hexahydropyrrolo[1,2-a]pyrazin-2(1H)-yl)benzoate (100 mg, 359 µmol) in tetrahydrofuran (513 µl), methanol (256 µl) and water (256 µl) was added lithium hydroxide monohydrate (45.2 mg, 1.08 mmol). The mixture was stirred at room temperature for 6 hours. The mixture was evaporated. HCl 2N was added dropwise to pH 3-4. Dichloromethane was added and the aqueous layer was extracted 3 times with dichloromethane NaOH 5N was added to the aqueous phase to reach pH 6. The solution was evaporated. The residue was suspended in dichloromethane and methanol, filtered and evaporated to provide 82 mg (86.4%) of the title compound as colorless oil. MS (m/e): 265.5 (M+H+)

Example C.2

Preparation of (R)-2-fluoro-4-(hexahydropyrrolo[1,2-a]pyrazin-2(1H)-yl)benzoic acid

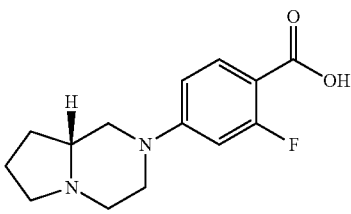 [SMILES: O=C(O)c1ccc(N2CCN3CCC[C@@H]3C2)cc1F]

In analogy to the procedure described for the synthesis of example C.1 (steps: 1-2), the title compound was prepared from 4-bromo-2-fluorobenzoate and (R)-octahydropyrrolo[1,2-a]pyrazine.

Example C.3

Preparation of rac-4-(4-(tert-butoxycarbonyl)-3-methylpiperazin-1-yl)-2-fluorobenzoic acid

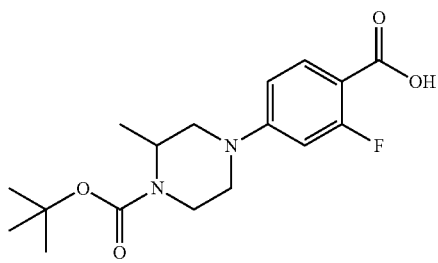 [SMILES: CC1CN(c2ccc(C(=O)O)c(F)c2)CCN1C(=O)OC(C)(C)C]

a) step 1: rac-tert-butyl 4-(4-(ethoxycarbonyl)-3-fluorophenyl)-2-methylpiperazine-1-carboxylate A solution of ethyl 2,4-difluorobenzoate (200 mg, 1.07 mmol) and 2-methylpiperazine (538 mg, 5.37 mmol) in DMA (2 ml) was heated to 100° C. in a microwave reactor for 15 minutes. Ethyl acetate and water was added. The layers were separated and the aqueous layer was extracted twice with ethyl acetate. The combined organic layers were dried over sodium sulfate, filtered and evaporated. A solution of this crude material and triethylamine (131 mg, 180 µl, 1.29 mmol) in dichloromethane (2.00 ml) was cooled to 0° C. Di-tert-butyl dicarbonate (352 mg, 1.61 mmol) in dichloromethane (0.5 ml) was added dropwise. The mixture was stirred at room temperature overnight. Water was added. The layers were separated. The aqueous layer was extracted twice with dichloromethane. The combined organic layers were dried over sodiumsulfate, filtered and evaporated. The crude product was purified with flash column chromatography on silica gel (Eluent: Heptane/ethyl acetate 0 to 20) to provide 155 mg (34%) of the title compound as a light yellow oil.

b) step 2: rac-4-(4-(tert-butoxycarbonyl)-3-methyl-piperazin-1-yl)-2-fluorobenzoic acid In analogy to the procedure described for the synthesis of example C.1 (step: 2), the title compound was prepared from rac-tert-butyl 4-(4-(ethoxycarbonyl)-3-fluorophenyl)-2-methylpiperazine-1-carboxylate

Example C.4

Preparation of rac-4-(6-Carboxy-pyridin-3-yl)-2-methyl-piperazine-1 carboxylic acid tert-butyl ester

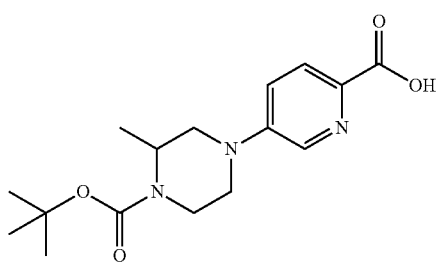 [SMILES: CC1CN(c2ccc(C(=O)O)nc2)CCN1C(=O)OC(C)(C)C]

A solution of 5-fluoropicolinic acid (0.47 g, 3.33 mmol) and 2-methylpiperazine N1 Boc (1.00 g, 5.00 mmol) in DMA (2.00 ml) was heated to 160° C. in a microwave reactor for 1 hour. The solvent was evaporated under high vacuum. The residue was taken in water and acidified to pH 3. The aqueous phase was extracted 3 times with ethyl acetate, dried and concentrated. The crude product was purified with flash column chromatography on silica gel (Eluent: Heptane/ethyl acetate 0 to 20) to provide 1.17 g (100%) of the title compound.

Example C.5

Preparation of rac-4-(4-(tert-butoxycarbonyl)-3-methylpiperazin-1-yl)-2,3-difluorobenzoic acid

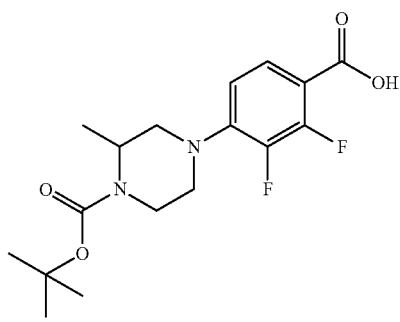 [SMILES: CC1CN(c2ccc(C(=O)O)c(F)c2F)CCN1C(=O)OC(C)(C)C]

In analogy to the procedure described for the synthesis of example C.3 (steps: 1-2), the title compound was prepared from 2,3,4-trifluoro-benzoic acid ethyl ester and rac-2-methylpiperazine.

Example C.6

Preparation of rac-4-(4-Carboxy-2,5-difluoro-phenyl)-2-methyl-piperazine-1-carboxylic acid tert-butyl ester

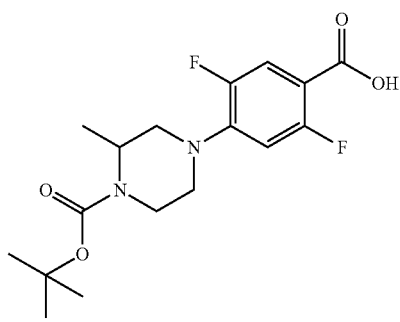 [SMILES: CC1CN(c2cc(F)c(C(=O)O)cc2F)CCN1C(=O)OC(C)(C)C]

In analogy to the procedure described for the synthesis of example C.3 (steps: 1-2), the title compound was prepared from 2,4,5-Trifluoro-benzoic acid methyl ester and rac-2-methylpiperazine.

Example C.7

Preparation of rac-6-(4-(tertbutoxycarbonyl)-3-methylpiperazin-1-yl)-5-fluoronicotinic acid

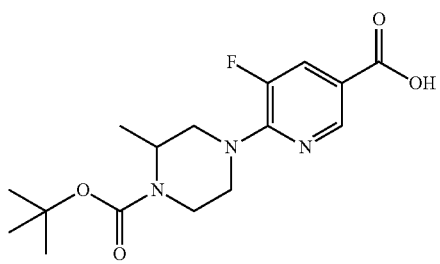 [SMILES: CC1CN(c2ncc(C(=O)O)cc2F)CCN1C(=O)OC(C)(C)C]

In analogy to the procedure described for the synthesis of example C.3 (steps: 1-2), the title compound was prepared from 6-Chloro-5-fluoro-nicotinic acid methyl ester and rac-2-methylpiperazine.

Example C.8

Preparation of rac-5-(4-(tertbutoxycarbonyl)-3-methylpiperazin-1-yl)-3-fluoropicolinic acid

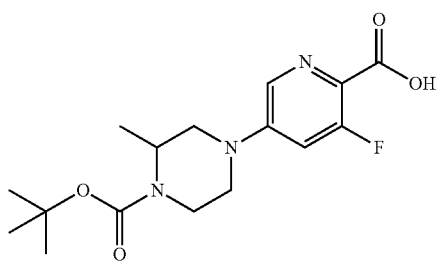 [SMILES: CC1CN(c2cnc(C(=O)O)c(F)c2)CCN1C(=O)OC(C)(C)C]

In analogy to the procedure described for the synthesis of example C.3 (steps: 1-2), the title compound was prepared from 3,5-Difluoro-pyridine-2-carboxylic acid methyl ester and rac-2-methylpiperazine.

Example C.9

Preparation of rac-4-(4-(tertbutoxycarbonyl)-3-methylpiperazin-1-yl)-2,6-difluorobenzoic acid

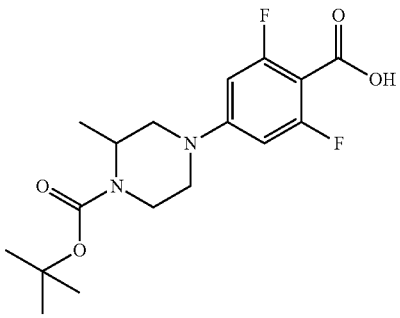 [SMILES: CC1CN(c2cc(F)c(C(=O)O)c(F)c2)CCN1C(=O)OC(C)(C)C]

In analogy to the procedure described for the synthesis of example C.3 (steps: 1-2), the title compound was prepared from 2,4,6-Trifluoro-benzoic acid methyl ester and rac-2-methylpiperazine.

Example C.10

Preparation of (S)-4-(4-(tertbutoxycarbonyl)-3-methylpiperazin-1-yl)-2-fluorobenzoic acid

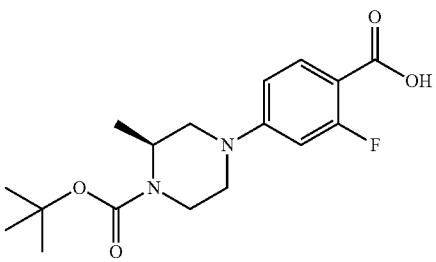 [SMILES: C[C@H]1CN(c2ccc(C(=O)O)c(F)c2)CCN1C(=O)OC(C)(C)C]

In analogy to the procedure described for the synthesis of example C.1 (steps: 1-2), the title compound was prepared from methyl 4-bromo-2-fluorobenzoate and (S)-tert-butyl 2-methylpiperazine-1-carboxylate.

Example C.11

Preparation of (R)-4-(4-(tertbutoxycarbonyl)-3-methylpiperazin-1-yl)-2-fluorobenzoic acid

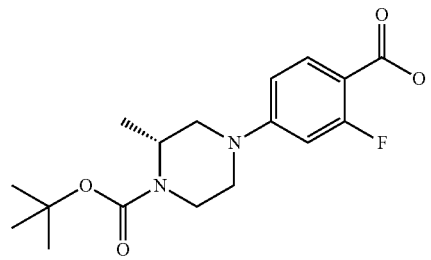 [SMILES: C[C@@H]1CN(c2ccc(C(=O)O)c(F)c2)CCN1C(=O)OC(C)(C)C]

In analogy to the procedure described for the synthesis of example C.1 (steps: 1-2), the title compound was prepared from methyl 4-bromo-2-fluorobenzoate and (R)-tert-butyl 2-methylpiperazine-1-carboxylate.

Example C.12

Preparation of 4-(1-(tert-butoxycarbonyl)-1,2,3,6-tetrahydropyridin-4-yl)-2-fluorobenzoic acid

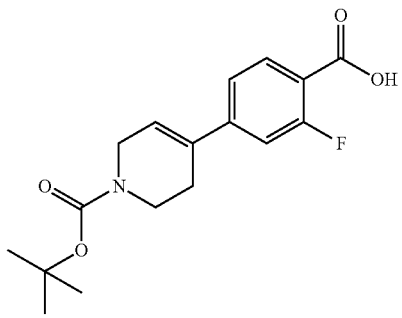 [SMILES: CC(C)(C)OC(=O)N1CC=C(c2ccc(C(=O)O)c(F)c2)CC1]

a) step 1: tert-butyl 4-(3-fluoro-4-(methoxycarbo-nyl)phenyl)-5,6-dihydropyridine-1(2H)-carboxylate To a solution of methyl 4-bromo-2-fluorobenzoate (94 mg, 395 μmol) in Dioxane (2 ml) were added tert-butyl 4-(4,4,5,5-tetramethyl-1,3,2-dioxaborolan-2-yl)-5,6-dihy-dropyridine-1(2H)-carboxylate (179.3 mg, 580 μmol), tet-rakis-(triphenylphosphine)palladium (22.8 mg, 19.8 μmol, Eq: 0.05) and tripotassium phosphate (170.1 mg, 801 μmol). Under an inert atmosphere, the mixture was heated at 100° C. for 18 h. The reaction was filtered and the filtrate was concentrated in vacuo. The resulting brown oil was purified by flash column chromatography on silica (Eluent: Heptane/ethyl acetate 0 to 20) to provide 121 mg (91%) of the title compound as a light yellow oil. MS (m/e): 280.4 (M+H−56)

b) step 2: 4-(1-(tert-butoxycarbonyl)-1,2,3,6-tetra-hydropyridin-4-yl)-2-fluorobenzoic acid In analogy to the procedure described for the synthesis of example C.1 (step: 2), the title compound was prepared from tert-butyl 4-(3-fluoro-4-(methoxycarbonyl)phenyl)-5,6-di-hydropyridine-1(2H)-carboxylate Example C.13

Preparation of 6-(1-(tert-butoxycarbonyl)-1,2,3,6-tetrahydropyridin-4-yl)nicotinic acid

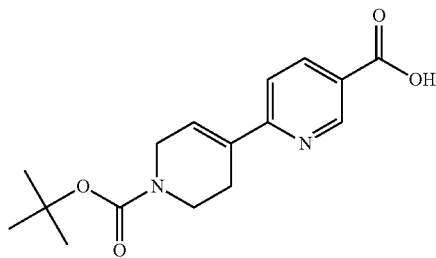 [SMILES: CC(C)(C)OC(=O)N1CC=C(c2ccc(C(=O)O)cn2)CC1]

To a solution of 6-chloronicotinic acid (200 mg, 1.26 mmol) in dry DMF (2.5 ml) under nitrogen at room temperature, were added tert-butyl 4-(4,4,5,5-tetramethyl-1,3,2-dioxaborolan-2-yl)-5,6-dihydropyridine-1(2H)-carboxylate (466 mg, 1.51 mmol), tetrakis(triphenylphosphine) palladium (0) (147 mg, 126 μmol) and potassium carbonate anhydrous (521 mg, 3.77 mmol). The reaction mixture was degased with nitrogen for 10 minutes. The mixture was then stirred at 125° C. in microwave for 45 min. The mixture was diluted with DMF. Water was added to the suspension and the mixture was cooled to 0° C. HCl 1N was slowly added, until pH 3-4. The suspension was filtered and the solid was washed with water and then ethyl acetate to provide 158 mg (41.3%) of the title compound as a white solid. MS (m/e): 305.5 (M+H+)

Example C.14

Preparation of 5-(1-(tert-butoxycarbonyl)-1,2,3,6-tetrahydropyridin-4-yl)picolinic acid

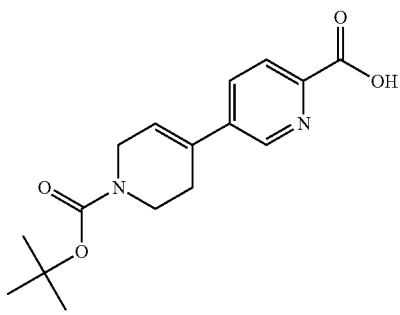 [SMILES: CC(C)(C)OC(=O)N1CC=C(c2ccc(C(=O)O)nc2)CC1]

a) step 1: methyl 5-(1-(tert-butoxycarbonyl)-1,2,3,6-tetrahydropyridin-4-yl)picolinate To a solution of methyl 5-bromopicolinate (205 mg, 930 μmol) in DMF (2 ml) under nitrogen at room temperature, was added tert-butyl 4-(4,4,5,5-tetramethyl-1,3,2-dioxa-borolan-2-yl)-5,6-dihydropyridine-1(2H)-carboxylate (300 mg, 970 μmol), followed by sodium carbonate 2M aq. (650 μl, 1.3 mmol). The reaction mixture was degassed with argon for 10 minutes. Finally, dichloro[1,1'-bis(diphenyl-phosphino)ferrocene]palladium(II) dichloromethane adduct (30.5 mg, 41.7 μmol) was added and the mixture was then stirred at 60° C. in microwave for 10 minutes, and then 70° C. for 70 minutes. Ethyl acetate and water were added to the reaction mixture. Both layers were separated and the aqueous layer was extracted two times with ethyl acetate. The combined organic layers were dried over sodium sulfate, filtered and concentrated in vacuo. The crude brown oil was purified with flash column chromatography on silica (Eluent: Heptane/ethyl acetate 0 to 20) to provide 202 mg (68%) of the title compound as a white solid. MS (m/e): 319.5 (M+H−56)

b) step 2: 4-(1-(tert-butoxycarbonyl)-1,2,3,6-tetra-hydropyridin-4-yl)-2-fluorobenzoic acid In analogy to the procedure described for the synthesis of example C.1 (step: 2), the title compound was prepared from methyl 5-(1-(tert-butoxycarbonyl)-1,2,3,6-tetrahydropyri-din-4-yl)picolinate.

Example C.15

Preparation of 6-(4-(tert-butoxycarbonyl)piperazin-1-yl)-2-methoxynicotinic acid

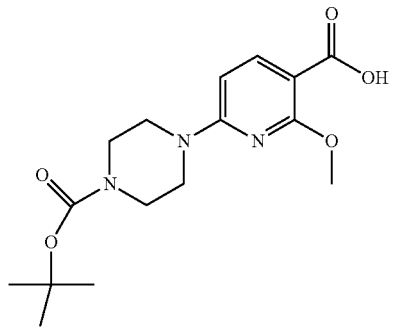 [SMILES: COc1nc(N2CCN(C(=O)OC(C)(C)C)CC2)ccc1C(=O)O]

a) Step 1: tert-butyl 4-(6-fluoro-5-(methoxycarbo-nyl)pyridin-2-yl)piperazine-1-carboxylate To an ice-cold solution of methyl 2,6-difluoronicotinate (2.0 g, 11.6 mmol, CAS 11767-02-0) and triethylamine (1.6 ml, 11.6 mmol) in DMF (10 ml) was added dropwise a solution of tert-butyl piperazine-1-carboxylate (2.2 g, 11.6 mmol) in DMF (5 ml). The reaction was stirred for 0.5 h at 0° C. after which time it was diluted with ethyl acetate, washed with water, brine, dried over sodium sulfate, filtered and concentrated in vacuo. The crude oil was purified with flash column chromatography on silica (Eluent: Heptane/ethyl acetate 10 to 20%) to provide 2.7 g (68%) of the title compound as a white solid. MS (m/e): 340.2 (M+H).

b) Step 2: tert-butyl 4-(6-methoxy-5-(methoxycarbonyl)pyridin-2-yl)piperazine-1-carboxylate To a solution of tert-butyl 4-(6-fluoro-5-(methoxycarbonyl)pyridin-2-yl)piperazine-1-carboxylate (0.40 g, 1.2 mmol) in methanol (5 ml) was added potassium tert-butoxide (0.13 g, 1.2 mmol) and the mixture heated to reflux. After 4 h the reaction was diluted with dichloromethane, washed with brine, dried over sodium sulfate, filtered and concentrated in vacuo to provide 0.4 g (92%) of the title compound as a white solid. MS (m/e): 352.4 (M+H).

c) Step 3: 6-(4-(tert-butoxycarbonyl)piperazin-1-yl)-2-methoxynicotinic acid To a solution of tert-butyl 4-(6-methoxy-5-(methoxycarbonyl)pyridin-2-yl)piperazine-1-carboxylate (0.38 g, 1.1 mmol) in methanol (5 ml) was added 6 N sodium hydroxide (0.36 ml, 2.2 mmol) and the reaction heated to 80° C. for 16 h. The reaction was concentrated to dryness, 5% aqueous citric acid was added and the resulting precipitate isolated by filtration, affording 0.31 g (86%) of the title compound as a white solid. MS (m/e): 338.3 (M+H).

Example C.16

Preparation of 6-(4-(tert-butoxycarbonyl)piperazin-1-yl)-2-fluoronicotinic acid

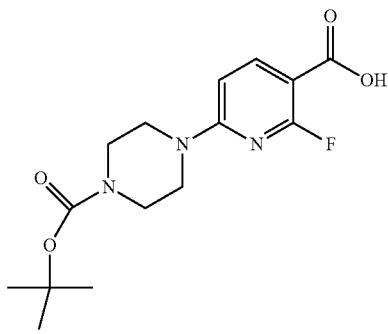 [SMILES: CC(C)(C)OC(=O)N1CCN(c2ccc(C(=O)O)c(F)n2)CC1]

To a suspension of tert-butyl 4-(6-fluoro-5-(methoxycarbonyl)pyridin-2-yl)piperazine-1-carboxylate (0.1 g, 0.3 mmol)-Example C.15 (step 1) in tert-butanol (2 ml) was added 6 N sodium hydroxide (0.1 ml, 0.6 mmol) and the mixture heated to 100° C. for 3 h. The reaction was concentrated to dryness, 5% aqueous citric acid was added and the resulting precipitate isolated by filtration, affording 0.08 g (87%) of the title compound as a white solid. MS (m/e): 326.4 (M+H).

Example C.17

Preparation of 6-(4-(tert-butoxycarbonyl)piperazin-1-yl)-4-fluoronicotinic acid

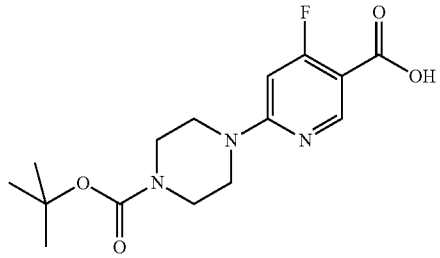 [SMILES: CC(C)(C)OC(=O)N1CCN(c2cc(F)c(C(=O)O)cn2)CC1]

a) Step 1: tert-butyl 4-(4-fluoropyridin-2-yl)piperazine-1-carboxylate

In analogy to the procedure described for the synthesis of example C.1 (step 1), the title compound was prepared from 2-chloro-4-fluoropyridine and (tert-butyl piperazine-1-carboxylate. MS (m/e): 282.5 (M+H).

b) Step 2: tert-butyl 4-(4-fluoro-5-iodopyridin-2-yl)piperazine-1-carboxylate To a solution of tert-butyl 4-(4-fluoropyridin-2-yl)piperazine-1-carboxylate (67 mg, 0.2 mmol) in DMF (0.5 ml) was added N-iodo-succinamide (82 mg, 0.4 mmol) and the mixture stirred for 24 h. The reaction was then diluted with water, extracted with ethyl acetate, the organic phase was washed with brine, dried over sodium sulfate, filtered and concentrated in vacuo. The crude oil was purified with flash column chromatography on silica (Eluent: Heptane/ethyl acetate 0 to 30%) to provide 73 mg (75%) of the title compound as a light yellow solid. MS (m/e): 408.5 (M+H).

c) Step 3: 6-(4-(tert-butoxycarbonyl)piperazin-1-yl)-4-fluoronicotinic acid

To an ice-cold suspension of tert-butyl 4-(4-fluoro-5-iodopyridin-2-yl)piperazine-1-carboxylate (63 mg, 0.2 mmol) in tetrahydrofuran (0.2 ml) under argon was added isopropylmagnesium chloride lithium chloride complex (0.13 ml, 1.3 M in THF, 0.2 mmol). The mixture was allowed to come to ambient temperature and stirred for 45 minutes before carbon dioxide gas was bubbled into the reaction. After 1 h the mixture was diluted with water, extracted with ethyl acetate, the aqueous layer was then acidified with 5% aqueous citric acid solution and re-extracted with ethyl acetate. The ethyl acetate was then washed with brine, dried over sodium sulfate, filtered and concentrated in vacuo to provide 29 mg (58%) of the title compound as an off-white foam. MS (m/e): 326.5 (M+H).

Example C.18

Preparation of 6-(4-(tert-butoxycarbonyl)piperazin-1-yl)-4-methoxynicotinic acid

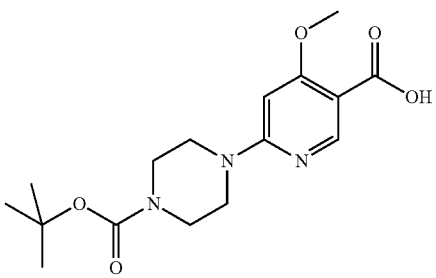 [SMILES: COc1cc(N2CCN(C(=O)OC(C)(C)C)CC2)ncc1C(=O)O]

In analogy to the procedure described for the synthesis of example C.17 (steps: 1-3), the title compound was prepared from 2-chloro-4-methoxypyridine. MS (m/e): 338.6 (M+H).

Example C.19

Preparation of 6-(4-(tert-butoxycarbonyl)piperazin-1-yl)-4-ethoxynicotinic acid

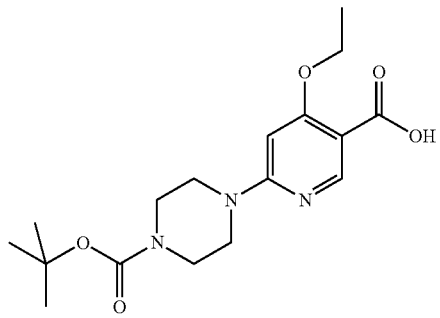 [SMILES: CCOc1cc(N2CCN(C(=O)OC(C)(C)C)CC2)ncc1C(=O)O]

In analogy to the procedure described for the synthesis of example C.17 (steps: 1-3), the title compound was prepared from 2-chloro-4-ethoxypyridine. MS (m/e): 352.5 (M+H).

Example C.20

Preparation of 6-(4-(tert-butoxycarbonyl)piperazin-1-yl)-4-(2,2,2-trifluoroethoxy)nicotinic acid

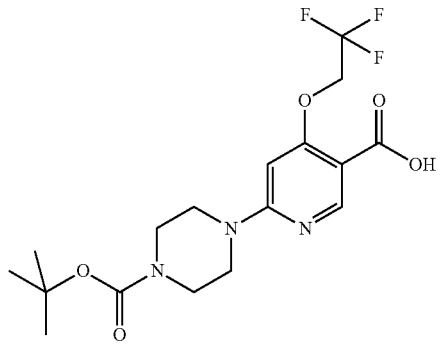 [SMILES: CC(C)(C)OC(=O)N1CCN(c2cc(OCC(F)(F)F)c(C(=O)O)cn2)CC1]

a) Step 1: 2-chloro-4-(2,2,2-trifluoroethoxy)pyridine

To a solution of 2-chloro-4-nitropyridine (0.5 g, 3.2 mmol) in tetrahydrofuran (20 ml) was added 2,2,2-trifluoroethanol (0.25 ml, 3.5 mmol) and potassium tert-butoxide (0.4 g, 3.5 mmol). The reaction mixture was stirred at 60° C. overnight in a sealed vessel. The reaction was concentrated to dryness, the residue re-dissolved in ethyl acetate, washed with sodium hydrogen carbonate, brine, dried over sodium sulfate, filtered and concentrated in vacuo. The crude oil was purified with flash column chromatography on silica (Eluent: Heptane/ethyl acetate 0 to 30%) to provide 0.6 g (91%) of the title compound as a colourless liquid. MS (m/e): 212.2 (M+H).

b) 6-(4-(tert-butoxycarbonyl)piperazin-1-yl)-4-(2,2,2-trifluoroethoxy)nicotinic acid In analogy to the procedure described for the synthesis of example C.17 (steps: 1-3), the title compound was prepared from 2-chloro-4-(2,2,2-trifluoroethoxy)pyridine. MS (m/e): 406.6 (M+H).

Example C.21

Preparation of 6-(4-(tert-butoxycarbonyl)piperazin-1-yl)-2-ethoxynicotinic acid

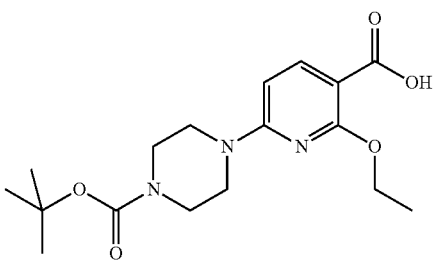 [SMILES: CCOc1nc(N2CCN(C(=O)OC(C)(C)C)CC2)ccc1C(=O)O]

In analogy to the procedure described for the synthesis of example C.15 (steps: 1-3), except that ethanol is used in place of methanol as solvent in step 2, afforded the title compound. MS (m/e): 352.5 (M+H).

Example C.22

Preparation of 6-(4-(tert-butoxycarbonyl)piperazin-1-yl)-2-(2,2,2-trifluoroethoxy)nicotinic acid

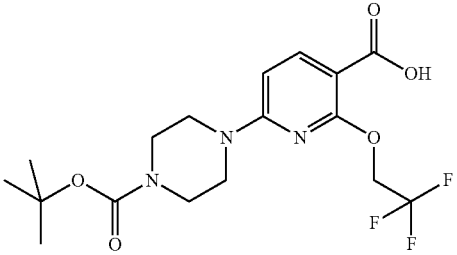 [SMILES: CC(C)(C)OC(=O)N1CCN(c2ccc(C(=O)O)c(OCC(F)(F)F)n2)CC1]

In analogy to the procedure described for the synthesis of example C.15 (steps: 1-3), except that 2,2,2-trifluoroethanol is used in place of methanol as solvent in step 2, afforded the title compound. MS (m/e): 404.7 (M−H).

Example C.23

Preparation of rac-6-(4-(tert-butoxycarbonyl)-3-methylpiperazin-1-yl)-2-methoxynicotinic acid

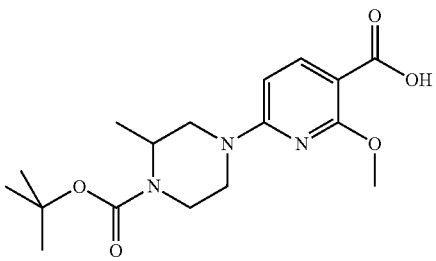 [SMILES: COc1nc(N2CCN(C(=O)OC(C)(C)C)C(C)C2)ccc1C(=O)O]

In analogy to the procedure described for the synthesis of example C.15 (steps: 1-3), the title compound was prepared from rac-tert-butyl 2-methylpiperazine-1-carboxylate and methyl 2,6-difluoronicotinate. MS (m/e): 350.5 (M−H).

Example C.24

Preparation of 6-(4-(tert-butoxycarbonyl)-3,3-dimethylpiperazin-1-yl)-2-methoxynicotinic acid

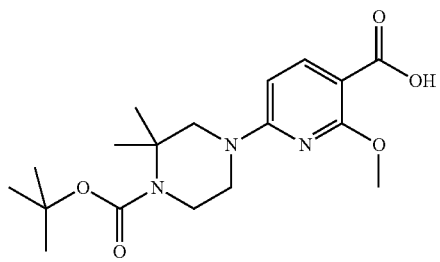 [SMILES: COc1nc(N2CCN(C(=O)OC(C)(C)C)C(C)(C)C2)ccc1C(=O)O]

In analogy to the procedure described for the synthesis of example C.15 (steps: 1-3), the title compound was prepared from 2,2-dimethyl-piperazine-1-carboxylic acid tert-butyl ester and methyl 2,6-difluoronicotinate. MS (m/e): 364.5 (M−H).

Example C.25

Preparation of rac-6-(4-(tert-butoxycarbonyl)-3-methylpiperazin-1-yl)-4-methoxynicotinic acid

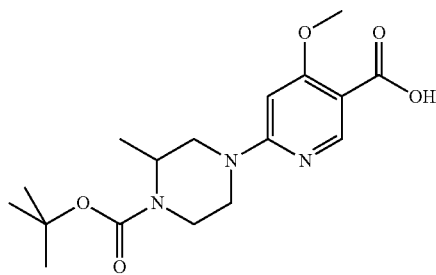 [SMILES: COc1cc(N2CCN(C(=O)OC(C)(C)C)C(C)C2)ncc1C(=O)O]

In analogy to the procedure described for the synthesis of example C.18, the title compound was prepared from rac-tert-butyl 2-methylpiperazine-1-carboxylate and 2-chloro-4-methoxypyridine. MS (m/e): 352.5 (M+H).

DESCRIPTION OF EXAMPLES

Example 1

Preparation of N-(6,8-dimethylimidazo[1,2-a]pyrazin-2-yl)-4-(piperazin-1-yl)benzamide

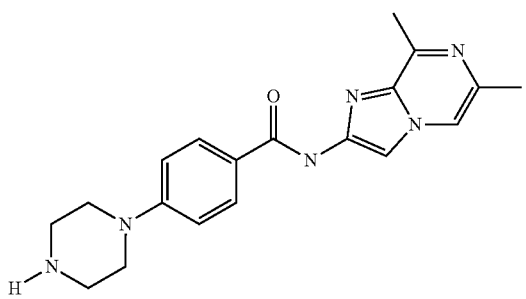 [SMILES: Cc1cn2cc(NC(=O)c3ccc(N4CCNCC4)cc3)nc2c(C)n1]

To a solution of N-(6,8-dimethylimidazo[1,2-a]pyrazin-2-yl)-4-fluorobenzamide (Example A.1) (20 mg, 70.4 µmol) in N,N-dimethylacetamide (200 µl) under nitrogen at room temperature, was added piperazine (60.6 mg, 704 µmol). The reaction mixture was microwaved at 160° C. for 90 minutes. The mixture was cooled to room temperature. The resulting precipitate was filtered, rinsed with diethyl ether and dried to provide 4 mg (16.2%) of the title as an off-white solid. MS (m/e): 351.4 (M+H+)

In analogy to Example 1, compounds 2 to 30 of the following table were prepared by reacting an halo-substituted amide derivative with an amino-substituted derivative at the indicated temperature:

| Example No. | Structure | Systematic Name | Starting materials | T (° C.) | MW found (MH+) |
|---|---|---|---|---|---|
| 2 | 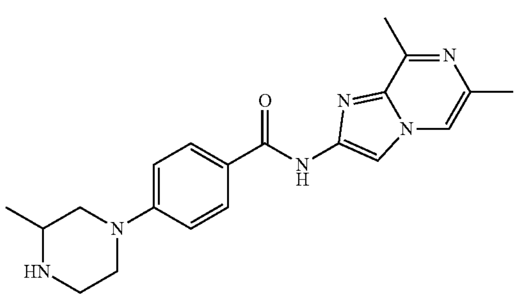 | rac-N-(6,8-dimethyl-imidazo[1,2-a]-pyrazin-2-yl)-4-(3-methylpiperazin-1-yl)benzamide | N-(6,8-dimethyl-imidazo[1,2-a]-pyrazin-2-yl)-4-fluorobenzamide (Example A.1) and rac-2-methyl-piperazine (commercial) | 160 | 365.5 |

-continued

| Example No. | Structure | Systematic Name | Starting materials | T (° C.) | MW found (MH+) |
|---|---|---|---|---|---|
| 3 | 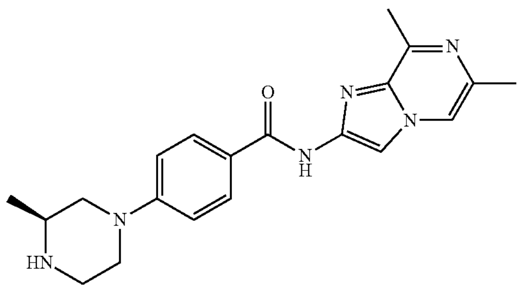 | N-(6,8-Dimethyl-imidazo[1,2-a]-pyrazin-2-yl)-4-((S)-3-methyl-piperazin-1-yl)-benzamide | N-(6,8-dimethyl-imidazo[1,2-a]-pyrazin-2-yl)-4-fluorobenzamide (Example A.1) and (S)-(+)-2-methylpiperazine (commercial) | 200 | 365.5 |
| 4 | 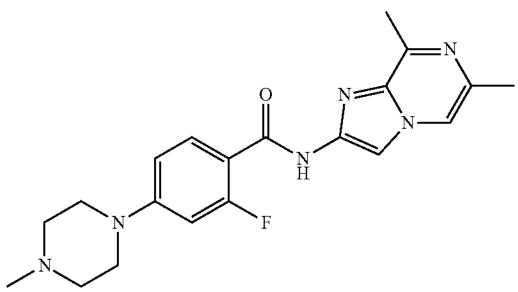 | N-(6,8-dimethyl-imidazo[1,2-a]-pyrazin-2-yl)-2-fluoro-4-(4-methylpiperazin-1-yl)benzamide | N-(6,8-dimethyl-imidazo[1,2-a]-pyrazin-2-yl)-2,4-difluoro-benzamide (Example A2) and 1-methyl-piperazine (commercial) | 180 | 383.5 |
| 5 | 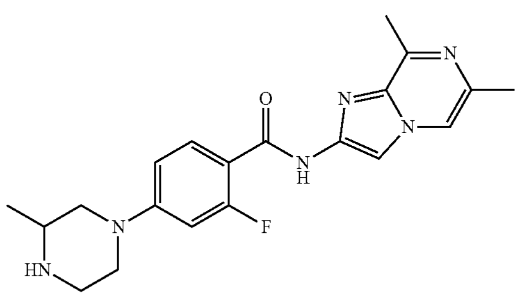 | rac-N-(6,8-dimethyl-imidazo[1,2-a]-pyrazin-2-yl)-2-fluoro-4-(3-methyl-piperazin-1-yl)-benzamide | N-(6,8-dimethyl-imidazo[1,2-a]-pyrazin-2-yl)-2,4-difluorobenz-amide (Example A2) and rac-2-methylpiperazine (commercial) | 180 | 383.5 |
| 6 | 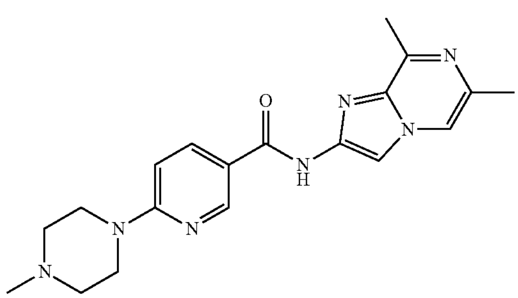 | N-(6,8-dimethyl-imidazo[1,2-a]-pyrazin-2-yl)-6-(4-methyl-piperazin-1-yl)nicotinamide | 6-chloro-N-(6,8-dimethylimidazo-[1,2-a]pyrazin-2-yl)nicotinamide (Example A3) and 1-methylpiperazine (commercial) | 120 | 366.5 |
| 7 | 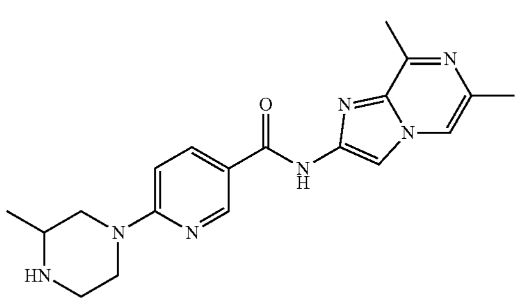 | rac-N-(6,8-dimethyl-imidazo[1,2-a]-pyrazin-2-yl)-6-(3-methyl-piperazin-1-yl)nicotinamide | 6-chloro-N-(6,8-dimethylimidazo-[1,2-a]pyrazin-2-yl)nicotinamide (Example A3) and rac-2-methyl-piperazine (commercial) | 180 | 366.5 |

-continued

| Example No. | Structure | Systematic Name | Starting materials | T (° C.) | MW found (MH+) |
|---|---|---|---|---|---|
| 8 | 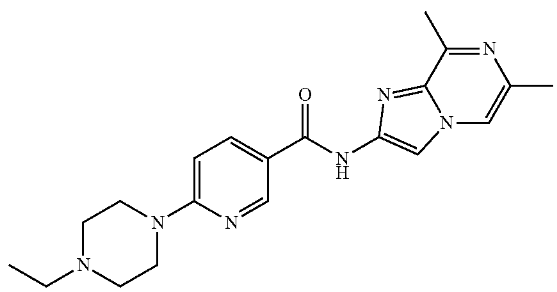 [SMILES: CCN1CCN(c2ccc(C(=O)Nc3cn4cc(C)nc(C)c4n3)cn2)CC1] | N-(6,8-dimethyl-imidazo[1,2-a]-pyrazin-2-yl)-6-(4-ethyl-piperazin-1-yl)nicotinamide | 6-chloro-N-(6,8-dimethylimidazo-[1,2-a]pyrazin-2-yl)nicotinamide (Example A3) and 1-ethylpiperazine (commercial) | 130 | 380.5 |
| 9 | 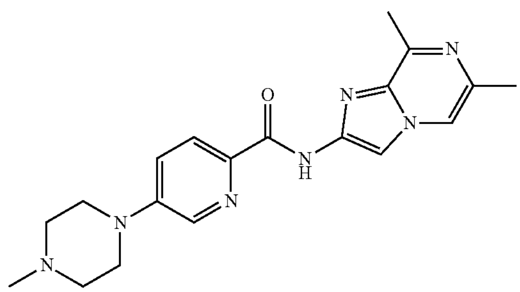 | N-(6,8-dimethyl-imidazo[1,2-a]-pyrazin-2-yl)-5-(4-methyl-piperazin-1-yl)picolinamide | N-(6,8-dimethyl-imidazo[1,2-a]-pyrazin-2-yl)-5-fluoropicolinamide (Example A4) and 1-methylpiperazine (commercial) | 160 | 366.5 |
| 10 | 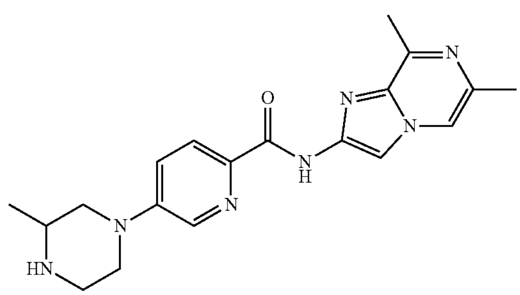 | rac-N-(6,8-dimethyl-imidazo[1,2-a]-pyrazin-2-yl)-5-(3-methyl-piperazin-1-yl)picolinamide | N-(6,8-dimethyl-imidazo[1,2-a]-pyrazin-2-yl)-5-fluoropicolinamide (Example A4) and rac-2-methyl-piperazine (commercial) | 160 | 366.5 |
| 11 | 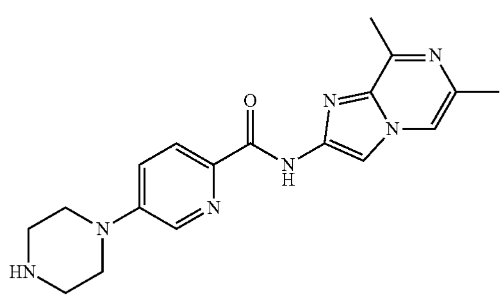 [SMILES: Cc1cn2cc(NC(=O)c3ccc(N4CCNCC4)cn3)nc2c(C)n1] | N-(6,8-dimethyl-imidazo[1,2-a]-pyrazin-2-yl)-5-(piperazin-1-yl)picolinamide | N-(6,8-dimethyl-imidazo[1,2-a]-pyrazin-2-yl)-5-fluoropicolinamide (Example A4) and piperazine (commercial) | 160 | 352.5 |
| 12 | 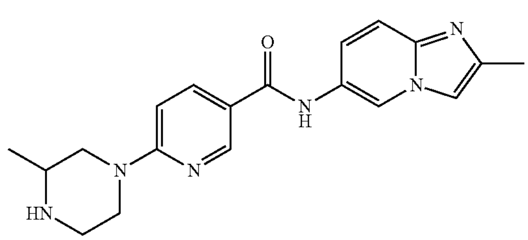 | rac-N-(2-methyl-imidazo[1,2-a]-pyridin-6-yl)-6-(3-methyl-piperazin-1-yl)nicotinamide | 6-chloro-N-(2-methylimidazo-[1,2-a]pyridin-6-yl)nicotinamide (Example A5) and rac-2-methyl-piperazine (commercial) | 130 | 351.4 |

-continued

| Example No. | Structure | Systematic Name | Starting materials | T (° C.) | MW found (MH+) |
|---|---|---|---|---|---|
| 13 | 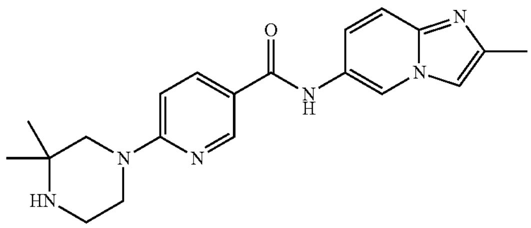 | 6-(3,3-dimethyl-piperazin-1-yl)-N-(2-methyl-imidazo[1,2-a]-pyridin-6-yl)-nicotinamide | 6-chloro-N-(2-methylimidazo-[1,2-a]pyridin-6-yl)nicotinamide (Example A5) and 2,2-Dimethyl-piperazine (commercial) | 130 | 365.5 |
| 14 | 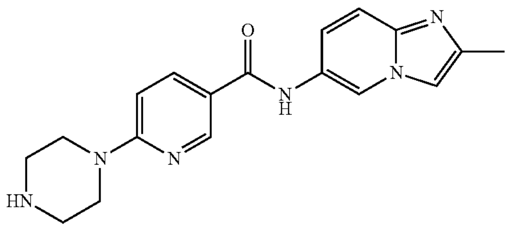 [SMILES: Cc1cn2cc(NC(=O)c3ccc(N4CCNCC4)nc3)ccc2n1] | N-(2-methyl-imidazo[1,2-a]-pyridin-6-yl)-6-(piperazin-1-yl)nicotinamide | 6-chloro-N-(2-methylimidazo-[1,2-a]pyridin-6-yl)nicotinamide (Example A5) and piperazine (commercial) | 130 | 337.5 |
| 15 | 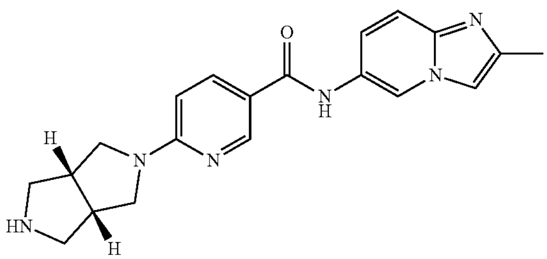 [SMILES: Cc1cn2cc(NC(=O)c3ccc(N4C[C@H]5CNC[C@H]5C4)nc3)ccc2n1] | 6-hexahydro-pyrrolo[3,4-c]-pyrrol-2(1H)-yl)-N-(2-methyl-imidazo[1,2-a]-pyridin-6-yl)-nicotinamide hydrochloride | 6-chloro-N-(2-methylimidazo-[1,2-a]pyridin-6-yl)nicotinamide (Example A5) and hexahydropyrrolo-[3,4-c]pyrrole-2-carboxylic acid tert-butylester (commercial) followed by treatment with HCl | 130 | 363.5 |
| 16 | 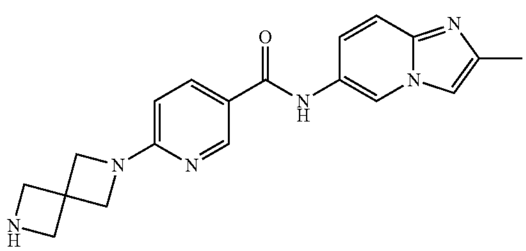 [SMILES: Cc1cn2cc(NC(=O)c3ccc(N4CC5(CNC5)C4)nc3)ccc2n1] | N-(2-methyl-imidazo[1,2-a]-pyridin-6-yl)-6-(2,6-diazaspiro-[3.3]heptan-2-yl)nicotinamide hydrochloride with HCl | 6-chloro-N-(2-methylimidazo-[1,2-a]pyridin-6-yl)nicotinamide (Example A5) and 2,6-Diazaspiro-[3.3]heptane-2-carboxylic acid tert-butyl ester (commercial) followed by treatment | 130 | 349.5 |
| 17 | 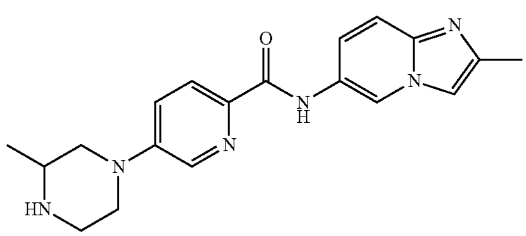 | rac-N-(2-methyl-imidazo[1,2-a]-pyridin-6-yl)-5-(3-methyl-piperazin-1-yl)-picolinamide | 5-fluoro-N-(2-methylimidazo-[1,2-a]pyridin-6-yl)picolinamide (Example A6) and rac-2-methyl-piperazine (commercial) | 160 | 351.5 |
| 18 | 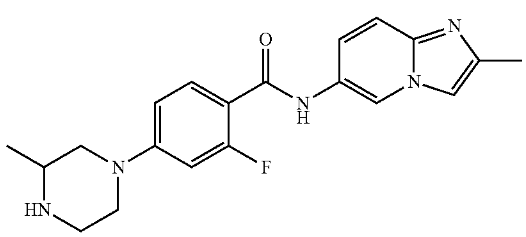 | rac-2-fluoro-N-(2 methylimidazo-[1,2-a]pyridin-6-yl)-4(3-methyl-piperazin-1-yl)-benzamide | 2,4-difluoro-N-(2-methylimidazo-[1,2-a]pyridin-6-yl)benzamide (Example A7) and rac-2-methyl-piperazine (commercial) | 100 | 368.5 |

| Example No. | Structure | Systematic Name | Starting materials | T (° C.) | MW found (MH+) |
|---|---|---|---|---|---|
| 19 | 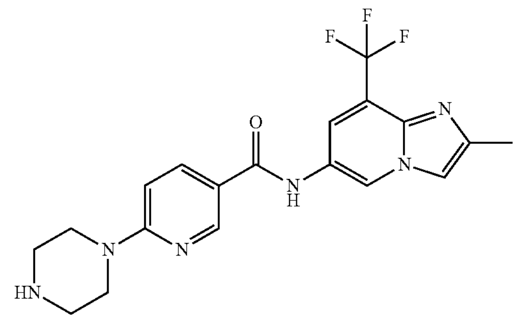 [SMILES: Cc1cn2cc(NC(=O)c3ccc(N4CCNCC4)nc3)cc(C(F)(F)F)c2n1] | N-(2-methyl-8-(trifluoromethyl)-imidazo[1,2-a]-pyridin-6-yl)-6-(piperazin-1-yl)-nicotinamide | 6-Chloro-N-(2-methyl-8-trifluoromethyl-imidazo[1,2-a]-pyridin-6-yl)-nicotinamide (Example A8) and piperazine (commercial) | 130 | 405.4 |
| 20 | 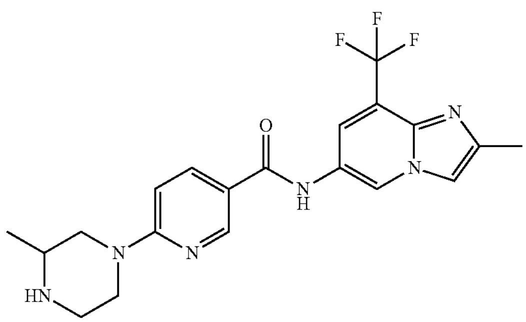 | rac-N-(2-methyl-8-(trifluoromethyl)-imidazo[1,2-a]-pyridin-6-yl)-6-(3-methyl-piperazin-1-yl)-nicotinamide | 6-Chloro-N-(2-methyl-8-trifluoromethyl-imidazo[1,2-a]-pyridin-6-yl)-nicotinamide (Example A8) and rac-2-methyl-piperazine (commercial) | 130 | 419.4 |
| 21 | 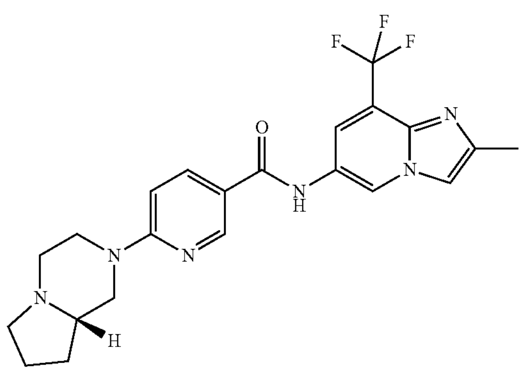 [SMILES: Cc1cn2cc(NC(=O)c3ccc(N4CCN5CCC[C@H]5C4)nc3)cc(C(F)(F)F)c2n1] | (S)-6-(hexahydro-pyrrolo[1,2-a]-pyrazin-2(1H)-yl)-N-(2-methyl-8-(trifluoromethyl)-imidazo[1,2-a]-pyridin-6-yl)-nicotinamide | 6-Chloro-N-(2-methyl-8-trifluoromethyl-imidazo[1,2-a]-pyridin-6-yl)-nicotinamide (Example A8) and (S)-octahydro-pyrrolo[1,2-a]-pyrazine (commercial) | 130 | 445.7 |
| 22 | 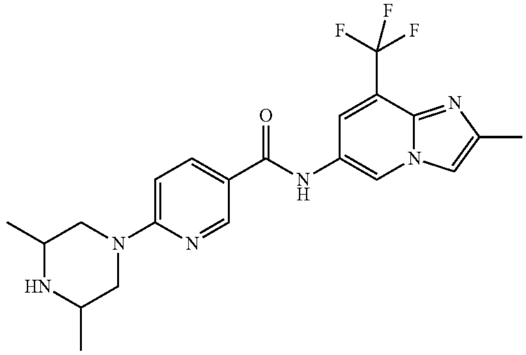 | 6-(3,5-dimethyl-piperazin-1-yl)-N-(2-methyl-8-(trifluoromethyl)-imidazo[1,2-a]-pyridin-6-yl)-nicotinamide | 6-Chloro-N-(2-methyl-8-trifluoro-methylimidazo-[1,2-a]pyridin-6-yl)nicotinamide (Example A8) and 2,6-dimethyl-piperazine | 130 | 433.7 |

-continued

| Example No. | Structure | Systematic Name | Starting materials | T (° C.) | MW found (MH+) |
|---|---|---|---|---|---|
| 23 | 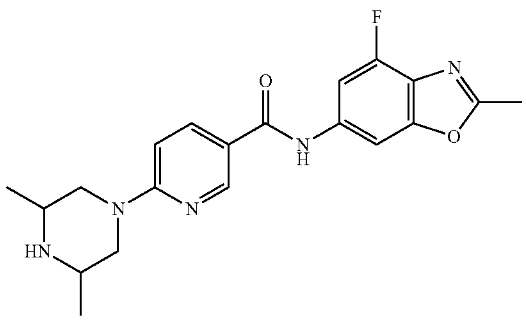 | 6-(3,5-dimethyl-piperazin-1-yl)-N-(4-fluoro-2-methylbenzo[d]-oxazol-6-yl)-nicotinamide | 6-chloro-N-(4-fluoro-2-methyl-benzo[d]oxazol-6-yl)nicotinamide (Example A9) and 2,6-dimethyl-piperazine | 130 | 384.6 |
| 24 | 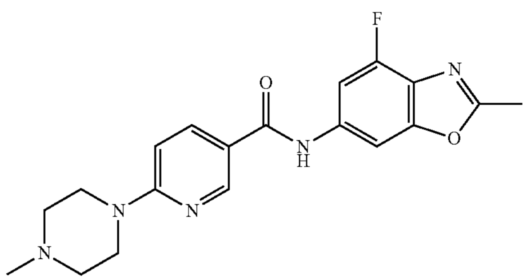 | N-(4-fluoro-2-methylbenzo[d]-oxazol-6-yl)-6-(4-methylpiperazin-1-yl)nicotinamide | 6-chloro-N-(4-fluoro-2-methyl-benzo[d]oxazol-6-yl)nicotinamide (Example A9) and 1-methylpiperazine (commercial) | 130 | 370.6 |
| 25 | 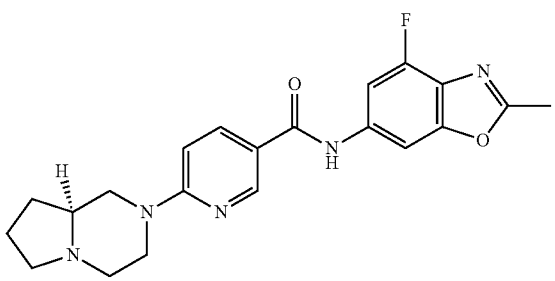 [SMILES: Cc1nc2c(F)cc(NC(=O)c3ccc(N4CCN5CCC[C@H]5C4)nc3)cc2o1] | (S)-N-(4-fluoro-2-methylbenzo[d]oxazol-6-yl)-6-(hexa-hydropyrrolo[1,2-a]pyrazin-2-(1H)-yl)nicotinamide | 6-chloro-N-(4-fluoro-2-methyl-benzo[d]oxazol-6-yl)nicotinamide (Example A9) and (S)-octahydro-pyrrolo[1,2-a]-pyrazine (commercial) | 130 | 396.6 |
| 26 | 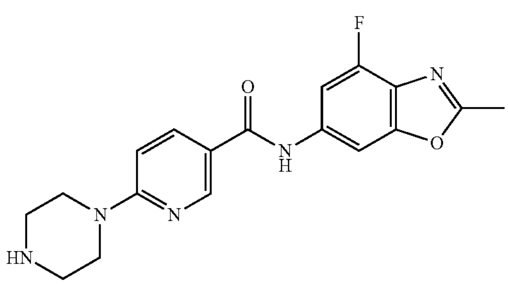 [SMILES: Cc1nc2c(F)cc(NC(=O)c3ccc(N4CCNCC4)nc3)cc2o1] | N-(4-Fluoro-2-methylbenzo-oxazol-6-yl)-6-piperazin-1-yl-nicotinamide | 6-chloro-N-(4-fluoro-2-methyl-benzo[d]oxazol-6-yl)nicotinamide (Example A9) and piperazine (commercial) | 130 | 356.6 |
| 27 | 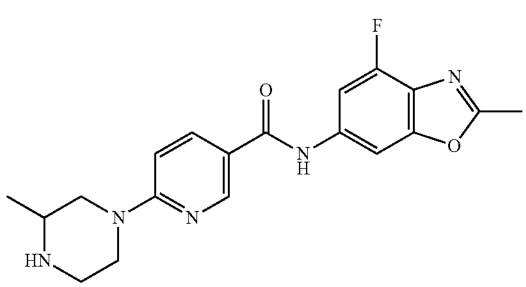 | rac-N-(4-Fluoro-2-methylbenzo-oxazol-6-yl)-6-(3-methylpiperazin-1-yl)nicotinamide | 6-chloro-N-(4-fluoro-2-methyl-benzo[d]oxazol-6-yl)nicotinamide (Example A9) and rac-2-methyl-piperazine (commercial) | 130 | 370.6 |

| Example No. | Structure | Systematic Name | Starting materials | T (° C.) | MW found (MH+) |
|---|---|---|---|---|---|
| 28 | 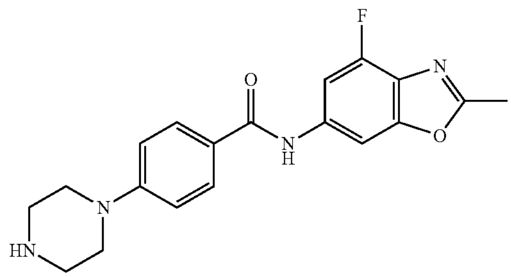 [SMILES: Cc1nc2c(F)cc(NC(=O)c3ccc(N4CCNCC4)cc3)cc2o1] | N-(4-fluoro-2-methylbenzo[d]-oxazol-6-yl)-4-(piperazin-1-yl)benzamide | 4-fluoro-N-(4-fluoro-2-methyl-benzo[d]oxazol-6-yl)benzamide (Example A10) and piperazine (commercial) | 160 | 355.6 |
| 29 | 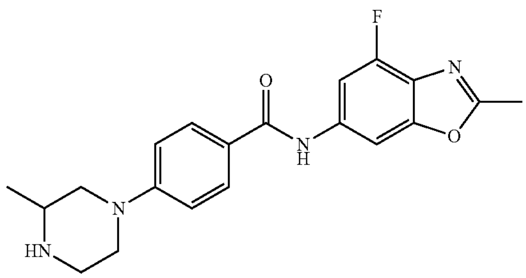 | rac-N-(4-fluoro-2-methylbenzo[d]-oxazol-6-yl)-4-(3-methylpiperazin-1-yl)benzamide | 4-fluoro-N-(4-fluoro-2-methyl-benzo[d]oxazol-6-yl)benzamide (Example A10) and rac-2-methyl-piperazine (commercial) | 160 | 369.6 |
| 30 | 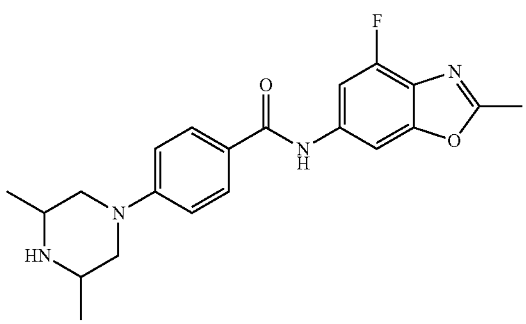 | 4-(3,5-dimethyl-piperazin-1-yl)-N-(4-fluoro-2-methyl-benzo[d]oxazol-6-yl)benzamide | 4-fluoro-N-(4-fluoro-2-methyl-benzo[d]oxazol-6-yl)benzamide (Example A10) and 2,6-dimethyl-piperazine | 160 | 383.7 |

Example 31

(S)-2-fluoro-4-(hexahydropyrrolo[1,2-a]pyrazin-2(1H)-yl)-N-(2-methylimidazo[1,2-a]pyridin-6-yl)benzamide

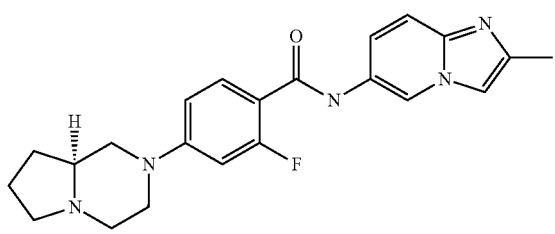 [SMILES: Cc1cn2cc(NC(=O)c3ccc(N4CCN5CCC[C@H]5C4)cc3F)ccc2n1]

To a solution of (S)-2-fluoro-4-(hexahydropyrrolo[1,2-a]pyrazin-2(1H)-yl)benzoic acid (Example C.1) (80 mg, 303 µmol) in N,N-dimethylformamide (800 µl) under nitrogen at room temperature, were added HATU (O-(7-azabenzotri-azol-1-yl)-N,N,N',N'-tetramethyluronium hexafluorophosphate) (173 mg, 454 µmol) and N-ethyldiisopropylamine (156 mg, 206 µl, 1.21 mmol). After 5 minutes stirring at room temperature, 2-methylimidazo[1,2-a]pyridin-6-amine hydrobromide (commercial) (69.0 mg, 303 µmol) was added. The mixture was shaked at 60° C. for 5.5 hours and then at room temperature for two days. The solvent was removed in vacuo. The residue was taken in a saturated aqueous solution of bicarbonate. Ethyl acetate was added. The resulting precipitate was filtered, rinsed with ethyl acetate and dried. The solid was stirred in ethyl acetate, filtered, rinsed with cold ethyl acetate and n-hexane and dried to provide 11 mg (9%) of the title compound as a light brown solid. MS (m/e): 394.6 (M+H)

In analogy to Example 31, compounds 32 to 35 of the following table were prepared from the acid and amine derivatives:

| Expl. No. | Structure | Systematic Name | Starting materials | MW found (MH+) |
|---|---|---|---|---|
| 32 | 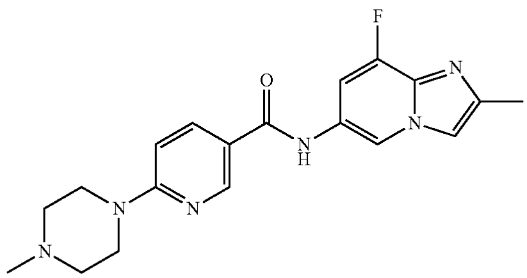 | N-(8-fluoro-2-methylimidazo-[1,2-a]pyridin-6-yl)-6-(4-methyl-piperazin-1-yl)-nicotinamide | 6-(4-Methyl-piperazin-1-yl)-nicotinic acid (commercial) and 8-Fluoro-2-methyl-imidazo-[1,2-a]pyridin-6-ylamine hydrochloride (Example B.4) | 369.5 |
| 33 | 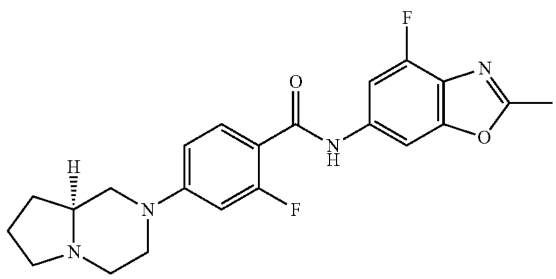 [SMILES: Cc1nc2c(F)cc(NC(=O)c3ccc(N4CCN5CCC[C@H]5C4)cc3F)cc2o1] | (S)-2-Fluoro-N-(4-fluoro-2-methyl-benzooxazol-6-yl)-4-(S)-hexahydro-pyrrolo[1,2-a]-pyrazin-2-yl-benzamide | (S)-2-fluoro-4-(hexahydro-pyrrolo-[1,2-a]-pyrazin-2(1H)-yl)benzoic acid (Example C.1) and 4-fluoro-2-methylbenzo[d]-oxazol-6-amine hydrochloride (Example B.3) | 413.7 |
| 34 | 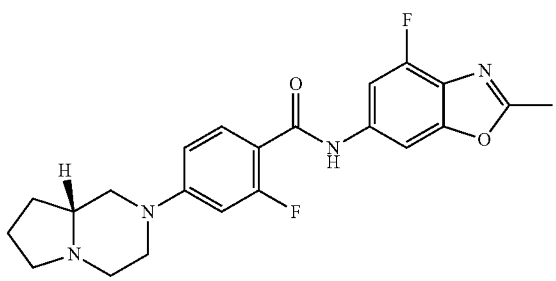 [SMILES: Cc1nc2c(F)cc(NC(=O)c3ccc(N4CCN5CCC[C@@H]5C4)cc3F)cc2o1] | (R)-2-fluoro-N-(4-fluoro-2-methyl-benzo[d]oxazol-6-yl)-4-(hexahydro-pyrrolo[1,2-a]-pyrazin-2(1H)-yl)benzamide | (R)-2-fluoro-4-(hexahydro-pyrrolo-[1,2-a]-pyrazin-2(1H)-yl)benzoic acid (Example C.2) and 4-fluoro-2-methylbenzo[d]-oxazol-6-amine hydrochloride (Example B.3) | 413.6 |
| 35 | 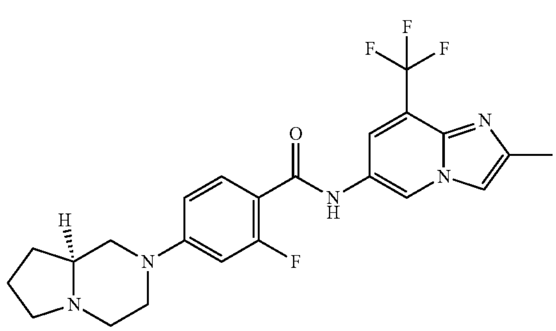 [SMILES: Cc1cn2cc(NC(=O)c3ccc(N4CCN5CCC[C@H]5C4)cc3F)cc(C(F)(F)F)c2n1] | (S)-2-fluoro-4-(hexahydro-pyrrolo[1,2-a]-pyrazin-2(1H)-yl)-N-(2-methyl-8-(trifluoro-methyl)imidazo-[1,2-a]pyridin-6-yl]benzamide | (S)-2-fluoro-4-(hexahydropyrrolo-[1,2-a]pyrazin-2(1H)-yl)benzoic acid (Example C.1) and 2-Methyl-8-trifluoromethyl-imidazo[1,2-a]-pyridin-6-ylamine hydrochloride (Example B.2) | 462.5 |

Example 36

Preparation of N-(8-fluoro-2-methylimidazo[1,2-a]pyridin-6-yl)-4-(piperazin-1-yl)benzamide hydrochloride

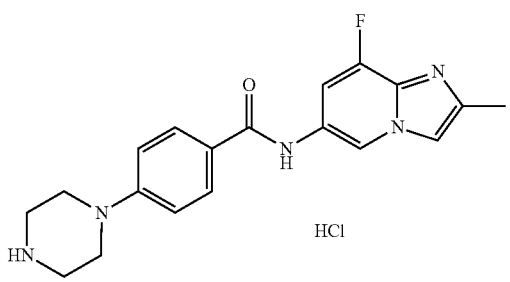 [SMILES: Cc1cn2cc(NC(=O)c3ccc(N4CCNCC4)cc3)cc(F)c2n1 ; Cl]

To a solution of 4-(4-(tert-butoxycarbonyl)piperazin-1-yl)benzoic acid (commercial) (109 mg, 357 μmol) in N,N-dimethylformamide (1.00 ml) under nitrogen at room temperature, were added HATU (O-(7-azabenzotriazol-1-yl)-N,N,N',N'-tetramethyluronium hexafluorophosphate) (204 mg, 536 μmol) and N-ethyldiisopropylamine (185 mg, 243 μl, 1.43 mmol). After 5 minutes stirring at room temperature, 8-fluoro-2-methyl-imidazo[1,2-a]pyridin-6-ylamine hydrochloride (Example B.4) (72 mg, 357 μmol) was added. The mixture was stirred at room temperature for 21 hours and then at 60° C. for 2 hours. The solvent was removed in vacuo. The residue was taken in a saturated aqueous solution of bicarbonate and extracted three times with ethyl acetate. The combined extracts were dried over sodium sulfate, filtered and concentrated in vacuo. The crude oil was purified on silica gel (Eluent: heptane/ethyl acetate 0 to 10%) to provide 78 mg of tert-butyl 4-(4-(8-fluoro-2-methylimidazo[1,2-a]pyridin-6-ylcarbamoyl)phenyl)piperazine-1-carboxylate. To a suspension of this compound (40 mg, 88.2 μmol) in methanol (400 μl) was added HCl 4M in dioxane (221 μl, 882 μmol). The light yellow suspension was stirred at room temperature for 17 hours. The solid was filtered, washed with ether and hexane and dried to provide 25 mg (72.7%) of the title compound as a light yellow solid. MS(m/e): 354.5 (M+H).

In analogy to Example 36, compounds 37 to 63 of the following table were prepared from the acid and amine derivatives followed by treatment with HCl or TFA.

| Expl. No. | Structure | Systematic Name | Starting Materials | MW found (MH+) |
|---|---|---|---|---|
| 37 | 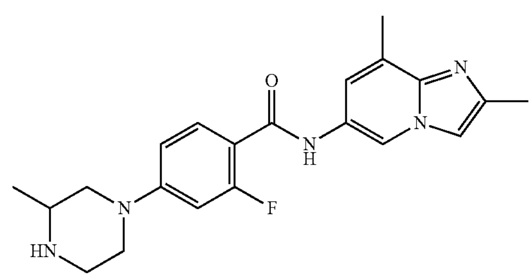 | rac-N-(2,8-dimethyl-imidazo[1,2-a]-pyridin-6-yl)-2-fluoro-4-(3-methylpiperazin-1-yl)benzamide dihydrochloride | 4-(4-(tert-butoxycarbonyl)-3-methylpiperazin-1-yl)-2-fluorobenzoic acid (Example C.3) and 2,8-dimethyl-imidazo[1,2-a]-pyridin-6-amine hydrochloride (CAS: 1216295-25-8) followed by treatment with HCl | 382.6 |
| 38 | 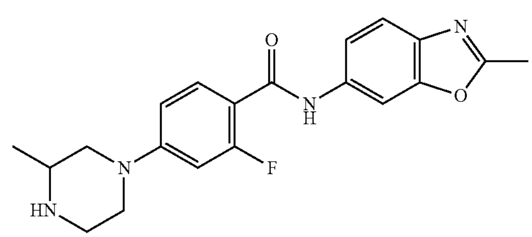 | rac-2-fluoro-N-(2-methylbenzo[d]-oxazol-6-yl)-4-(3-methylpiperazin-1-yl)benzamide dihydrochloride | 4-(4-(tert-butoxycarbonyl)-3-methylpiperazin-1-yl)-2-fluorobenzoic acid (Example C.3) and 2-Methyl-benzooxazol-6-ylamine (commercial) followed by treatment with HCl | 369.5 |
| 39 | 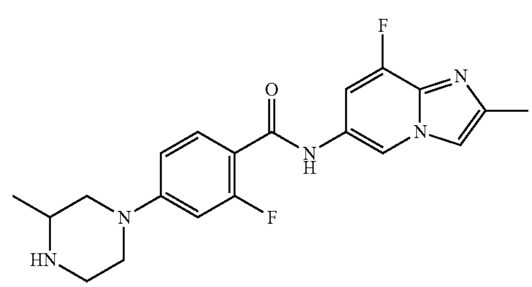 | rac-2-fluoro-N-(8-fluoro-2-methyl-imidazo[1,2-a]-pyridin-6-yl)-4-(3-methylpiperazin-1-yl)benzamide dihydrochloride | 4-(4-(tert-butoxycarbonyl)-3-methylpiperazin-1-yl)-2-fluorobenzoic acid (Example C.3) and 8-Fluoro-2-methyl-imidazo[1,2-a]pyridin-6-ylamine hydrochloride (Example B.4) followed by treatment with HCl | 386.6 |

-continued

| Expl. No. | Structure | Systematic Name | Starting Materials | MW found (MH+) |
|---|---|---|---|---|
| 40 | 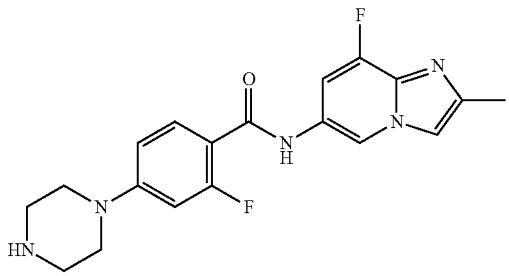 [SMILES: Cc1cn2cc(NC(=O)c3ccc(N4CCNCC4)cc3F)cc(F)c2n1] | 2-fluoro-N-(8-fluoro-2-methyl-imidazo[1,2-a]-pyridin-6-yl)-4-(piperazin-1-yl)benzamide dihydrochloride | 4-(4-(tert-butoxy-carbonyl)piperazin-1-yl)-2-fluorobenzoic acid (CAS: 1121596-45-9) and 8-Fluoro-2-methylimidazo[1,2-a]pyridin-6-ylamine hydrochloride (Example B.4) followed by treatment with HCl | 372.6 |
| 41 | 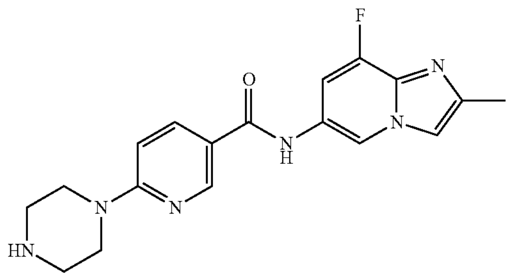 [SMILES: Cc1cn2cc(NC(=O)c3ccc(N4CCNCC4)nc3)cc(F)c2n1] | N-(8-fluoro-2-methylimidazo-[1,2-a]pyridin-6-yl)-6-(piperazin-1-yl)nicotinamide dihydrochloride | 4-(5-Carboxy-pyridin-2-yl)-piperazine-1-carboxylic acid tert-butyl ester (CAS: 201809-22-5) and 8-Fluoro-2-methyl-imidazo[1,2-a]pyridin-6-ylamine hydrochloride (Example B.4) followed by treatment with HCl | 355.5 |
| 42 | 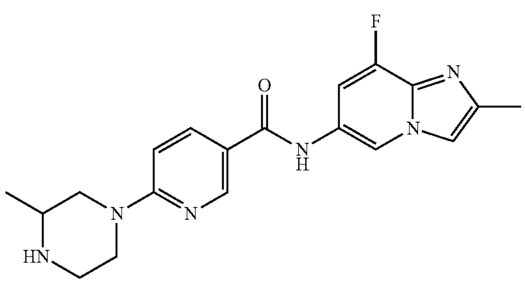 | rac-N-(8-fluoro-2-methylimidazo-[1,2-a]pyridin-6-yl)-6-(3-methyl-piperazin-1-yl)-nicotinamide dihydrochloride | rac-6-(4-(tert-butoxy-carbonyl)-3-methyl-piperazin-1-yl)nicotinic acid (CAS: 904817-70-5) and 8-Fluoro-2-methyl-imidazo[1,2-a]pyridin-6-ylamine hydrochloride (Example B.4) followed by treatment with HCl | 369.6 |
| 43 | 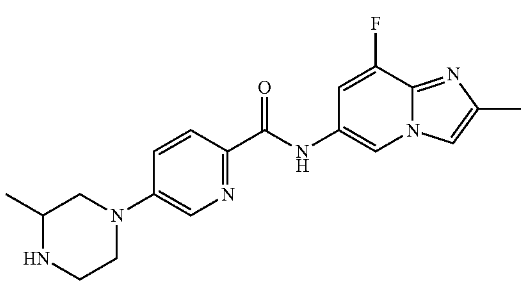 | rac-N-(8-fluoro-2-methylimidazo[1,2-a]pyridin-6-yl)-5-(3-methylpiperazin-1-yl)picolinamide dihydrochloride | rac-4-(6-Carboxy-pyridin-3-yl)-2-methyl-piperazine-1carboxylic acid tert-butyl ester (Example C.4) and 8-Fluoro-2-methyl-imidazo[1,2-a]pyridin-6-ylamine hydrochloride (Example B.4) followed by treatment with HCl | 369.6 |
| 44 | 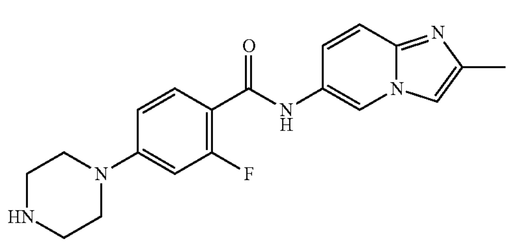 [SMILES: Cc1cn2cc(NC(=O)c3ccc(N4CCNCC4)cc3F)ccc2n1] | 2-fluoro-N-(2-methylimidazo[1,2-a]pyridin-6-yl)-4-(piperazin-1-yl)-benzamidehydro-chloride | 4-(4-(tert-butoxy-carbonyl)piperazin-1-yl)-2-fluorobenzoic acid (CAS: 1121596-45-9) and 2-methyl-imidazo[1,2-a]pyridin-6-amine hydrobromide (commercial) followed by treatment with HCl | 354.6 |

| Expl. No. | Structure | Systematic Name | Starting Materials | MW found (MH+) |
|---|---|---|---|---|
| 45 | 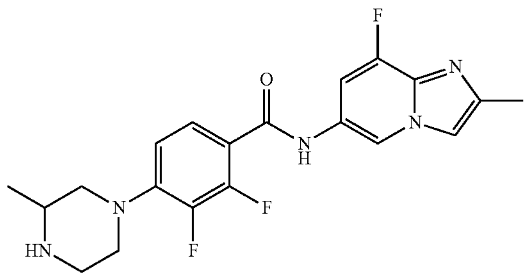 | rac-2,3-difluoro-N-(8-fluoro-2-methylimidazo[1,2-a]pyridin-6-yl)-4-(3-methylpiperazin-1-yl)benzamide hydrochloride | rac-4-(4-(tert-butoxycarbonyl)-3-methylpiperazin-1-yl)-2,3-difluorobenzoic acid (Example C.5) and 8-Fluoro-2-methylimidazo[1,2-a]pyridin-6-ylamine hydrochloride (Example B.4) followed by treatment with HCl | 404.6 |
| 46 | 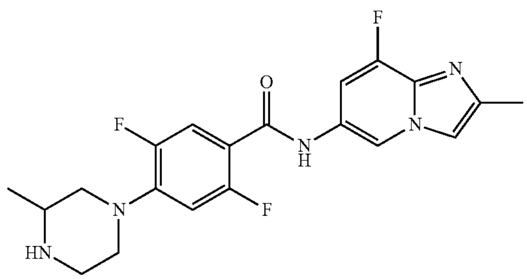 | rac-2,5-difluoro-N-(8-fluoro-2-methyl-imidazo[1,2-a]-pyridin-6-yl)-4-(3-methylpiperazin-1-yl)benzamide hydrochloride | rac-4-(4-Carboxy-2,5-difluoro-phenyl)-2-methylpiperazine-1-carboxylic acid tert-butyl ester (Example C.6) and 8-Fluoro-2-methylimidazo[1,2-a]pyridin-6-ylamine hydrochloride (Example B.4) followed by treatment with HCl | 404.5 |
| 47 | 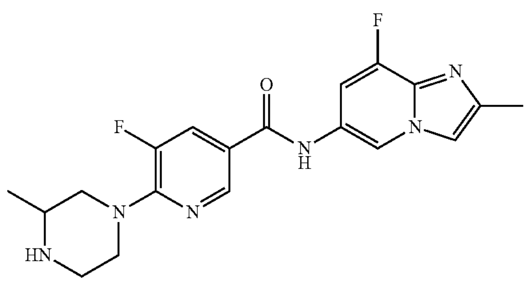 | rac-5-fluoro-N-(8-fluoro-2-methyl-imidazo[1,2-a]-pyridin-6-yl)-6-(3-methylpiperazin-1-yl)nicotinamide hydrochloride | rac-6-(4-(tertbutoxycarbonyl)-3-methyl-piperazin-1-yl)-5-fluoronicotinic acid (Example C.7) and 8-Fluoro-2-methyl-imidazo[1,2-a]pyridin-6-ylamine hydrochloride (Example B.4) followed by treatment with HCl | 387.5 |
| 48 | 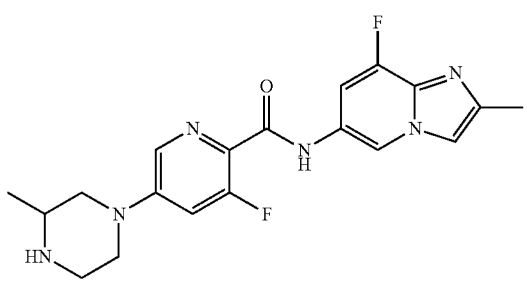 | rac-3-fluoro-N-(8-fluoro-2-methyl-imidazo[1,2-a]-pyridin-6-yl)-5-(3-methylpiperazin-1-yl)picolinamide hydrochloride | rac-5-(4-(tertbutoxycarbonyl)-3-methyl-piperazin-1-yl)-3-fluoropicolinic acid (Example C.8) and 8-Fluoro-2-methyl-imidazo[1,2-a]pyridin-6-ylamine hydrochloride (Example B.4) followed by treatment with HCl | 387.6 |
| 49 | 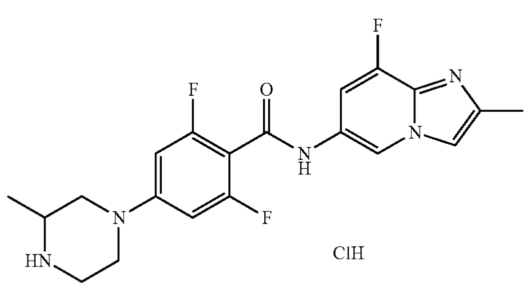 | rac-2,6-difluoro-N-(8-fluoro-2-methyl-imidazo[1,2-a]-pyridin-6-yl)-4-(3-methylpiperazin-1-yl)benzamide hydrochloride | rac-4-(4-(tertbutoxycarbonyl)-3-methyl-piperazin-1-yl)-2,6-difluorobenzoic acid (Example C.9) and 8-Fluoro-2-methyl-imidazo[1,2-a]-pyridin-6-ylamine hydrochloride (Example B.4) followed by treatment with HCl | 404.6 |

| Expl. No. | Structure | Systematic Name | Starting Materials | MW found (MH+) |
|---|---|---|---|---|
| 50 | 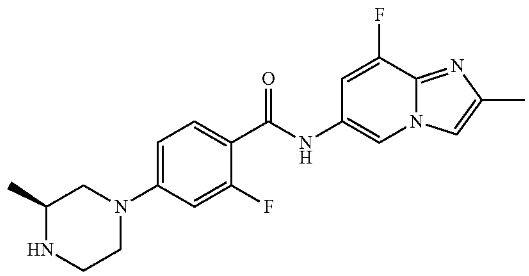 | (S)-2-fluoro-N-(8-fluoro-2-methyl-imidazo[1,2-a]-pyridin-6-yl)-4-(3-methylpiperazin-1-yl)benzamide hydrochloride | (S)-4-(4-(tertbutoxy-carbonyl)-3-methyl-piperazin-1-yl)-2-fluorobenzoic acid (Example C.10) and 8-Fluoro-2-methyl-imidazo[1,2-a]pyridin-6-ylamine hydrochloride (Example B.4) followed by treatment with HCl | 386.6 |
| 51 | 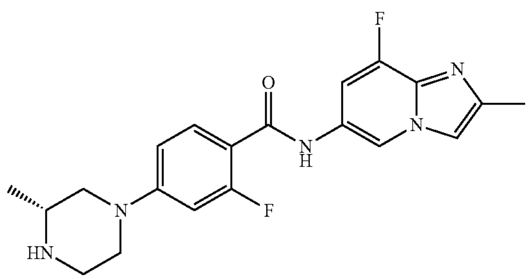 | (R)-2-fluoro-N-(8-fluoro-2-methyl-imidazo[1,2-a]-pyridin-6-yl)-4-(3-methylpiperazin-1-yl)benzamide hydrochloride | (R)-4-(4-(tertbutoxy-carbonyl)-3-methyl-piperazin-1-yl)-2-fluorobenzoic acid (Example C.11) and 8-Fluoro-2-methyl-imidazo[1,2-a] pyridin-6-ylamine hydrochloride (Example B.4) followed by treatment with HCl | 386.6 |
| 52 | 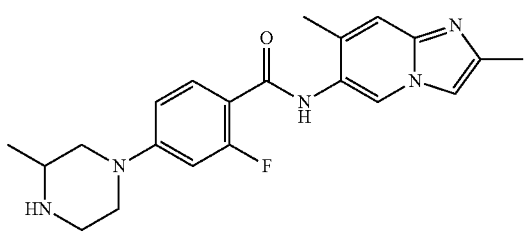 | rac-N-(2,7-dimethyl-imidazo[1,2-a]-pyridin-6-yl)-2-fluoro-4-(3-methyl-piperazin-1-yl)-benzamide dihydrochloride | rac-4-(4-(tert-butoxy-carbonyl)-3-methyl-piperazin-1-yl)-2-fluorobenzoic acid (Example C.3) and 2,7-dimethylimidazo-[1,2-a]pyridin-6-amine hydrochloride (CAS: 1216109-27-1) followed by treatment with HCl | 382.5 |
| 53 | 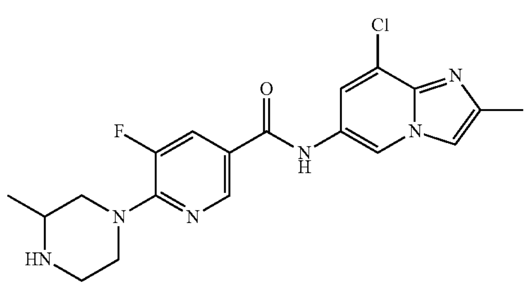 | rac-N-(8-chloro-2-methylimidazo-[1,2-a]pyridin-6-yl)-5-fluoro-6-(3-methylpiperazin-1-yl)nicotinamide hydrochloride | rac-6-(4-(tertbutoxy-carbonyl)-3-methyl-piperazin-1-yl)-5-fluoronicotinic acid (Example C.7) and 8-chloro-2-methyl-imidazo[1,2-a]pyridin-6-amine hydrochloride (Example B.5) followed by treatment with HCl | 403.5 |
| 54 | 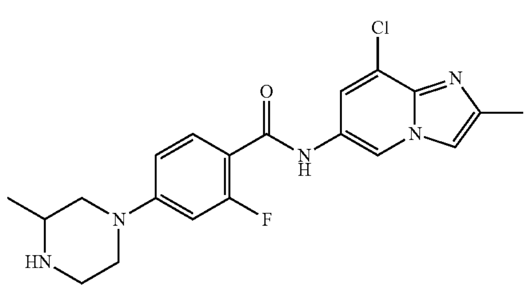 | rac-N-(8-chloro-2-methylimidazo-[1,2-a]pyridin-6-yl)-2-fluoro-4-(3-methylpiperazin-1-yl)benzamide dihydrochloride | rac-4-(4-(tert-butoxy-carbonyl)-3-methyl-piperazin-1-yl)-2-fluorobenzoic acid (Example C.3) and 8-chloro-2-methyl-imidazo[1,2-a]-pyridin-6-amine hydrochloride (Example B.5) followed by treatment with HCl | 402.5 |

-continued

| Expl. No. | Structure | Systematic Name | Starting Materials | MW found (MH+) |
|---|---|---|---|---|
| 55 | 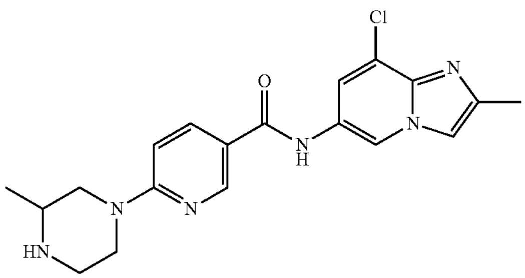 | rac-N-(8-chloro-2-methylimidazo[1,2-a]pyridin-6-yl)-6-(3-methylpiperazin-1-yl)nicotinamide dihydrochloride | rac-6-(4-(tert-butoxy-carbonyl)-3-methyl-piperazin-1-yl)nicotinic acid (CAS: 904817-70-5) and 8-chloro-2-methylimidazo[1,2-a]pyridin-6-amine hydrochloride (Example B.5) followed by treatment with HCl | 385.6 |
| 56 | 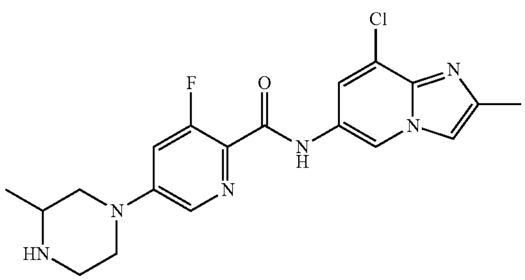 | rac-N-(8-chloro-2-methylimidazo[1,2-a]pyridin-6-yl)-3-fluoro-5-(3-methyl-piperazin-1-yl)-picolinamide dihydrochloride | rac-5-(4-(tertbutoxy-carbonyl)-3-methyl-piperazin-1-yl)-3-fluoropicolinic acid (Example C.8) and 8-chloro-2-methyl-imidazo[1,2-a]pyridin-6-amine hydrochloride (Example B.5) followed by treatment with HCl | 403.5 |
| 57 | 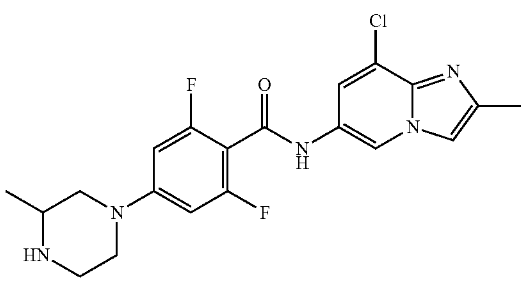 | rac-N-(8-chloro-2-methylimidazo[1,2-a]pyridin-6-yl)-2,6-difluoro-4-(3-methylpiperazin-1-yl)benzamide trihydrochloride | rac-4-(4-(tertbutoxy-carbonyl)-3-methyl-piperazin-1-yl)-2,6-difluorobenzoic acid (Example C.9) and 8-chloro-2-methyl-imidazo[1,2-a]pyridin-6-amine hydrochloride (Example B.5) followed by treatment with HCl | 420.5 |
| 58 | 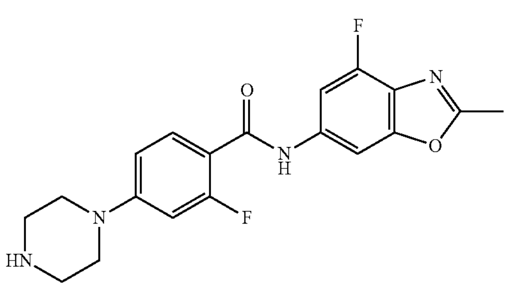 [SMILES: Cc1nc2c(F)cc(NC(=O)c3ccc(N4CCNCC4)cc3F)cc2o1] | 2-fluoro-N-(4-fluoro-2-methyl-benzo[d]oxazol-6-yl)-4-(piperazin-1-yl)benzamide | 4-(4-(tert-butoxy-carbonyl)piperazin-1-yl)-2-fluorobenzoic acid (CAS: 1121596-45-9) and 4-fluoro-2-methylbenzo[d]oxazol-6-amine hydrochloride (Example B.3) followed by treatment with TFA | 373.5 |
| 59 | 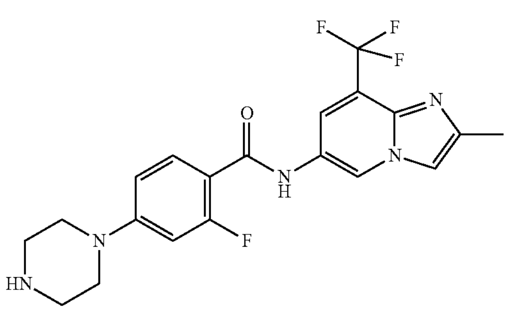 [SMILES: Cc1cn2cc(NC(=O)c3ccc(N4CCNCC4)cc3F)cc(C(F)(F)F)c2n1] | 2-fluoro-N-(2-methyl-8-(trifluoromethyl)-imidazo[1,2-a]-pyridin-6-yl)-4-(piperazin-1-yl)-benzamide | 4-(4-(tert-butoxy-carbonyl)piperazin-1-yl)-2-fluorobenzoic acid (CAS: 1121596-45-9) and 2-Methyl-8-trifluoromethyl-imidazo[1,2-a]pyridin-6-ylamine hydrochloride (Example B.2) followed by treatment with TFA | 422.5 |

| Expl. No. | Structure | Systematic Name | Starting Materials | MW found (MH+) |
|---|---|---|---|---|
| 60 | 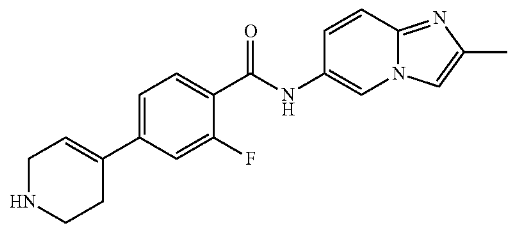 [SMILES: Cc1cn2cc(NC(=O)c3ccc(C4=CCNCC4)cc3F)ccc2n1] | 2-fluoro-N-(2-methylimidazo[1,2-a]pyridin-6-yl)-4-(1,2,3,6-tetrahydropyridin-4-yl)-benzamide hydrochloride | 4-(1-(tert-butoxycarbonyl)-1,2,3,6-tetrahydropyridin-4-yl)-2-fluorobenzoic acid (Example C.12) and 2-methylimidazo-[1,2-a]pyridin-6-amine hydrobromide (commercial) followed by treatment with HCl | 351.5 |
| 61 | 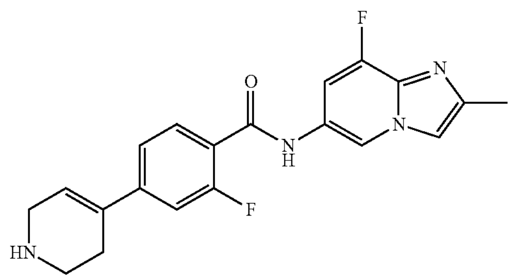 [SMILES: Cc1cn2cc(NC(=O)c3ccc(C4=CCNCC4)cc3F)cc(F)c2n1] | 2-fluoro-N-(8-fluoro-2-methyl-imidazo[1,2-a]-pyridin-6-yl)-4-(1,2,3,6-tetra-hydropyridin-4-yl)benzamide hydrochloride | 4-(1-(tert-butoxycarbonyl)-1,2,3,6-tetrahydropyridin-4-yl)-2-fluorobenzoic acid (Example C.12) and 8-Fluoro-2-methyl-imidazo[1,2-a]pyridin-6-ylamine hydrochloride (Example B.4) followed by treatment with HCl | 369.5 |
| 62 | 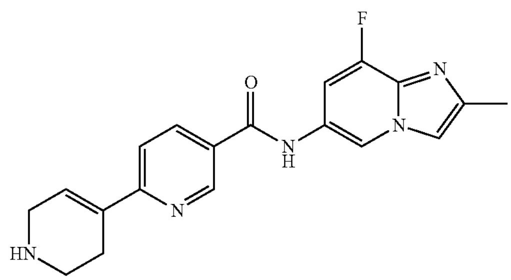 [SMILES: Cc1cn2cc(NC(=O)c3ccc(C4=CCNCC4)nc3)cc(F)c2n1] | N-(8-fluoro-2-methylimidazo[1,2-a]pyridin-6-yl)-6-(1,2,3,6-tetra-hydropyridin-4-yl)nicotinamide dihydrochloride | 6-(1-(tert-butoxycarbonyl)-1,2,3,6-tetrahydropyridin-4-yl)nicotinic acid (Example C.13) and 8-Fluoro-2-methyl-imidazo[1,2-a]pyridin-6-ylamine hydrochloride (Example B.4) followed by treatment with HCl | 352.5 |
| 63 | 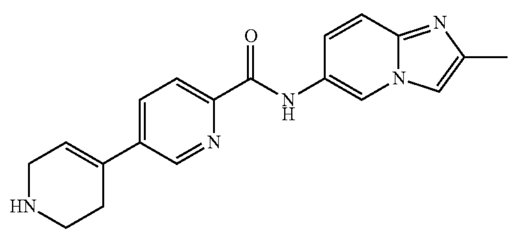 [SMILES: Cc1cn2cc(NC(=O)c3ccc(C4=CCNCC4)cn3)ccc2n1] | N-(2-methyl-imidazo[1,2-a]-pyridin-6-yl)-5-(1,2,3,6-tetra-hydropyridin-4-yl)picolinamide dihydrochloride | 5-(1-(tert-butoxycarbonyl)-1,2,3,6-tetrahydropyridin-4-yl)picolinic acid (Example C.14) and 2-methylimidazo[1,2-a]pyridin-6-amine hydrobromide (commercial followed by treatment with HCl | 334.5 |

Example 64

Preparation of N-(8-fluoro-2-methylimidazo[1,2-a]pyridin-6-yl)-2-methoxy-6-(piperazin-1-yl)nicotinamide

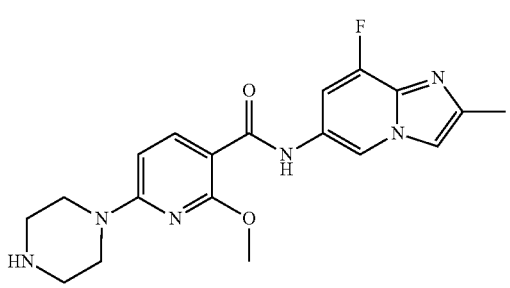 [SMILES: COc1nc(N2CCNCC2)ccc1C(=O)Nc1cc(F)c2nc(C)cn2c1]

To a solution of 6-(4-(tert-butoxycarbonyl)piperazin-1-yl)-2-methoxynicotinic acid (Example C.15) (100 mg, 296 µmol) and 8-fluoro-2-methyl-imidazo[1,2-a]pyridin-6-ylamine hydrochloride (Example B.4) (60 mg, 296 µmol) in N,N-dimethylformamide (1.00 ml) under argon at room temperature, was added O-(benzotriazol-1-yl)-N,N,N',N'-tetramethyluronium tetrafluoroborate (114 mg, 536 µmol) and triethylamine (124 µl, 0.89 mmol). The mixture was stirred at 55° C. for 16 hours and then at 90° C. for 3 hours. The reaction was poured into water and extracted with ethyl acetate. The ethyl acetate was dried over sodium sulfate, filtered and concentrated in vacuo. The crude oil was purified on silica gel (Eluent: heptane/ethyl acetate 50 to 100%) to provide 76 mg of tert-butyl 4-(5-(8-fluoro-2-methylimidazo[1,2-a]pyridin-6-ylcarbamoyl)-6-methoxypyridin-2-yl)piperazine-1-carboxylate. This compound was then dissolved in 4M HCl in dioxane (2 ml) and the mixture stirred for 0.5 h. The mixture was evaporated to dryness in vacuo, the residue dissolved in saturated sodium hydrogen carbonate and repeatedly extracted with dichloromethane. The combined extracts were dried over sodium sulfate, filtered and concentrated in vacuo dried to provide 39 mg (63%) of the title compound as an off-white solid. MS(m/e): 385.4 (M+H).

In analogy to Example 64, compounds 65 to 76 of the following table were prepared from the acid and amine derivatives followed by treatment with HCl

| Expl. No. | Structure | Systematic Name | Starting materials | MW found (MH+) |
|---|---|---|---|---|
| 65 | 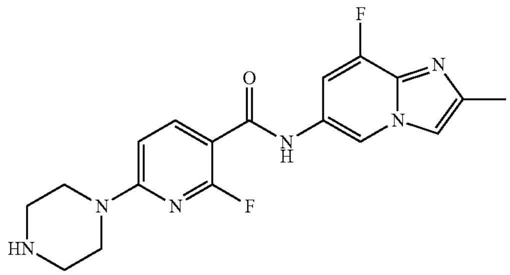 [SMILES: Cc1cn2cc(NC(=O)c3ccc(N4CCNCC4)nc3F)cc(F)c2n1] | 2-fluoro-N-(8-fluoro-2-methylimidazo[1,2-a]pyridin-6-yl)-6-(piperazin-1-yl)-nicotinamide | 6-(4-(tert-butoxycarbonyl)piperazin-1-yl)-2-fluoronicotinic acid (Example C.16) and 8-Fluoro-2-methyl-imidazo[1,2-a]pyridin-6-ylamine hydrochloride (Example B.4) followed by treatment with HCl | 373.3 |
| 66 | 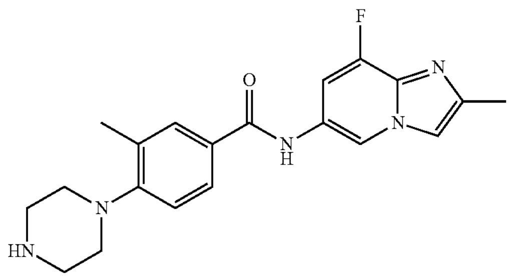 [SMILES: Cc1cn2cc(NC(=O)c3ccc(N4CCNCC4)c(C)c3)cc(F)c2n1] | N-(8-fluoro-2-methylimidazo[1,2-a]pyridin-6-yl)-3-methyl-4-(piperazin-1-yl)benzamide | 4-(4-(tert-butoxycarbonyl)piperazin-1-yl)-3-methylbenzoic acid (CAS: 196203-51-7) and 8-Fluoro-2-methylimidazo[1,2-a]-pyridin-6-ylamine hydrochloride (Example B.4) followed by treatment with HCl | 368.6 |
| 67 | 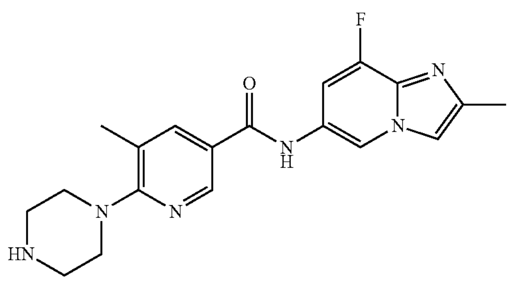 | N-(8-fluoro-2-methylimidazo[1,2-a]pyridin-6-yl)-5-methyl-6-(piperazin-1-yl)nicotinamide | 6-(4-(tert-butoxycarbonyl)piperazin-1-yl)-5-methylnicotinic acid (CAS: 1211527-14-8) and 8-Fluoro-2-methylimidazo[1,2-a]pyridin-6-ylamine hydrochloride (Example B.4) followed by treatment with HCl | LG |
| 68 | 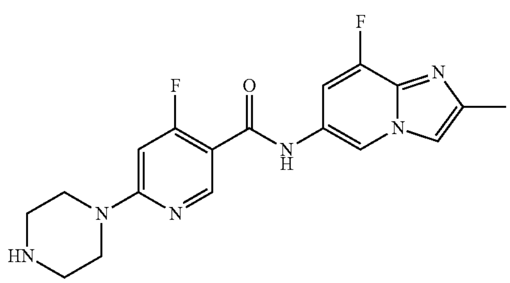 [SMILES: Cc1cn2cc(NC(=O)c3cnc(N4CCNCC4)cc3F)cc(F)c2n1] | 4-fluoro-N-(8-fluoro-2-methylimidazo[1,2-a]pyridin-6-yl)-6-(piperazin-1-yl)nicotinamide | 6-(4-(tert-butoxycarbonyl)piperazin-1-yl)-4-fluoronicotinic acid (Example C.17) and 8-Fluoro-2-methyl-imidazo[1,2-a]pyridin-6-ylamine hydrochloride (Example B.4) followed by treatment with HCl | 373.7 |
| 69 | 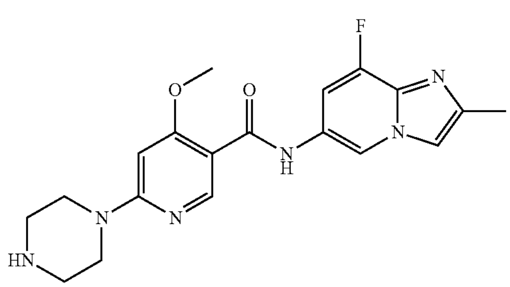 [SMILES: COc1cc(N2CCNCC2)ncc1C(=O)Nc1cc(F)c2nc(C)cn2c1] | N-(8-fluoro-2-methylimidazo[1,2-a]pyridin-6-yl)-4-methoxy-6-(piperazin-1-yl)nicotinamide | 6-(4-(tert-butoxycarbonyl)piperazin-1-yl)-4-methoxynicotinic acid (Example C.18) and 8-Fluoro-2-methyl-imidazo[1,2-a]pyridin-6-ylamine hydrochloride (Example B.4) followed by treatment with HCl | 385.6 |

| Expl. No. | Structure | Systematic Name | Starting materials | MW found (MH+) |
|---|---|---|---|---|
| 70 | 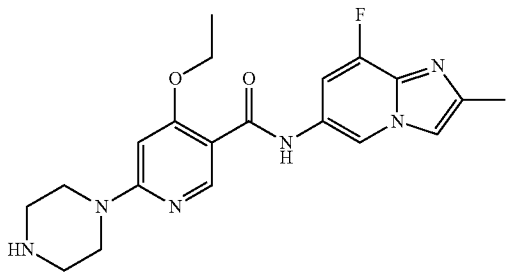 [SMILES: CCOc1cc(N2CCNCC2)ncc1C(=O)Nc1cc(F)c2nc(C)cn2c1] | 4-ethoxy-N-(8-fluoro-2-methylimidazo[1,2-a]pyridin-6-yl)-6-(piperazin-1-yl)nicotinamide | 6-(4-(tert-butoxy-carbonyl)piperazin-1-yl)-4-ethoxynicotinic acid (Example C.19) and 8-Fluoro-2-methyl-imidazo[1,2-a]pyridin-6-ylamine hydrochloride (Example B.4) followed by treatment with HCl | 399.6 |
| 71 | 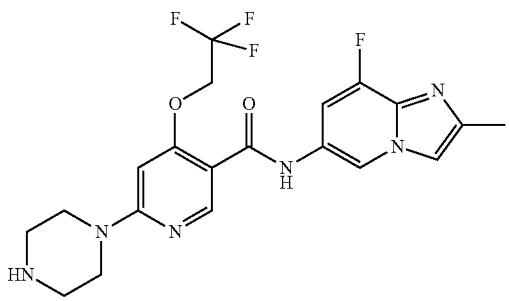 [SMILES: Cc1cn2cc(NC(=O)c3cnc(N4CCNCC4)cc3OCC(F)(F)F)cc(F)c2n1] | N-(8-fluoro-2-methylimidazo[1,2-a]pyridin-6-yl)-6-(piperazin-1-yl)-4-(2,2,2-trifluoro-ethoxy)nicotinamide | 6-(4-(tert-butoxy-carbonyl)piperazin-1-yl)-4-(2,2,2-trifluoro-ethoxy)nicotinic acid (Example C.20) and 8-Fluoro-2-methyl-imidazo[1,2-a]pyridin-6-ylamine hydrochloride (Example B.4) followed by treatment with HCl | 453.6 |
| 72 | 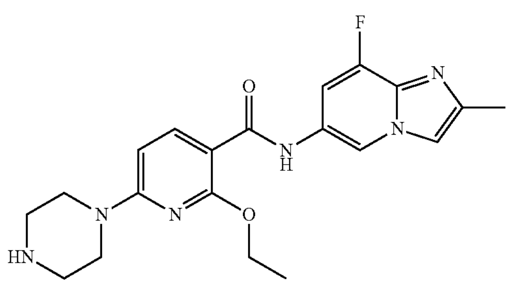 [SMILES: CCOc1nc(N2CCNCC2)ccc1C(=O)Nc1cc(F)c2nc(C)cn2c1] | 2-ethoxy-N-(8-fluoro-2-methylimidazo[1,2-a]pyridin-6-yl)-6-(piperazin-1-yl)-nicotinamide | 6-(4-(tert-butoxy-carbonyl)piperazin-1-yl)-2-ethoxynicotinic acid (Example C.21) and 8-Fluoro-2-methyl-imidazo[1,2-a]pyridin-6-ylamine hydrochloride (Example B.4) followed by treatment with HCl | 399.6 |
| 73 | 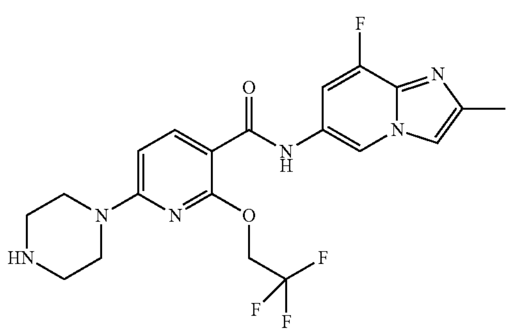 [SMILES: Cc1cn2cc(NC(=O)c3ccc(N4CCNCC4)nc3OCC(F)(F)F)cc(F)c2n1] | N-(8-fluoro-2-methylimidazo[1,2-a]pyridin-6-yl)-6-(piperazin-1-yl)-2-(2,2,2-trifluoro-ethoxy)nicotinamide | 6-(4-(tert-butoxy-carbonyl)piperazin-1-yl)-2-(2,2,2-trifluoro-ethoxy)nicotinic acid (Example C.22) and 8-Fluoro-2-methyl-imidazo[1,2-a]pyridin-6-ylamine hydrochloride (Example B.4) followed by treatment with HCl | 453.6 |
| 74 | 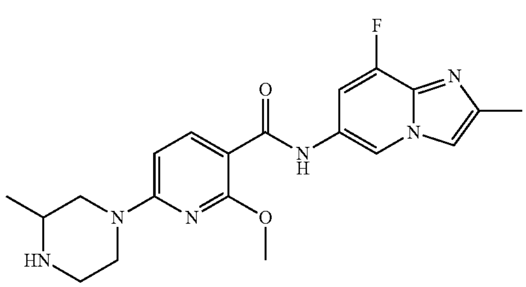 | rac-N-(8-fluoro-2-methylimidazo[1,2-a]pyridin-6-yl)-2-methoxy-6-(3-methylpiperazin-1-yl)nicotinamide | rac-6-(4-(tert-butoxy-carbonyl)-3-methyl-piperazin-1-yl)-2-methoxynicotinic acid (Example C.23) and 8-Fluoro-2-methyl-imidazo[1,2-a]pyridin-6-ylamine hydrochloride (Example B.4) followed by treatment with HCl | 399.6 |

| Expl. No. | Structure | Systematic Name | Starting materials | MW found (MH+) |
|---|---|---|---|---|
| 75 | 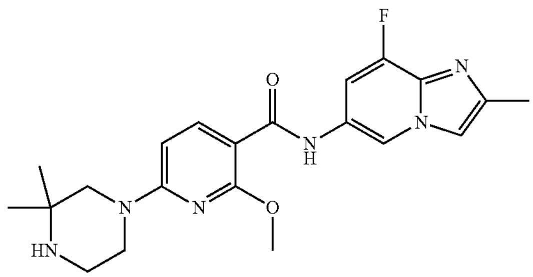 | 6-(3,3-dimethyl-piperazin-1-yl)-N-(8-fluoro-2-methyl-imidazo[1,2-a]-pyridin-6-yl)-2-methoxynicotinamide | 6-(4-(tert-butoxy-carbonyl)-3,3-dimethylpiperazin-1-yl)-2-methoxynicotinic acid (Example C.24) and 8-Fluoro-2-methyl-imidazo[1,2-a]pyridin-6-ylamine hydrochloride (Example B.4) followed by treatment with HCl | 411.6 |
| 76 | 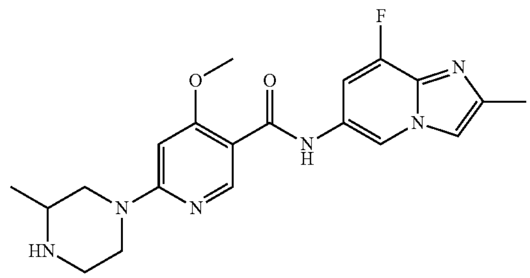 | rac-N-(8-fluoro-2-methylimidazo[1,2-a]pyridin-6-yl)-4-methoxy-6-(3-methylpiperazin-1-yl)nicotinamide | 6-(4-(tert-butoxy-carbonyl)-3-methyl-piperazin-1-yl)-4-methoxynicotinic acid (Example C.25) and 8-Fluoro-2-methylimidazo-[1,2-a]pyridin-6-ylamine hydrochloride (Example B.4) followed by treatment with HCl | 399.5 |

Example 77

Preparation of N-(2-methylimidazo[1,2-a]pyridin-6-yl)-6-(1,2,3,6-tetrahydropyridin-4-yl)nicotinamide hydrochloride

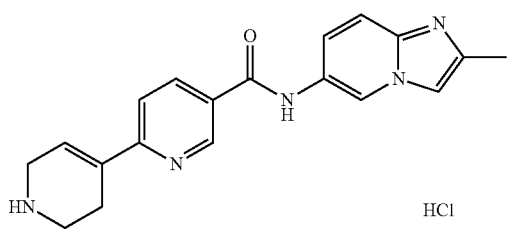 [SMILES: Cc1cn2cc(NC(=O)c3ccc(C4=CCNCC4)nc3)ccc2n1 ; Cl]

a) step 1: tert-butyl 4-(5-(2-methylimidazo[1,2-a]pyridin-6-ylcarbamoyl)pyridin-2-yl)-5,6-dihydro-pyridine-1(2H)-carboxylate To a solution of 6-chloro-N-(2-methylimidazo[1,2-a]pyridin-6-yl)nicotinamide (Example A5) (100 mg, 349 µmol) in a mixture of 1,2-dimethoxyethane (1.25 ml), ethanol (625 µl) and water (1.25 ml) under nitrogen at room temperature, were added tert-butyl 4-(4,4,5,5-tetramethyl-1,3,2-dioxaborolan-2-yl)-5,6-dihydropyridine-1(2H)-carboxylate (129 mg, 419 µmol), K2CO3 (122 mg, 875 µmol) and PdCl2(Ph3P)2 (25.2 mg, 35.9 µmol, Eq: 0.103). The reaction mixture was heated in an oil bath at 100° C. for 40 minutes. After cooling to room temperature, the solvent was removed under reduced pressure. The residue was dissolved in dichloromethane and washed with brine. The aqueous phase was extracted three times with methylene chloride and the combined organic phase was dried with Na2SO4, filtered and concentrated to dryness to obtain 285 mg of a dark brown solid. This solid was suspended in ethyl acetate, filtered and dried to provide 86 mg (56.9%) of the title compound as a light brown solid. MS (m/e): 434.5 (M+H+).

b) step 2: N-(2-methylimidazo[1,2-a]pyridin-6-yl)-6-(1,2,3,6-tetrahydropyridin-4-yl)nicotinamide hydrochloride To a solution of tert-butyl 4-(5-(2-methylimidazo[1,2-a]pyridin-6-ylcarbamoyl)pyridin-2-yl)-5,6-dihydropyridine-1(2H)-carboxylate (20 mg, 46.1 µmol) in methanol (200 µl) under nitrogen at room temperature, was added dropwise hydrogen chloride (4M in dioxane) (115 µl, 461 µmol). The reaction mixture was stirred at room temperature overnight. The resulting precipitation was filtered, rinsed with diethyl ether and dried to provide 12.6 mg (73.8%) of the expected compound as a grey solid. MS(m/e): 334.5 (M+H+).

Example 78

Preparation of N-(2-methylimidazo[1,2-a]pyridin-6-yl)-6-(1-methylpiperidin-4-yl)nicotinamide

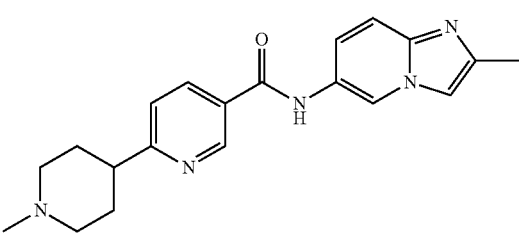

a) step 1: tert-butyl 4-(5-(2-methylimidazo[1,2-a]pyridin-6-ylcarbamoyl)pyridin-2-yl)piperidine-1-carboxylate To a solution of tert-butyl 4-(5-(2-methylimidazo[1,2-a]pyridin-6-ylcarbamoyl)pyridin-2-yl)-5,6-dihydropyridine-1(2H)-carboxylate (Example 77, step 1) (123 mg, 284 µmol) in methanol (7 ml) and tetrahydrofurane (3.5 ml) under nitrogen at room temperature was added palladium on activated charcoal (54.3 mg, 51.0 µmol). The reaction mixture was stirred under a hydrogen atmosphere overnight. The reaction mixture was purged with argon, filtered and the solvent was evaporated. The crude oil was purified with flash column chromatography on silica eluting with a gradient formed from n-heptane and ethyl acetate (0 to 100%) and ethyl acetate and methanol (0 to 15%) to provide 86 mg (69.6%) of the title compound as an off-white solid. MS (m/e): 436.6 (M+H)

b) step 2: N-(2-methylimidazo[1,2-a]pyridin-6-yl)-6-(piperidin-4-yl)nicotinamide To a suspension of tert-butyl 4-(5-(2-methylimidazo[1,2-a]pyridin-6-ylcarbamoyl)pyridin-2-yl)piperidine-1-carboxylate (17 mg, 39.0 µmol) in methanol (170 µl) was added HCl 4M in dioxane (97.6 µl, 390 µmol). The light yellow solution was stirred at room temperature overnight. The solvent was evaporated to provide 14 mg (87.8%) of the title compound as a grey solid. MS(m/e): 336.3 (M+H)

c) step 3: N-(2-methylimidazo[1,2-a]pyridin-6-yl)-6-(1-methylpiperidin-4-yl)nicotinamide To a suspension of N-(2-methylimidazo[1,2-a]pyridin-6-yl)-6-(piperidin-4-yl)nicotinamide (25 mg, 74.5 µmol) in 1,2-dichloroethane (250 µl) under nitrogen at 5-10° C., was added sodium triacetoxyborohydride (26.3 mg, 112 µmol), followed dropwise (over 5 minutes) by formaldehyde solution (37% in water) (18.1 mg, 16.6 µl, 224 µmol). The temperature was kept to 5-10° C. and the reaction mixture was stirred for 40 minutes. The reaction was quenched with a 2N sodium carbonate aqueous solution. The resulting precipitation was stirred at room temperature for 30 minutes, filtered, rinsed and dried to provide 17 mg (65.3%) of the title compound as an off-white solid. MS(m/e): 350.5 (M+H+)

Example 79

Preparation of N-(8-fluoro-2-methylimidazo[1,2-a]pyridin-6-yl)-6-(piperidin-4-yl)nicotinamide dihydrochloride

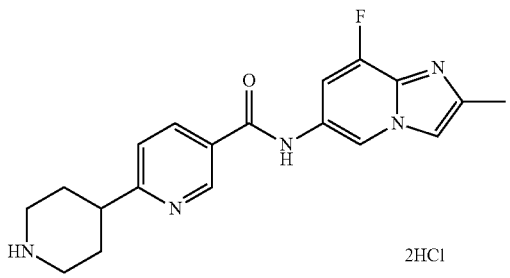 [SMILES: Cc1cn2cc(NC(=O)c3ccc(C4CCNCC4)nc3)cc(F)c2n1 ; "2HCl"]

2HCl

To a solution of N-(8-fluoro-2-methylimidazo[1,2-a]pyridin-6-yl)-6-(1,2,3,6-tetrahydropyridin-4-yl)nicotinamide dihydrochloride (Example 62) (30 mg, 70.7 µmol) in methanol (1.7 ml) and tetrahydrofurane (850 µl) under nitrogen at room temperature, was added palladium on activated charcoal (20 mg, 18.8 µmol, Eq: 0.266). The reaction mixture was stirred under a hydrogen atmosphere for 4 hours. The reaction mixture was purged with argon, filtered and the solvent was evaporated to provide 28 mg (92.9%) of the title compound as a yellow solid. MS (m/e): 354.5 (M+H+).

Example 80

Preparation of N-(8-fluoro-2-methylimidazo[1,2-a]pyridin-6-yl)-6-(1-methylpiperidin-4-yl)nicotinamide

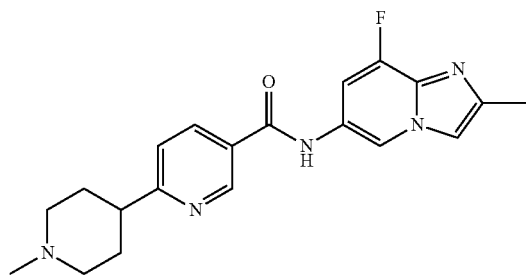

In analogy to the procedure described for the synthesis of example 78 (steps: 3), the title compound was prepared from N-(8-fluoro-2-methylimidazo[1,2-a]pyridin-6-yl)-6-(piperidin-4-yl)nicotinamide dihydrochloride (Example 79). MS (m/e): 368.5 (M+H+).

Example 81

Preparation of 2-fluoro-N-(8-fluoro-2-methylimidazo[1,2-a]pyridin-6-yl)-4-(piperidin-4-yl)benzamide hydrochloride

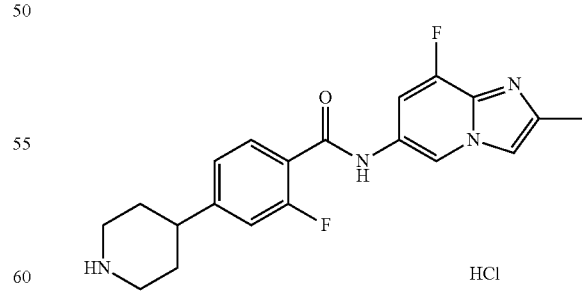

HCl

In analogy to the procedure described for the synthesis of example 79, the title compound was prepared from 2-fluoro-N-(8-fluoro-2-methylimidazo[1,2-a]pyridin-6-yl)-4-(1,2,3,6-tetrahydropyridin-4-yl)benzamide (Example 61). MS (m/e): 371.5 (M+H+).

Example 82

Preparation of rac-6-(3,4-dimethylpiperazin-1-yl)-N-(2-methylimidazo[1,2-a]pyridin-6-yl)nicotinamide

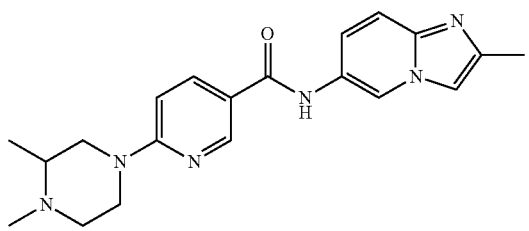

In analogy to the procedure described for the synthesis of example 78 (step 3), the title compound was prepared from rac-N-(2-methylimidazo[1,2-a]pyridin-6-yl)-6-(3-methyl-piperazin-1-yl)nicotinamide (Example 12). MS (m/e): 365.6 (M+H+).

Biological Assays

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. These examples illustrate the testing of certain compounds described herein in vitro and/or in vivo and demonstrate the usefulness of the compounds for treating of SMA by enhancing the inclusion of exon 7 of SMN2 into mRNA transcribed from the SMN2 gene. Compounds of formula (I) enhance inclusion of exon 7 of SMN2 into mRNA transcribed from the SMN2 gene and increase levels of SMN protein produced from the SMN2 gene, and thus can be used to treat SMA in a human subject in need thereof. These examples further illustrate the testing of certain compounds described herein in vitro and/or in vivo and demonstrate the usefulness of the compounds for enhancing the inclusion of exon 7 of SMN1 into mRNA transcribed from the SMN1 gene. Accordingly, compounds of formula (I) also enhance the inclusion of exon 7 of SMN1 into mRNA transcribed from the SMN1 gene and increase levels of SMN protein produced from the SMN1 gene.

Example D.1

SMN2 Minigene mRNA Splicing RT-qPCR Assay in Cultured Cells

The reverse transcription-quantitative PCR-based (RT-qPCR) assay is used to quantify the level of the full length SMN2 minigene (referred to herein by the term "FL SMN2mini") mRNA containing SMN2 exon 7 in a HEK293H cell line stably transfected with said minigene and treated with a test compound.

| Material | Source |
|---|---|
| HEK293H cells | Life Technologies, Inc. (formerly Invitrogen) Catalog No. 11631-017 |
| Cells-To-Ct lysis buffer | Life Technologies, Inc. (formerly Applied Biosystems) part No. 4399002 |
| DMEM | Life Technologies, Inc. (formerly Invitrogen) Catalog No. 11960-044 |
| 96-well flat-bottom plates | Becton Dickinson Catalog No. 353072 |
| RT-PCR Enzyme Mix | Life Technologies, Inc. (formerly Applied Biosystems) part No. 4388520 |
| RT-PCR buffer | Life Technologies, Inc. (formerly Applied Biosystems) part No. 4388519 |
| AgPath-ID One-Step RT-PCR kit | Life Technologies, Inc. (formerly Applied Biosystems) part No. 4387391 |
| Thermocycler | Life Technologies, Inc. (formerly Applied Biosystems) 7900HT |

The SMN2-A minigene construct was prepared as described in International Patent Application WO2009/151546A1 page 145 paragraph [00400] to page 147 paragraph [00412](incl. FIG. 1 and FIG. 3 therein).

HEK293H cells stably transfected with the SMN2-A minigene construct (10,000 cells/well) are seeded in 200 µL of cell culture medium (DMEM plus 10% FBS, with 200 µg/mL hygromycin) in 96-well flat-bottom plates and the plate is immediately swirled to ensure proper dispersal of cells and the formation of an even monolayer of cells. Cells are allowed to attach for 6 hours. Test compounds are serially diluted 3.16-fold in 100% DMSO to generate a 7-point concentration curve. A solution of test compound (1 µL, 200× in DMSO) is added to each cell-containing well and the plate is incubated for 24 hours in a cell culture incubator (37° C., 5% $CO_2$, 100% relative humidity). 2 replicates are prepared for each test compound concentration. The cells are then lysed in the Cells-To-Ct lysis buffer and the lysate is stored at −80° C.

Full length SMN2-A minigene and GAPDH mRNA are quantified using the primers and probes referenced in Table 1. Primer SMN Forward A (SEQ ID NO.1) hybridizes to a nucleotide sequence in exon 7 (nucleotide 22 to nucleotide 40), primer SMN Reverse A (SEQ ID NO.2) hybridizes to a nucleotide sequence in the coding sequence of Firefly luciferase, SMN Probe A (SEQ ID NO.3) hybridizes to a nucleotide sequence in exon 7 (nucleotide 50 to nucleotide 54) and exon 8 (nucleotide 1 to nucleotide 21). The combination of these three oligonucleotides detects only SMN1 or SMN2 minigenes (RT-qPCR) and will not detect endogenous SMN1 or SMN2 genes.

TABLE 1

| Primers/Probes | Sequences | Source |
|---|---|---|
| SMN Forward Primer A | SEQ ID NO. 1: GAAGGAAGGTGCTCACATT | PTC[1] |
| SMN Reverse Primer A | SEQ ID NO. 2: TCTTTATGTTTTGGCGTCTTC | PTC[1] |

TABLE 1-continued

| Primers/Probes | Sequences | Source |
|---|---|---|
| SMN Forward Probe A | SEQ ID NO. 3: 6FAM-AAGGAGAAATGCTGGCATAGAGCAGC-TAMRA | PTC[1] |
| hGAPDH Forward Probe | SEQ ID NO.4: VIC-CGCCTGGTCACCAGGGCTGCT-TAMRA | LTI[2] |
| hGAPDH Forward Primer | SEQ ID NO.5: CAACGGATTTGGTCGTATTGG | LTI[2] |
| hGAPDH Reverse Primer | SEQ ID NO.6: TGATGGCAACAATATCCACTTTACC | LTI[2] |

[1] Primers and probes designed by PTC Therapeutics, Inc.;
[2] Commercially available from Life Technologies, Inc. (formerly Invitrogen).

The SMN forward and reverse primers are used at final concentrations of 0.4 μM. The SMN probe is used at a final concentration of 0.15 μM. The GAPDH primers are used at final concentrations of 0.2 μM and the probe at 0.15 μM.

The SMN2-minigene GAPDH mix (15 μL total volume) is prepared by combining 7.5 μL of 2×RT-PCR buffer, 0.4 μL of 25×RT-PCR enzyme mix, 0.75 μL of 20×GAPDH primer-probe mix, 4.0075 μL of water, 2 μL of 10-fold diluted cell lysate, 0.06 μL of 100 μM SMN forward primer, 0.06 μL of 100 μM SMN reverse primer, and 0.225 μL of 100 μM SMN probe.

PCR is carried out at the following temperatures for the indicated time: Step 1: 48° C. (15 min); Step 2: 95° C. (10 min); Step 3: 95° C. (15 sec); Step 4: 60° C. (1 min); then repeat Steps 3 and 4 for a total of 40 cycles.

Each reaction mixture contains both SMN2-A minigene and GAPDH primers/probe sets (multiplex design), allowing simultaneous measurement of the levels of two transcripts.

The increase in the abundance of the FL SMN2mini mRNA relative to that in cells treated with vehicle control is determined from real-time PCR data using a modified ΔΔCt method (as described in Livak and Schmittgen, Methods, 2001, 25:402-8). The amplification efficiency E is calculated from the slope of the amplification curve for FL SMN2mini and GAPDH individually. The abundance of FL SMN2mini and GAPDH mRNA are then calculated as $(1+E)^{-Ct}$, where Ct is the threshold value for each amplicon. The abundance of FL SMN2mini mRNA is normalized to GAPDH mRNA abundance. The normalized FL SMN2mini mRNA abundance from test compound-treated samples is then divided by normalized FL SMN2mini mRNA abundance from vehicle-treated cells to determine the level of FL SMN2mini mRNA relative to vehicle control.

Table 2 provides $EC_{1.5x}$ concentrations for production of full length SMN2 minigene mRNA that was obtained from the 7-point concentration data generated according to the above procedure for particular compounds of the present invention.

Particular compounds of the present invention exhibit an $EC_{1.5x}$ concentration for production of full length SMN2 minigene mRNA≤1 μM.

More particular compounds of the present invention exhibit an $EC_{1.5x}$ concentration for production of full length SMN2 minigene mRNA≤0.1 μM.

Most particular compounds of the present invention exhibit an EC1.5× concentration for production of full length SMN2 minigene mRNA≤0.02 μM.

TABLE 2

$EC_{1.5x}$ concentrations for production of full length SMN2 minigene mRNA.

| Ex. | $EC_{1.5x}$ minigene (μM) |
|---|---|
| 1 | 0.0316 |
| 2 | 0.1399 |
| 3 | 0.5522 |
| 4 | 0.2323 |
| 5 | 0.0612 |
| 6 | 0.2332 |
| 7 | 0.1423 |
| 8 | 0.201 |
| 9 | 0.794 |
| 10 | 0.6652 |
| 11 | 0.2971 |
| 12 | 0.3122 |
| 13 | 1.0335 |
| 14 | 0.2314 |
| 15 | 0.2539 |
| 16 | 1.0364 |
| 17 | 0.2334 |
| 18 | 0.0523 |
| 19 | 0.2673 |
| 20 | 0.4894 |
| 21 | 0.3856 |
| 22 | 0.2626 |
| 23 | 0.201 |
| 24 | 0.6489 |
| 25 | 0.3823 |
| 26 | 0.0445 |
| 27 | 0.0989 |
| 28 | 0.2524 |
| 29 | 0.2667 |
| 30 | 0.4096 |
| 31 | 0.1195 |
| 32 | 0.0938 |
| 33 | |
| 34 | 0.328 |
| 35 | 0.2022 |
| 36 | 0.0278 |
| 37 | 0.028 |
| 38 | 0.4717 |
| 39 | 0.0168 |
| 40 | 0.0108 |
| 41 | |
| 42 | 0.0544 |
| 43 | 0.057 |
| 44 | 0.0648 |
| 45 | 0.0615 |
| 46 | 0.0887 |
| 47 | 0.3964 |
| 48 | 0.0164 |
| 49 | 0.0107 |
| 50 | 0.0068 |
| 51 | 0.0084 |
| 52 | 0.04 |

TABLE 2-continued

EC$_{1.5x}$ concentrations for production of full length SMN2 minigene mRNA.

| Ex. | EC$_{1.5x}$ minigene (μM) |
|---|---|
| 53 | 0.2104 |
| 54 | 0.0128 |
| 55 | 0.1411 |
| 56 | 0.017 |
| 57 | 0.0262 |
| 58 | 0.0398 |
| 59 | 0.1089 |
| 60 | 0.0428 |
| 61 | 0.01 |
| 62 | 0.0136 |
| 63 | 0.1602 |
| 64 | 0.0291 |
| 65 | 0.0762 |
| 66 | 0.5177 |
| 67 | 0.3175 |
| 68 | 0.0285 |
| 69 | 0.0308 |
| 70 | |
| 71 | 0.077 |
| 72 | 0.015 |
| 73 | 0.062 |
| 74 | 0.0161 |
| 75 | 0.0654 |
| 76 | 0.0187 |
| 77 | 0.0641 |
| 78 | 0.6222 |
| 79 | 0.0559 |
| 80 | 0.1148 |
| 81 | 0.0374 |
| 82 | 0.3714 |

Example D.2

SMN Protein Assay in Cultured Cells

The SMN HTRF (homogeneous time resolved fluorescence) assay is used to quantify the level of SMN protein in SMA patient fibroblast cells treated with test compounds.

| Material | Source |
|---|---|
| SMA Type 1 human cells | GM03813 (Coriell Institute) |
| Protease inhibitor cocktail | Roche Applied Science Catalog No. 11836145001 |
| Anti-SMN d2 | Blue cap Cisbio Catalog No. 63IDC002-SMN |
| Anti-SMN kryptate | Red cap Cisbio Catalog No. 63IDC002-SMN |
| SMN reconstitution buffer | Cisbio Catalog No. 63IDC002-SMN-Buffer |
| DMEM | Life Technologies (formerly Invitrogen) Catalog No. 11960-044 |
| RIPA Lysis Buffer | 20 mM Tris-HCl pH 7.5, 150 mM NaCl, 1 mM EDTA, 1% Thermo Scientific NP-40 Surfact-Amps Detergent Solution (Fisher Scientific, Pittsburgh/PA), 1% Sodium deoxycholate |
| Diluent Buffer | 20 mM Tris-HCl pH 7.5, 150 mM NaCl |
| Envision Plate Reader | Perkin Elmer Model # 2103 |

Cells are thawed and cultured in DMEM-10% FBS for 72 hours. Cells are trypsinized, counted and re-suspended to a concentration of 25,000 cells/mL in DMEM-10% FBS. The cell suspensions are plated at 5,000 cells per well in a 96 well microtiter plate and incubated for 3 to 5 hours. Test compounds are serially diluted 3.16-fold in 100% DMSO to generate a 7-point concentration curve. 1 μL of test compound solution is transferred to cell-containing wells and cells are incubated for 48 hours in a cell culture incubator (37° C., 5% CO$_2$, 100% relative humidity). Triplicate samples are set up for each test compound concentration. After 48 hours, the supernatant is removed from the wells and 25 μL of the RIPA lysis buffer, containing protease inhibitors, is added to the wells and incubated with shaking at room temperature for 1 hour. 25 μL of the diluent is added and then 35 μL of the resulting lysate is transferred to a 384-well plate, where each well contains 5 μL of the antibody solution (1:100 dilution of anti-SMN d2 and anti-SMN kryptate in SMN reconstitution buffer). The plate is centrifuged for 1 minute to bring the solution to the bottom of the wells, then incubated overnight at room temperature. Fluorescence for each well of the plate at 665 nm and 620 nm is measured on an EnVision multilabel plate reader (Perkin-Elmer).

The normalized fluorescence signal is calculated for each sample, Blank and vehicle control well by dividing the signal at 665 nm by the signal at 620 nm. Normalizing the signal accounts for possible fluorescence quenching due to the matrix effect of the lysate. The ΔF value (a measurement of SMN protein abundance as a percent value) for each sample well is calculated by subtracting the normalized average fluorescence for the Blank control wells from the normalized fluorescence for each sample well, then dividing this difference by the normalized average fluorescence for the Blank control wells and multiplying the resulting value by 100. The ΔF value for each sample well represents the SMN protein abundance from test compound-treated samples. The ΔF value for each sample well is divided by the ΔF value for the vehicle control wells to calculate the fold increase in SMN protein abundance relative to the vehicle control. Table 3 provides EC$_{1.5x}$ concentrations for SMN protein expression that was obtained from the 7-point concentration data generated according to the above procedure for particular compounds of the present invention.

Particular compounds of the present invention exhibit an EC$_{1.5x}$ concentration for SMN protein expression ≤2 μM.

More particular compounds of the present invention exhibit an EC$_{1.5x}$ concentration for SMN protein expression ≤0.3 μM.

Most particular compounds of the present invention exhibit an EC$_{1.5x}$ concentration for SMN protein expression ≤0.1 μM.

Table 4 provides the maximum fold increase of SMN protein that was obtained from the 7-point concentration data generated according to the above procedure for particular compounds of the present invention Particular compounds of the present invention exhibit a maximum fold increase >1.4.

More particular compounds of the present invention exhibit a maximum fold increase >1.7.

Most particular compounds of the present invention exhibit a maximum fold increase >1.8.

TABLE 3

EC$_{1.5x}$ concentrations for SMN protein expression.

| Ex. | EC$_{1.5x}$ SMN protein (μM) |
|---|---|
| 1 | 0.7747 |
| 2 | 0.2984 |
| 3 | 1.47 |

TABLE 3-continued

EC$_{1.5x}$ concentrations for SMN protein expression.

| Ex. | EC$_{1.5x}$ SMN protein (μM) |
|---|---|
| 4 | 0.5614 |
| 5 | 0.107 |
| 6 | 0.5305 |
| 7 | 0.2834 |
| 8 | 0.5175 |
| 9 | 1.527 |
| 10 | 0.329 |
| 11 | 0.321 |
| 12 | 0.7037 |
| 13 | 1.7564 |
| 14 | 0.7944 |
| 15 | 0.281 |
| 16 | 1.1992 |
| 17 | 0.5022 |
| 18 | 0.1346 |
| 19 | 1.3818 |
| 20 | 0.8065 |
| 21 | 0.6542 |
| 22 | 0.4468 |
| 23 | 0.5092 |
| 24 | 1.2616 |
| 25 | 0.5694 |
| 26 | 0.2853 |
| 27 | 0.3964 |
| 28 | 0.2868 |
| 29 | 0.4618 |
| 30 | 0.7612 |
| 31 | 0.2746 |
| 32 | 0.2028 |
| 33 | 0.5703 |
| 34 | 0.7793 |
| 35 | 1.2664 |
| 36 | 0.1094 |
| 37 | 0.1196 |
| 38 | 0.6124 |
| 39 | 0.0147 |
| 40 | 0.0276 |
| 41 | 0.0508 |
| 42 | 0.1488 |
| 43 | 0.104 |
| 44 | 0.13 |
| 45 | 0.5147 |
| 46 | 0.3584 |
| 47 | 0.611 |
| 48 | 0.0621 |
| 49 | 0.1733 |
| 50 | 0.0344 |
| 51 | 0.0561 |
| 52 | 0.1518 |
| 53 | 0.7455 |
| 54 | 0.056 |
| 55 | 0.7112 |
| 56 | 0.07 |
| 57 | 1.7363 |
| 58 | 0.1159 |
| 59 | 0.2749 |
| 60 | 0.107 |
| 61 | |
| 62 | |
| 63 | 1.0431 |
| 64 | 0.1192 |
| 65 | 0.1135 |
| 66 | 0.6108 |
| 67 | 0.866 |
| 68 | 0.057 |
| 69 | 0.1645 |
| 70 | 0.0187 |
| 71 | 0.4077 |
| 72 | 0.1324 |
| 73 | 0.7589 |
| 74 | 0.1524 |
| 75 | 0.3061 |
| 76 | 0.1629 |
| 77 | 0.2279 |
| 78 | 1.013 |
| 79 | 0.2559 |
| 80 | 0.52 |
| 81 | 0.2723 |
| 82 | 0.7698 |

TABLE 4

Maximum fold increase of SMN protein.

| Ex. | max. fold increase |
|---|---|
| 1 | 1.6736 |
| 2 | 1.8878 |
| 3 | 1.7558 |
| 4 | 1.769 |
| 5 | 1.7757 |
| 6 | 1.8047 |
| 7 | 1.7936 |
| 8 | 1.7677 |
| 9 | 1.6085 |
| 10 | 1.735 |
| 11 | 1.7143 |
| 12 | 1.6512 |
| 13 | 1.624 |
| 14 | 1.5912 |
| 15 | 1.6859 |
| 16 | 1.6598 |
| 17 | 1.6966 |
| 18 | 1.7677 |
| 19 | 1.664 |
| 20 | 1.7789 |
| 21 | 1.7755 |
| 22 | 1.7566 |
| 23 | 1.6942 |
| 24 | 1.756 |
| 25 | 1.6652 |
| 26 | 1.8316 |
| 27 | 1.6617 |
| 28 | 1.7291 |
| 29 | 1.632 |
| 30 | 1.6734 |
| 31 | 1.7849 |
| 32 | 1.7579 |
| 33 | 1.7541 |
| 34 | 1.6527 |
| 35 | 1.6275 |
| 36 | 1.7018 |
| 37 | 1.7758 |
| 38 | 1.8706 |
| 39 | 1.8791 |
| 40 | 1.7607 |
| 41 | 1.7973 |
| 42 | 1.6988 |
| 43 | 1.7873 |
| 44 | 1.8243 |
| 45 | 1.6445 |
| 46 | 1.5572 |
| 47 | 1.7065 |
| 48 | 1.738 |
| 49 | 1.658 |
| 50 | 1.6607 |
| 51 | 1.7266 |
| 52 | 1.8152 |
| 53 | 1.6563 |
| 54 | 1.8217 |
| 55 | 1.8752 |

TABLE 4-continued

Maximum fold increase of SMN protein.

| Ex. | max. fold increase |
|---|---|
| 56 | 1.7299 |
| 57 | 1.578 |
| 58 | 1.7744 |
| 59 | 1.7116 |
| 60 | 1.7375 |
| 61 | 1.7077 |
| 62 | 1.5583 |
| 63 | 1.6807 |
| 64 | 1.7581 |
| 65 | 1.7675 |
| 66 | 1.5438 |
| 67 | 1.6552 |
| 68 | 1.6943 |
| 69 | 1.7612 |

TABLE 4-continued

Maximum fold increase of SMN protein.

| Ex. | max. fold increase |
|---|---|
| 70 | 1.933 |
| 71 | 1.4815 |
| 72 | 1.7095 |
| 73 | 1.5775 |
| 74 | 1.709 |
| 75 | 1.7035 |
| 76 | 1.7274 |
| 77 | 1.6649 |
| 78 | 1.7897 |
| 79 | 1.6574 |
| 80 | 1.5928 |
| 81 | 1.6719 |
| 82 | 1.7306 |

The invention claimed is:

1. A compound of formula (I):

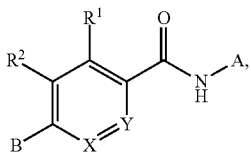

wherein:

X is N or $CR^3$;

Y is N or $CR^4$; with the proviso that not both X and Y are N;

A is a bicyclic 9-membered heteroaryl comprising two or three heteroatoms independently selected from N or O, wherein A can be optionally substituted with one, two or three $R^5$;

B is a saturated or partially unsaturated mono- or bicyclic 4 to 9-membered heterocycloalkyl comprising one or two ring nitrogen atoms, the remaining ring atoms being carbon, wherein B can be optionally substituted with one, two or three $R^6$;

$R^1$ is hydrogen, halo, $C_{1-7}$-alkyl, $C_{1-7}$-haloalkyl, $C_{1-7}$-alkoxy or $C_{1-7}$-haloalkoxy;

$R^2$ is hydrogen, halo, $C_{1-7}$-alkyl, $C_{1-7}$-haloalkyl, $C_{1-7}$-alkoxy or $C_{1-7}$-haloalkoxy;

$R^3$ is hydrogen, halo, $C_{1-7}$-alkyl, $C_{1-7}$-haloalkyl, $C_{1-7}$-alkoxy or $C_{1-7}$-haloalkoxy;

$R^4$ is hydrogen, halo, $C_{1-7}$-alkyl, $C_{1-7}$-haloalkyl, $C_{1-7}$-alkoxy or $C_{1-7}$-haloalkoxy;

each $R^5$ is independently selected from halo, cyano, $C_{1-7}$-alkyl, $C_{1-7}$-haloalkyl or $C_{3-7}$-cycloalkyl;

each $R^6$ is independently selected from $C_{1-7}$-alkyl, or two $R^6$ together form a $C_{2-7}$-alkylene;

or a pharmaceutically acceptable salt thereof.

2. The compound according to claim 1, wherein A is selected from the group of imidazo[1,2-a]pyrazin-2-yl, imidazo[1,2-a]pyridinyl, and benzo[d]oxazolyl, which can be optionally substituted with one, two or three $R^5$.

3. The compound according to claim 1, wherein A is selected from the group of imidazo[1,2-a]pyrazin-2-yl substituted with two $C_{1-7}$-alkyl, imidazo[1,2-a]pyridin-6-yl substituted with one or two $C_{1-7}$-alkyl, imidazo[1,2-a]pyridin-6-yl substituted with one $C_{1-7}$-alkyl and one halo, imidazo[1,2-a]pyridin-6-yl substituted with one $C_{1-7}$-alkyl and one $C_{1-7}$-haloalkyl, benzo[d]oxazol-6-yl substituted with one $C_{1-7}$-alkyl, and benzo[d]oxazol-6-yl substituted with one $C_{1-7}$-alkyl and one halo.

4. The compound according to claim 1, wherein A is selected from 2-methylbenzo[d]oxazol-6-yl, 4-fluoro-2-methylbenzo[d]oxazol-6-yl, 6,8-dimethylimidazo[1,2-a]pyrazin-2-yl, 2-methylimidazo[1,2-a]pyridin-6-yl, 2,7-dimethylimidazo[1,2-a]pyridin-6-yl, 2,8-dimethylimidazo[1,2-a]pyridin-6-yl, 2-methyl-8-(trifluoromethyl)imidazo[1,2-a]pyridin-6-yl, 8-fluoro-2-methylimidazo[1,2-a]pyridin-6-yl, and 8-chloro-2-methylimidazo[1,2-a]pyridin-6-yl.

5. The compound according to claim 1, wherein each $R^5$ is independently selected from halo, $C_{1-7}$-alkyl, or $C_{1-7}$-haloalkyl.

6. The compound according to claim 1, wherein each $R^5$ is independently selected from methyl, fluoro, chloro, and trifluoromethyl.

7. The compound according to claim 1, wherein B as defined herein is further characterized in that one ring nitrogen atoms is basic.

8. The compound according to claim 1, wherein B is selected from 1,2,3,6-tetrahydropyridinyl, 2,6-diazaspiro[3.3]heptanyl, hexahydropyrrolo[3,4-c]pyrrolyl, hexahydropyrrolo[1,2-a]pyrazinyl, piperazinyl, and piperidinyl, wherein each can be optionally substituted with one, two or three R⁶.

9. The compound according to claim 1, wherein B is selected from piperazin-1-yl, 3-methyl-piperazin-1-yl, and 3,3-dimethylpiperazin-1-yl.

10. The compound according to claim 1, wherein each R⁶ is $C_{1-7}$-alkyl.

11. The compound according to claim 1, wherein each R⁶ is independently selected from methyl, and ethyl.

12. The compound according to claim 1, wherein X is CR³ and Y is CR⁴, or X is N and Y is CR⁴, or X is CR³ and Y is N.

13. The compound according to claim 1, wherein X is CR³ and Y is CR⁴.

14. The compound according to claim 1, wherein X is N and Y is CR⁴.

15. The compound according to claim 1, wherein R¹ is hydrogen, halo, $C_{1-7}$-alkoxy or $C_{1-7}$-haloalkoxy.

16. The compound according to claim 1, wherein R¹ is hydrogen, fluoro, methoxy, ethoxy or trifluoroethoxy.

17. The compound according to claim 1, wherein R¹ is hydrogen.

18. The compound according to claim 1, wherein R² is hydrogen, halo, or $C_{1-7}$-alkyl.

19. The compound according to claim 1, wherein R² is hydrogen, fluoro or methyl.

20. The compound according to claim 1, wherein R² is hydrogen.

21. The compound according to claim 1, wherein R³ is hydrogen or fluoro.

22. The compound according to claim 1, wherein R³ is hydrogen.

23. The compound according to claim 1, wherein R⁴ is hydrogen, halo or $C_{1-7}$-alkoxy.

24. The compound according to claim 1, wherein R⁴ is hydrogen, fluoro, methoxy, ethoxy or trifluoroethoxy.

25. The compound according to claim 1, wherein R⁴ is hydrogen or fluoro.

26. The compound according to claim 1, wherein R⁴ is hydrogen, halo or $C_{1-7}$-alkoxy.

27. The compound according to claim 1, selected from the group consisting of:
  N-(6,8-dimethylimidazo[1,2-a]pyrazin-2-yl)-4-(piperazin-1-yl)benzamide;
  rac-N-(6,8-dimethylimidazo[1,2-a]pyrazin-2-yl)-4-(3-methylpiperazin-1-yl)benzamide;
  N-(6,8-Dimethyl-imidazo[1,2-a]pyrazin-2-yl)-4-((S)-3-methyl-piperazin-1-yl)-benzamide;
  N-(6,8-dimethylimidazo[1,2-a]pyrazin-2-yl)-2-fluoro-4-(4-methylpiperazin-1-yl)benzamide;
  rac-N-(6,8-dimethylimidazo[1,2-a]pyrazin-2-yl)-2-fluoro-4-(3-methylpiperazin-1-yl)benzamide;
  N-(6,8-dimethylimidazo[1,2-a]pyrazin-2-yl)-6-(4-methylpiperazin-1-yl)nicotinamide;
  rac-N-(6,8-dimethylimidazo[1,2-a]pyrazin-2-yl)-6-(3-methylpiperazin-1-yl)nicotinamide;
  N-(6,8-dimethylimidazo[1,2-a]pyrazin-2-yl)-6-(4-ethylpiperazin-1-yl)nicotinamide;
  N-(6,8-dimethylimidazo[1,2-a]pyrazin-2-yl)-5-(4-methylpiperazin-1-yl)picolinamide;
  rac-N-(6,8-dimethylimidazo[1,2-a]pyrazin-2-yl)-5-(3-methylpiperazin-1-yl)picolinamide;
  N-(6,8-dimethylimidazo[1,2-a]pyrazin-2-yl)-5-(piperazin-1-yl)picolinamide;
  rac-N-(2-methylimidazo[1,2-a]pyridin-6-yl)-6-(3-methylpiperazin-1-yl)nicotinamide;
  6-(3,3-dimethylpiperazin-1-yl)-N-(2-methylimidazo[1,2-a]pyridin-6-yl)nicotinamide;
  N-(2-methylimidazo[1,2-a]pyridin-6-yl)-6-(piperazin-1-yl)nicotinamide;
  6-hexahydropyrrolo[3,4-c]pyrrol-2(1H)-yl)-N-(2-methyl-imidazo[1,2-a]pyridin-6-yl)nicotinamide;
  N-(2-methylimidazo[1,2-a]pyridin-6-yl)-6-(2,6-diazaspiro[3.3]heptan-2-yl)nicotinamide;
  rac-N-(2-methylimidazo[1,2-a]pyridin-6-yl)-5-(3-methylpiperazin-1-yl)picolinamide;
  rac-2-fluoro-N-(2-methylimidazo[1,2-a]pyridin-6-yl)-4-(3-methylpiperazin-1-yl)benzamide;
  N-(2-methyl-8-(trifluoromethyl)imidazo[1,2-a]pyridin-6-yl)-6-(piperazin-1-yl)nicotinamide;
  rac-N-(2-methyl-8-(trifluoromethyl)imidazo[1,2-a]pyridin-6-yl)-6-(3-methylpiperazin-1-yl)nicotinamide;
  (S)-6-(hexahydropyrrolo[1,2-a]pyrazin-2(1H)-yl)-N-(2-methyl-8-(trifluoromethyl)imidazo[1,2-a]pyridin-6-yl)nicotinamide;
  6-(3,5-dimethylpiperazin-1-yl)-N-(2-methyl-8-(trifluoromethyl)imidazo[1,2-a]pyridin-6-yl)nicotinamide;
  6-(3,5-dimethylpiperazin-1-yl)-N-(4-fluoro-2-methylbenzo[d]oxazol-6-yl)nicotinamide;
  N-(4-fluoro-2-methylbenzo[d]oxazol-6-yl)-6-(4-methylpiperazin-1-yl)nicotinamide;
  (S)—N-(4-fluoro-2-methylbenzo[d]oxazol-6-yl)-6-(hexahydropyrrolo[1,2-a]pyrazin-2(1H)-yl)nicotinamide;
  N-(4-Fluoro-2-methyl-benzooxazol-6-yl)-6-piperazin-1-yl-nicotinamide;
  rac-N-(4-Fluoro-2-methyl-benzooxazol-6-yl)-6-(3-methyl-piperazin-1-yl)-nicotinamide;
  N-(4-fluoro-2-methylbenzo[d]oxazol-6-yl)-4-(piperazin-1-yl)benzamide;
  rac-N-(4-fluoro-2-methylbenzo[d]oxazol-6-yl)-4-(3-methylpiperazin-1-yl)benzamide;
  4-(3,5-dimethylpiperazin-1-yl)-N-(4-fluoro-2-methylbenzo[d]oxazol-6-yl)benzamide;
  (S)-2-fluoro-4-(hexahydropyrrolo[1,2-a]pyrazin-2(1H)-yl)-N-(2-methylimidazo[1,2-a]pyridin-6-yl)benzamide;
  N-(8-fluoro-2-methylimidazo[1,2-a]pyridin-6-yl)-6-(4-methylpiperazin-1-yl)nicotinamide;
  (S)-2-Fluoro-N-(4-fluoro-2-methyl-benzooxazol-6-yl)-4-(S)-hexahydro-pyrrolo[1,2-a]pyrazin-2-yl-benzamide;
  (R)-2-fluoro N-(4-fluoro-2-methylbenzo[d]oxazol-6-yl)-4-(hexahydropyrrolo[1,2-a]pyrazin-2(1H)-yl)benzamide;
  (S)-2-fluoro-4-(hexahydropyrrolo[1,2-a]pyrazin-2(1H)-yl)-N-(2-methyl-8-(trifluoromethyl)imidazo[1,2-a]pyridin-6-yl)benzamide;
  N-(8-fluoro-2-methylimidazo[1,2-a]pyridin-6-yl)-4-(piperazin-1-yl)benzamide;
  rac-N-(2,8-dimethylimidazo[1,2-a]pyridin-6-yl)-2-fluoro-4-(3-methylpiperazin-1-yl)benzamide;
  rac-2-fluoro-N-(2-methylbenzo[d]oxazol-6-yl)-4-(3-methylpiperazin-1-yl)benzamide;
  rac-2-fluoro-N-(8-fluoro-2-methylimidazo[1,2-a]pyridin-6-yl)-4-(3-methylpiperazin-1-yl)benzamide;
  2-fluoro-N-(8-fluoro-2-methylimidazo[1,2-a]pyridin-6-yl)-4-(piperazin-1-yl)benzamide;
  N-(8-fluoro-2-methylimidazo[1,2-a]pyridin-6-yl)-6-(piperazin-1-yl)nicotinamide;
  rac-N-(8-fluoro-2-methylimidazo[1,2-a]pyridin-6-yl)-6-(3-methylpiperazin-1-yl)nicotinamide;
  rac-N-(8-fluoro-2-methylimidazo[1,2-a]pyridin-6-yl)-5-(3-methylpiperazin-1-yl)picolinamide;

2-fluoro-N-(2-methylimidazo[1,2-a]pyridin-6-yl)-4-(piperazin-1-yl)benzamide;
rac-2,3-difluoro-N-(8-fluoro-2-methylimidazo[1,2-a]pyridin-6-yl)-4-(3-methylpiperazin-1-yl)benzamide;
rac-2,5-difluoro-N-(8-fluoro-2-methylimidazo[1,2-a]pyridin-6-yl)-4-(3-methylpiperazin-1-yl)benzamide;
rac-5-fluoro-N-(8-fluoro-2-methylimidazo[1,2-a]pyridin-6-yl)-6-(3-methylpiperazin-1-yl)nicotinamide;
rac-3-fluoro-N-(8-fluoro-2-methylimidazo[1,2-a]pyridin-6-yl)-5-(3-methylpiperazin-1-yl)picolinamide;
rac-2,6-difluoro-N-(8-fluoro-2-methylimidazo[1,2-a]pyridin-6-yl)-4-(3-methylpiperazin-1-yl)benzamide;
(S)-2-fluoro-N-(8-fluoro-2-methylimidazo[1,2-a]pyridin-6-yl)-4-(3-methylpiperazin-1-yl)benzamide;
(R)-2-fluoro-N-(8-fluoro-2-methylimidazo[1,2-a]pyridin-6-yl)-4-(3-methylpiperazin-1-yl)benzamide;
rac-N-(2,7-dimethylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-5-fluoro-6-(3-methylpiperazin-1-yl)nicotinamide;
rac-N-(8-chloro-2-methylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-6-(3-methylpiperazin-1-yl)nicotinamide;
rac-N-(8-chloro-2-methylimidazo[1,2-a]pyridin-6-yl)-3-fluoro-5-(3-methylpiperazin-1-yl)picolinamide;
rac-N-(8-chloro-2-methylimidazo[1,2-a]pyridin-6-yl)-2,6-difluoro-4-(3-methylpiperazin-1-yl)benzamide;
2-fluoro-N-(4-fluoro-2-methylbenzo[d]oxazol-6-yl)-4-(piperazin-1-yl)benzamide;
2-fluoro-N-(2-methyl-8-(trifluoromethyl)imidazo[1,2-a]pyridin-6-yl)-4-(piperazin-1-yl)benzamide;
2-fluoro-N-(2-methylimidazo[1,2-a]pyridin-6-yl)-4-(1,2,3,6-tetrahydropyridin-4-yl)benzamide;
2-fluoro-N-(8-fluoro-2-methylimidazo[1,2-a]pyridin-6-yl)-4-(1,2,3,6-tetrahydropyridin-4-yl)benzamide;
N-(8-fluoro-2-methylimidazo[1,2-a]pyridin-6-yl)-6-(1,2,3,6-tetrahydropyridin-4-yl)nicotinamide;
N-(2-methylimidazo[1,2-a]pyridin-6-yl)-5-(1,2,3,6-tetrahydropyridin-4-yl)picolinamide;
N-(8-fluoro-2-methylimidazo[1,2-a]pyridin-6-yl)-2-methoxy-6-(piperazin-1-yl)nicotinamide;
2-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-3-methyl-4-(piperazin-1-yl)benzamide;
N-(8-fluoro-2-methylimidazo[1,2-a]pyridin-6-yl)-5-methyl-6-(piperazin-1-yl)nicotinamide;
4-fluoro-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-4-methoxy-6-(piperazin-1-yl)nicotinamide;
4-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-4-(2,2,2-trifluoroethoxy)nicotinamide;
2-ethoxy-N-(8-fluoro-2-methylimidazo[1,2-a]pyridin-6-yl)-6-(piperazin-1-yl)nicotinamide;
N-(8-fluoro-2-methylimidazo[1,2-a]pyridin-6-yl)-6-(piperazin-1-yl)-2-(2,2,2-trifluoroethoxy)nicotinamide;
rac-N-(8-fluoro-2-methylimidazo[1,2-a]pyridin-6-yl)-2-methoxy-6-(3-methylpiperazin-1-yl)nicotinamide;
6-(3,3-dimethylpiperazin-1-yl)-N-(8-fluoro-2-methylimidazo[1,2-a]pyridin-6-yl)-2-methoxynicotinamide;
rac-N-(8-fluoro-2-methylimidazo[1,2-a]pyridin-6-yl)-4-methoxy-6-(3-methylpiperazin-1-yl)nicotinamide;
N-(2-methylimidazo[1,2-a]pyridin-6-yl)-6-(1,2,3,6-tetrahydropyridin-4-yl)nicotinamide;
N-(2-methylimidazo[1,2-a]pyridin-6-yl)-6-(1-methylpiperidin-4-yl)nicotinamide;
N-(8-fluoro-2-methylimidazo[1,2-a]pyridin-6-yl)-6-(piperidin-4-yl)nicotinamide;
N-(8-fluoro-2-methylimidazo[1,2-a]pyridin-6-yl)-6-(1-methylpiperidin-4-yl)nicotinamide;
2-fluoro-N-(8-fluoro-2-methylimidazo[1,2-a]pyridin-6-yl)-4-(piperidin-4-yl)benzamide; and
rac-6-(3,4-dimethylpiperazin-1-yl)-N-(2-methylimidazo[1,2-a]pyridin-6-yl)nicotinamide;
or a pharmaceutically acceptable salt thereof.

28. The compound according to claim 1, selected from the group consisting of:
rac-2-fluoro-N-(8-fluoro-2-methylimidazo[1,2-a]pyridin-6-yl)-4-(3-methylpiperazin-1-yl)benzamide;
2-fluoro-N-(8-fluoro-2-methylimidazo[1,2-a]pyridin-6-yl)-4-(piperazin-1-yl)benzamide;
N-(8-fluoro-2-methylimidazo[1,2-a]pyridin-6-yl)-6-(piperazin-1-yl)nicotinamide;
rac-3-fluoro-N-(8-fluoro-2-methylimidazo[1,2-a]pyridin-6-yl)-5-(3-methylpiperazin-1-yl)picolinamide;
rac-2,6-difluoro-N-(8-fluoro-2-methylimidazo[1,2-a]pyridin-6-yl)-4-(3-methylpiperazin-1-yl)benzamide;
(S)-2-fluoro-N-(8-fluoro-2-methylimidazo[1,2-a]pyridin-6-yl)-4-(3-methylpiperazin-1-yl)benzamide;
(R)-2-fluoro-N-(8-fluoro-2-methylimidazo[1,2-a]pyridin-6-yl)-4-(3-methylpiperazin-1-yl)benzamide;
rac-N-(8-chloro-2-methylimidazo[1,2-a]pyridin-6-yl)-2-fluoro-4-(3-methylpiperazin-1-yl)benzamide;
rac-N-(8-chloro-2-methylimidazo[1,2-a]pyridin-6-yl)-3-fluoro-5-(3-methylpiperazin-1-yl)picolinamide;
2-fluoro-N-(8-fluoro-2-methylimidazo[1,2-a]pyridin-6-yl)-4-(1,2,3,6-tetrahydropyridin-4-yl)benzamide;
N-(8-fluoro-2-methylimidazo[1,2-a]pyridin-6-yl)-6-(1,2,3,6-tetrahydropyridin-4-yl)nicotinamide;
4-fluoro-N-(8-fluoro-2-methylimidazo[1,2-a]pyridin-6-yl)-6-(piperazin-1-yl)nicotinamide;
4-ethoxy-N-(8-fluoro-2-methylimidazo[1,2-a]pyridin-6-yl)-6-(piperazin-1-yl)nicotinamide;
2-ethoxy-N-(8-fluoro-2-methylimidazo[1,2-a]pyridin-6-yl)-6-(piperazin-1-yl)nicotinamide;
rac-N-(8-fluoro-2-methylimidazo[1,2-a]pyridin-6-yl)-2-methoxy-6-(3-methylpiperazin-1-yl)nicotinamide; and
rac-N-(8-fluoro-2-methylimidazo[1,2-a]pyridin-6-yl)-4-methoxy-6-(3-methylpiperazin-1-yl)nicotinamide;
or a pharmaceutically acceptable salts thereof.

29. A process for the preparation of a compound according to claim 1, comprising the step of:

a) the Buchwald-Hartwig amination reaction of a compound of formula (II)

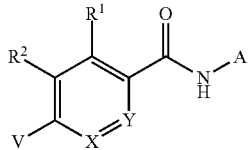

(II)

with a compound of formula B—H, in the presence of a catalyst and a ligand and a base and a solvent, wherein the hydrogen H of the compound of formula B—H is bound to a ring nitrogen atom of B, V is chloro or bromo, and A, B, X, Y, $R^1$, and $R^2$ are as defined in claim 1; or b) a nucleophilic aromatic substitution reaction between a compound of formula (II) with a compound of formula B—H by heating in a solvent, wherein the hydrogen H of the compound of formula B—H is bound to a ring nitrogen atom of B, V is fluoro if X is $CR^3$ or V is chloro if X is N, and A, B, X, Y, $R^1$, $R^2$ and $R^3$ are as defined in claim 1; or c) the Suzuki coupling reaction of a compound of formula (II) with a compound of formula PG-B-pinB in the presence of a base and a catalyst, followed by removal of PG, wherein pinB is pinacolboranyl which is bound to a ring carbon atom of B, PG is an amino-protecting group, V is fluoro or chloro, and wherein A, B, X, Y, $R^1$, and $R^2$ are as defined in claim 1; or d) the amidation reaction of a compound of formula (III)

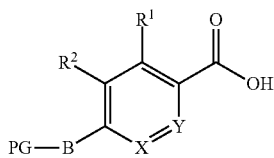

(III)

with a compound of formula A-$NH_2$ in the presence of a tertiary amine and a coupling reagent, optionally followed by the removal of PG, wherein PG is an optional amino-protecting group, and wherein A, B, X, Y, $R^1$, and $R^2$ are as defined in claim 1.

30. A pharmaceutical composition, comprising a therapeutically effective amount of a compound according to claim 1, or a pharmaceutically acceptable salt thereof, and one or more pharmaceutically acceptable excipients.

31. A method for the treatment or prevention of spinal muscular atrophy (SMA), comprising, the step of administering a therapeutically effective amount of a compound according to claim 1, or a pharmaceutically acceptable salt thereof, to a subject in need thereof.

\* \* \* \* \*

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggaaggt gctcacatt                                                  19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctttatgtt tttggcgtct tc                                              22

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-6FAM
<220> FEATURE:
<223> OTHER INFORMATION: 3'-TAMRA

<400> SEQUENCE: 3
aaggagaaat gctggcatag agcagc                                          26

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
```

```
<223> OTHER INFORMATION: 5'-VIC
<220> FEATURE:
<223> OTHER INFORMATION: 3'-TAMRA

<400> SEQUENCE: 4
cgcctggtca ccagggctgc t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caacggattt ggtcgtattg g                                              21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgatggcaac aatatccact ttacc                                          25
```